United States Patent
Drescher et al.

(10) Patent No.: US 8,486,984 B2
(45) Date of Patent: Jul. 16, 2013

(54) AMINOMETHYL SUBSTITUTED BICYCLIC AROMATIC COMPOUNDS SUITABLE FOR TREATING DISORDERS THAT RESPOND TO MODULATION OF THE DOPAMINE $D_3$ RECEPTOR

(75) Inventors: Karla Drescher, Dossenheim (DE); Andreas Haupt, Schwetzingen (DE); Liliane Unger, Ludwigshafen (DE); Sean C. Turner, Mannheim (DE); Wilfried Braje, Mannheim (DE); Roland Grandel, Dossenheim (DE)

(73) Assignee: Abbott GmbH & Co., KG, Wiesbaden (DE)

( * ) Notice: Subject to any disclaimer, the term of this patent is extended or adjusted under 35 U.S.C. 154(b) by 1255 days.

(21) Appl. No.: 11/665,287

(22) PCT Filed: Oct. 14, 2005

(86) PCT No.: PCT/EP2005/011093
§ 371 (c)(1),
(2), (4) Date: Sep. 24, 2007

(87) PCT Pub. No.: WO2006/040180
PCT Pub. Date: Apr. 20, 2006

(65) Prior Publication Data
US 2011/0144146 A1    Jun. 16, 2011

Related U.S. Application Data

(60) Provisional application No. 60/618,744, filed on Oct. 14, 2004.

(51) Int. Cl.
*A61K 31/404*     (2006.01)
*A61K 31/4184*   (2006.01)
*C07D 209/14*    (2006.01)
*C07D 235/14*    (2006.01)

(52) U.S. Cl.
USPC ......... 514/394; 514/415; 548/309.7; 548/503

(58) Field of Classification Search
USPC .............................................. 548/309.7, 503
See application file for complete search history.

(56) References Cited

U.S. PATENT DOCUMENTS
5,708,018 A    1/1998    Haadsma-Svensson et al.

FOREIGN PATENT DOCUMENTS
WO    WO 95/04713    2/1995
WO    WO 96/23760    8/1996
WO    WO 97/45403    12/1997
WO    WO 97/45503    12/1997

OTHER PUBLICATIONS

Kato, et al., Document No. 134:266103 retrieved from CAPLUS, Mar. 29, 2001.*
Kato, et al., Document No. 129:216428 retrieved from CAPLUS, Sep. 3, 1998.*
Torrens, et al. Document 142:240323 retrieved from CAPLUS, Feb. 17, 2005.*
J.C. Schwartz et al., the Dopamine $D_3$ Receptor as a Target for Antipsychotics, in Novel Antipsychotic Drugs, H.Y. Meltzer, Ed. Raven Press, New York, 1992, pp. 135-144.
M. Dooley et al., Drugs and Aging 1998, 12, 495-514.
J. N. Joyce, Pharmacology and Therapeutics 2001, 90, pp. 231-59 "The Dopamine $D_3$ Receptor as a Therapeutic Target for Antipsychotic and Antiparkinsonian Drugs".
P. Sokoloff et al., Localization and Function of the $D_3$ Dopamine Receptor, Arzneim. Frosch./Drug Res. 42(1), 224 (1992).
P. Sokoloff et al., Molecular Cloning and Characterization of a Novel Dopamine Receptor ($D_3$) as a Target for Neuroleptics, Nature, 347, 146 (1990).
Tetrahedron, vol. 57, No. 6, 2001, pp. 1041-1048, XP004316535, Synthesis of 5-(sulfamoylmethyl)indoles.
P. J. Murray et al. "Novel 6-substituted 2-aminotetralins with potent and selective affinity for the dopamine D3 receptor", Bioorganic & Medicinal Chemistry Letters, vol. 6, No. 4, pp. 403-408, 1996.

* cited by examiner

*Primary Examiner* — Shawquia Young
(74) *Attorney, Agent, or Firm* — Lisa V. Mueller; Michael Best & Friedrich LLP

(57) ABSTRACT

The present invention relates to an aminomethyl substituted bicyclic aromatic compound of the formula I

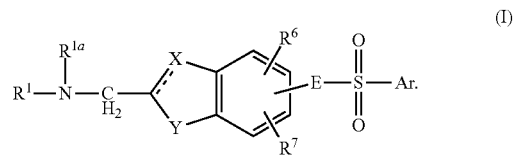

The invention also relates to the use of a compound of the formula I or a pharmaceutically acceptable salt thereof for preparing a pharmaceutical composition for the treatment of a medical disorder susceptible to treatment with a dopamine D3 receptor ligand.

26 Claims, No Drawings

AMINOMETHYL SUBSTITUTED BICYCLIC AROMATIC COMPOUNDS SUITABLE FOR TREATING DISORDERS THAT RESPOND TO MODULATION OF THE DOPAMINE $D_3$ RECEPTOR

CROSS-REFERENCE TO RELATED APPLICATIONS

This is a U.S. national stage entry of International Patent Application No. PCT/EP2005/011093, filed on Oct. 14, 2005, which claims priority to U.S. Provisional Patent Application No. 60/618,744, filed on Oct. 14, 2004, the contents of all of which are fully incorporated herein by reference.

BACKGROUND OF THE INVENTION

The present invention relates to novel aminomethyl substituted bicyclic aromatic compounds. The compounds possess valuable therapeutic properties and are suitable, in particular, for treating diseases that respond to modulation of the dopamine $D_3$ receptor.

Neurons obtain their information by way of G protein-coupled receptors, inter alia. A large number of substances exert their effect by way of these receptors. One of them is dopamine. Confirmed findings exist with regard to the presence of dopamine and its physiological function as a neurotransmitter. Disorders in the dopaminergic transmitter system result in diseases of the central nervous system which include, for example, schizophrenia, depression and Parkinson's disease. These diseases, and others, are treated with drugs which interact with the dopamine receptors.

Up until 1990, two subtypes of dopamine receptor had been clearly defined pharmacologically, namely the $D_1$ and $D_2$ receptors. More recently, a third subtype was found, namely the $D_3$ receptor which appears to mediate some effects of antipsychotics and antiparkinsonians (J. C. Schwartz et al., The Dopamine $D_3$ Receptor as a Target for Antipsychotics, in Novel Antipsychotic Drugs, H. Y. Meltzer, Ed. Raven Press, New York 1992, pages 135-144; M. Dooley et al., Drugs and Aging 1998, 12, 495-514, J. N. Joyce, Pharmacology and Therapeutics 2001, 90, pp. 231-59 "The Dopamine $D_3$ Receptor as a Therapeutic Target for Antipsychotic and Antiparkinsonian Drugs").

Since then, the dopamine receptors have been divided into two families. On the one hand, there is the $D_2$ group, consisting of $D_2$, $D_3$ and $D_4$ receptors, and, on the other hand, the $D_1$ group, consisting of $D_1$ and $D_5$ receptors. Whereas $D_1$ and $D_2$ receptors are widely distributed, $D_3$ receptors appear to be expressed regioselectively. Thus, these receptors are preferentially to be found in the limbic system and the projection regions of the mesolimbic dopamine system, especially in the nucleus accumbens, but also in other regions, such as the amygdala. Because of this comparatively regioselective expression, $D_3$ receptors are regarded as being a target having few side-effects and it is assumed that while a selective $D_3$ ligand would have the properties of known antipsychotics, it would not have their dopamine $D_2$ receptor-mediated neurological side-effects (P. Sokoloff et al., Localization and Function of the $D_3$ Dopamine Receptor, Arzneim. Forsch./Druq Res. 42(1), 224 (1992); P. Sokoloff et al. Molecular Cloning and Characterization of a Novel Dopamine Receptor ($D_3$) as a Target for Neuroleptics, Nature, 347, 146 (1990)).

WO 95/04713, WO 96/23760 and WO 97/45403 disclose amino substituted bicyclic aromatic compounds having an affinity for the dopamine $D_3$ receptor. Some of these compounds possess a certain selectivity for the dopamine $D_3$ receptor in comparison with their affinity for the $D_2$ receptor. They have therefore been proposed as being suitable for treating diseases of the central nervous system. Unfortunately their affinity and selectivity towards the $D_3$ receptor is only moderate or their pharmacological profile are not satisfactory. Consequently there is an ongoing need to provide new compounds, which either have an high affinity and an improved selectivity. The compounds should also have good pharmacological profile, e.g. a high brain plasma ratio, a high bioavailability, good metabolic stability or a decreased inhibition of the mitochondrial respiration.

SUMMARY OF THE INVENTION

The invention is based on the object of providing compounds which act as highly selective dopamine $D_3$ receptor ligands. This object is surprisingly achieved by means of aminomethyl substituted bicyclic aromatic compounds of the formula I

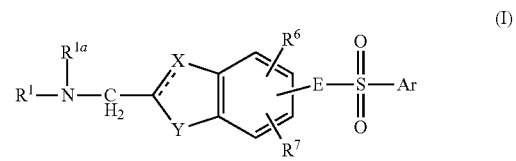

(I)

wherein

Ar is a cyclic radical selected from the group consisting of phenyl, a 5- or 6-membered C-bound heteroaromatic radical comprising as ring members 1, 2 or 3 heteroatoms which are, independently of each other, selected from O, S and N, and a phenyl ring fused to a saturated or unsaturated 5- or 6-membered carbocyclic or heterocyclic ring, where the heterocyclic ring comprises as ring members 1, 2 or 3 heteroatoms selected from N, O and S and/or 1, 2 or 3 heteroatom-containing groups each independently selected from $NR^8$, where $R^8$ is H, $C_1$-$C_4$-alkyl, fluorinated $C_1$-$C_4$-alkyl, $C_1$-$C_4$-alkylcarbonyl or fluorinated $C_1$-$C_4$-alkylcarbonyl, and where the cyclic radical Ar may carry 1, 2 or 3 substituents $R^a$;

$R^a$ is halogen, $C_1$-$C_6$-alkyl, fluorinated $C_1$-$C_6$-alkyl, $C_1$-$C_6$-hydroxyalkyl, $C_1$-$C_6$-alkoxy-$C_1$-$C_6$-alkyl, $C_2$-$C_6$-alkenyl, fluorinated $C_2$-$C_6$-alkenyl, $C_3$-$C_6$-cycloalkyl, fluorinated $C_3$-$C_6$-cycloalkyl, $C_1$-$C_6$-alkoxy, $C_1$-$C_6$-hydroxyalkoxy, $C_1$-$C_6$-alkoxy-$C_1$-$C_6$-alkoxy, fluorinated $C_1$-$C_6$-alkoxy, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl, fluorinated $C_1$-$C_6$-alkylsulfonyl, CN, nitro, $C_1$-$C_6$-alkylcarbonyl, fluorinated $C_1$-$C_6$-alkylcarbonyl, $C_1$-$C_6$-alkylcarbonylamino, fluorinated $C_1$-$C_6$-alkylcarbonylamino, $C_1$-$C_6$-alkylcarbonyloxy, fluorinated $C_1$-$C_6$-alkylcarbonyloxy, $C_1$-$C_6$-alkoxycarbonyl, carboxy, NH—C(O)—$NR^4R^5$, $NR^4R^5$, $NR^4R^5$—$C_1$-$C_6$-alkylene, O—$NR^4R^5$, C(O)$NR^4R^5$, $SO_2NR^4R^5$, phenylsulfonyl, benzyloxy, phenyl, phenoxy, or a saturated or unsaturated 3- to 7-membered heterocyclic ring comprising as ring members 1, 2, 3 or 4 heteroatoms selected from N, O and S and/or 1, 2 or 3 heteroatom-containing groups selected from $NR^9$, where $R^9$ has one of the meanings given for $R^8$, SO, $SO_2$ and CO, and where the 5 last-mentioned radicals $R^a$ may carry 1, 2, 3 or 4 substituents selected from hydroxy and the radicals $R^a$;

X is a covalent bond or N—$R^2$, $CHR^2$, $CHR^2CH_2$, N or C—$R^2$;

Y is N—$R^{2a}$, $CHR^{2a}$, $CHR^{2a}CH_2$ or $CHR^{2a}CH_2CH_2$;

---- is a single bond or a double bond;

E is $CH_2$ or $NR^3$;

$R^1$ is H, $C_1$-$C_4$-alkyl, $C_3$-$C_4$-cycloalkyl, $C_3$-$C_4$-cycloalkylmethyl, $C_3$-$C_4$-alkenyl, fluorinated $C_1$-$C_4$-alkyl, fluorinated $C_3$-$C_4$-cycloalkyl, fluorinated $C_3$-$C_4$-cycloalkylmethyl, fluorinated $C_3$-$C_4$-alkenyl, formyl or $C_1$-$C_3$-alkylcarbonyl;

$R^{1a}$ is H, $C_1$-$C_4$-alkyl, $C_3$-$C_4$-cycloalkyl, $C_3$-$C_4$-alkenyl, fluorinated $C_1$-$C_4$-alkyl, fluorinated $C_3$-$C_4$-cycloalkyl, fluorinated $C_3$-$C_4$-alkenyl, $R^2$ and $R^{2a}$ each independently are H, $CH_3$, $CH_2F$, $CHF_2$ or $CF_3$ or $R^{1a}$ and $R^2$ or $R^{1a}$ and $R^{2a}$ together are $(CH_2)_n$ with n being 1, 2 or 3;

$R^3$ is H or $C_1$-$C_4$-alkyl;

$R^4$ and $R^5$ independently of each other are H, $C_1$-$C_4$-alkyl, fluorinated $C_1$-$C_4$-alkyl or $C_1$-$C_4$-alkoxy or may form, together with N, a 4-, 5- or 6-membered saturated or unsaturated ring;

$R^6$ and $R^7$ independently of each other are H or halogen;

and the physiologically tolerated acid addition salts thereof.

The present invention therefore relates to aminomethyl substituted bicyclic aromatic compounds of the general formula I and to their physiologically tolerated acid addition salts.

The present invention also relates to a pharmaceutical composition which comprises at least one aminomethyl substituted bicyclic aromatic compound of the formula I and/or at least one physiologically tolerated acid addition salt of I, where appropriate together with physiologically acceptable carriers and/or auxiliary substances.

The present invention also relates to a method for treating disorders which respond to influencing by dopamine $D_3$ receptor antagonists or dopamine $D_3$ agonists, said method comprising administering an effective amount of at least one aminomethyl substituted bicyclic aromatic compound of the formula I and/or at least one physiologically tolerated acid addition salt of I to a subject in need thereof.

DETAILED DESCRIPTION OF THE INVENTION

The diseases which respond to the influence of dopamine $D_3$ receptor antagonists or agonists include, in particular, disorders and diseases of the central nervous system, in particular affective disturbances, neurotic disturbances, stress disturbances and somatoform disturbances and psychoses, especially schizophrenia and depression and, in addition, disturbances of kidney function, in particular kidney function disturbances which are caused by diabetes mellitus (see WO 00/67847).

According to the invention, at least one compound of the general formula I having the meanings mentioned at the outset is used for treating the above mentioned indications.

Provided the compounds of the formula I of a given constitution may exist in different spatial arrangements, for example if they possess one or more centers of asymmetry, polysubstituted rings or double bonds, or as different tautomers, it is also possible to use enantiomeric mixtures, in particular racemates, diastereomeric mixtures and tautomeric mixtures, preferably, however, the respective essentially pure enantiomers, diastereomers and tautomers of the compounds of formula I and/or of their salts.

It is likewise possible to use physiologically tolerated salts of the compounds of the formula I, especially acid addition salts with physiologically tolerated acids. Examples of suitable physiologically tolerated organic and inorganic acids are hydrochloric acid, hydrobromic acid, phosphoric acid, sulfuric acid, $C_1$-$C_4$-alkylsulfonic acids, such as methanesulfonic acid, aromatic sulfonic acids, such as benzenesulfonic acid and toluenesulfonic acid, oxalic acid, maleic acid, fumaric acid, lactic acid, tartaric acid, adipic acid and benzoic acid. Other utilizable acids are described in Fortschritte der Arzneimittelforschung [Advances in drug research], Volume 10, pages 224 ff., Birkhäuser Verlag, Basel and Stuttgart, 1966.

The organic moieties mentioned in the above definitions of the variables are—like the term halogen—collective terms for individual listings of the individual group members. The prefix $C_n$-$C_m$ indicates in each case the possible number of carbon atoms in the group.

The term halogen denotes in each case fluorine, bromine, chlorine or iodine, in particular fluorine or chlorine.

$C_1$-$C_4$ Alkyl is a straight-chain or branched alkyl group having from 1 to 4 carbon atoms. Examples of an alkyl group are methyl, ethyl, n-propyl, iso-propyl, n-butyl, 2-butyl, iso-butyl or tert-butyl. $C_2$-$C_4$ Alkyl is ethyl, n-propyl, iso-propyl, n-butyl, 2-butyl, iso-butyl or tert-butyl. $C_1$-$C_2$ Alkyl is methyl or ethyl.

$C_1$-$C_6$ Alkyl is a straight-chain or branched alkyl group having from 1 to 6 carbon atoms. Examples include $C_1$-$C_4$ alkyl as mentioned above and also pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

Fluorinated $C_1$-$C_6$ alkyl is a straight-chain or branched alkyl group having from 1 to 6, in particular 1 to 4 carbon atoms, wherein at least one, e.g. 1, 2, 3, 4 or all of the hydrogen atoms are replaced by a fluorine atoms such as in fluoromethyl, difluoromethyl, trifluoromethyl, (R)-1-fluoroethyl, (S)-1-fluoroethyl, 2-fluoroethyl, 1,1-difluoroethyl, 2,2-difluoroethyl, 2,2,2-trifluoroethyl, (R)-1-fluoropropyl, (S)-1-fluoropropyl, 2-fluoropropyl, 3-fluoropropyl, 1,1-difluoropropyl, 2,2-difluoropropyl, 3,3-difluoropropyl, 3,3,3-trifluoropropyl, (R)-2-fluoro-1-methylethyl, (S)-2-fluoro-1-methylethyl, (R)-2,2-difluoro-1-methylethyl, (S)-2,2-difluoro-1-methylethyl, (R)-1,2-difluoro-1-methylethyl, (S)-1,2-difluoro-1-methylethyl, (R)-2,2,2-trifluoro-1-methylethyl, (S)-2,2,2-trifluoro-1-methylethyl, 2-fluoro-1-(fluoromethyl)ethyl, 1-(difluoromethyl)-2,2-difluoroethyl, (R)-1-fluorobutyl, (S)-1-fluorobutyl, 2-fluorobutyl, 3-fluorobutyl, 4-fluorobutyl, 1,1-difluorobutyl, 2,2-difluorobutyl, 3,3-difluorobutyl, 4,4-difluorobutyl, 4,4,4-trifluorobutyl, etc.;

Branched $C_3$-$C_6$ alkyl is alkyl having 3 to 6 carbon atoms at least one being a secondary or tertiary carbon atom. Examples are isopropyl, tert.-butyl, 2-butyl, isobutyl, 2-pentyl, 2-hexyl, 3-methylpentyl, 1,1-dimethylbutyl, 1,2-dimethylbutyl 1-methyl-1-ethylpropyl.

$C_1$-$C_6$ Alkoxy is a straight-chain or branched alkyl group having from 1 to 6, in particular 1 to 4 carbon atoms, which is bound to the remainder of the molecule via an oxygen atom. Examples include methoxy, ethoxy, n-propoxy, isopropoxy, n-butoxy, 2-butoxy, iso-butoxy, tert.-butoxy pentyloxy, 1-methylbutoxy, 2-methylbutoxy, 3-methylbutoxy, 2,2-dimethylpropoxy, 1-ethylpropoxy, hexyloxy, 1,1-dimethylpropoxy, 1,2-dimethylpropoxy, 1-methylpentyloxy, 2-methylpentyloxy, 3-methylpentyloxy, 4-methylpentyloxy, 1,1-dimethylbutyloxy, 1,2-dimethylbutyloxy, 1,3-dimethylbutyloxy, 2,2- dimethylbutyloxy, 2,3-dimethylbutyloxy, 3,3-dimethylbutyloxy, 1-ethylbutyloxy, 2-ethylbutyloxy, 1,1,2-trimethylpropoxy, 1,2,2-trimethylpropoxy, 1-ethyl-1-methylpropoxy and 1-ethyl-2-methylpropoxy;

Fluorinated $C_1$-$C_6$ alkoxy is a straight-chain or branched alkoxy group having from 1 to 6, in particular 1 to 4 carbon atoms, wherein at least one, e.g. 1, 2, 3, 4 or all of the hydrogen atoms are replaced by a fluorine atoms such as in fluoromethoxy, difluoromethoxy, trifluoromethoxy, (R)-1-fluoroethoxy, (S)-1-fluoroethoxy, 2-fluoroethoxy, 1,1-difluoroethoxy, 2,2-difluoroethoxy, 2,2,2-trifluoroethoxy, (R)-1-fluoropropoxy, (S)-1-fluoropropoxy, 2-fluoropropoxy, 3-fluoropropoxy, 1,1-difluoropropoxy, 2,2-difluoropropoxy, 3,3-difluoropropoxy, 3,3,3-trifluoropropoxy, (R)-2-fluoro-1-methylethoxy, (S)-2-fluoro-1-methylethoxy, (R)-2,2-difluoro-1-methylethoxy, (S)-2,2-difluoro-1-methylethoxy, (R)-1,2-difluoro-1-methylethoxy, (S)-1,2-difluoro-1-methylethoxy, (R)-2,2,2-trifluoro-1-methylethoxy, (S)-2,2,2-trifluoro-1-methylethoxy, 2-fluoro-1-(fluoromethyl)ethoxy, 1-(difluoromethyl)-2,2-difluoroethoxy, (R)-1-fluorobutoxy, (S)-1-fluorobutoxy, 2-fluorobutoxy, 3-fluorobutoxy, 4-fluorobutoxy, 1,1-difluorobutoxy, 2,2-difluorobutoxy, 3,3-difluorobutoxy, 4,4-difluorobutoxy, 4,4,4-trifluorobutoxy, etc.;

$C_1$-$C_6$-Hydroxyalkyl is an alkyl radical having from 1 to 6 carbon atoms as defined above, wherein one hydrogen atom is replaced by hydroxy. Examples comprise hydroxymethyl, 2-hydroxyethyl, 1-hydroxyethyl, 3-hydroxypropyl, 2-hydroxypropyl, 1-methyl-1-hydroxyethyl and the like.

$C_1$-$C_6$-Hydroxyalkoxy is an alkoxy radical having from 1 to 6, preferably from 2 to 4 carbon atoms as defined above, wherein one hydrogen atom is replaced by hydroxy. Examples comprise 2-hydroxyethyl, 3-hydroxypropyl, 2-hydroxypropyl, 1-methyl-2-hydroxyethyl and the like.

$C_1$-$C_6$-Alkoxy-$C_1$-$C_4$-alkyl is an alkyl radical having from 1 to 4 carbon atoms as defined above, wherein one hydrogen atom is replaced by $C_1$-$C_6$ alkoxy. Examples comprise methoxymethyl, 2-methoxyethyl, 1-methoxyethyl, 3-methoxypropyl, 2-methoxypropyl, 1-methyl-1-methoxyethyl, ethoxymethyl, 2-ethoxyethyl, 1-ethoxyethyl, 3-ethoxypropyl, 2-ethoxypropyl, 1-methyl-1-ethoxyethyl and the like.

$C_1$-$C_6$-Alkoxy-$C_1$-$C_4$-alkoxy is an alkoxy radical having from 1 to 4 carbon atoms as defined above, wherein one hydrogen atom is replaced by $C_1$-$C_6$ alkoxy. Examples comprise methoxymethoxy, 2-methoxyethoxy, 1-methoxyethoxy, 3-methoxypropoxy, 2-methoxypropoxy, 1-methyl-1-methoxyethoxy, ethoxymethoxy, 2-ethoxyethoxy, 1-ethoxyethoxy, 3-ethoxypropoxy, 2-ethoxypropoxy, 1-methyl-1-ethoxyethoxy and the like.

$C_1$-$C_6$-Alkylcarbonyl is a radical of the formula R—C(O)—, wherein R is an alkyl radical having from 1 to 6 carbon atoms as defined above. Examples comprise acetyl, propionyl, n-butyryl, 2-methylpropionyl, pivalyl and the like.

$C_1$-$C_6$-Alkylcarbonylamino is a radical of the formula R—C(O)—NH—, wherein R is an alkyl radical having from 1 to 6 carbon atoms as defined above. Examples comprise acetamido, propionamido, n-butyramido, 2-methylpropionamido, 2,2-dimethylpropionamido and the like.

$C_1$-$C_6$ Alkylcarbonyloxy is a radical of the formula R—C(O)—O—, wherein R is an alkyl radical having from 1 to 6 carbon atoms as defined above. Examples comprise acetyloxy, propionyloxy, n-butyryloxy, 2-methylpropionyloxy, 2,2-dimethylpropionyloxy and the like.

$C_1$-$C_6$ Alkoxycarbonyl is a radical of the formula RO—C(O)—, wherein R is an alkyl radical having from 1 to 6 carbon atoms as defined above. Examples comprise methyloxycarbonyl, ethyloxycarbonyl, propyloxycarbonyl, isopropyloxycarbonyl and the like.

$C_1$-$C_6$ Alkylthio (also termed as $C_1$-$C_6$ alkylsulfanyl) is a radical of the formula R—S—, wherein R is an alkyl radical having from 1 to 6 carbon atoms as defined above. Examples comprise methylthio, ethylthio, propylthio, butylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropyl and 1-ethyl-2-methylpropyl.

$C_1$-$C_6$ Alkylsulfinyl is a radical of the formula R—S(O)—, wherein R is an alkyl radical having from 1 to 6 carbon atoms as defined above. Examples comprise methylsulfinyl, ethylsulfinyl, propylsulfinyl, butylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, hexylsulfinyl, 1,1-dimethylpropylsulfinyl, 1,2-dimethylpropylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropyl and 1-ethyl-2-methylpropyl.

$C_1$-$C_6$ Alkylsulfonyl is a radical of the formula R—S(O)$_2$—, wherein R is an alkyl radical having from 1 to 6 carbon atoms as defined above. Examples comprise methylsulfonyl, ethylsulfonyl, propylsulfonyl, butylsulfonyl, pentylsulfonyl, 1-methylbutylsulfonyl, 2-methylbutylsulfonyl, 3-methylbutylsulfonyl, 2,2-dimethylpropylsulfonyl, 1-ethylpropylsulfonyl, hexylsulfonyl, 1,1-dimethylpropylsulfonyl, 1,2-dimethylpropylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropyl and 1-ethyl-2-methylpropyl.

Fluorinated $C_1$-$C_6$ alkylcarbonyl is a radical of the formula R—C(O)—, wherein R is a fluorinated alkyl radical having from 1 to 6 carbon atoms as defined above. Examples comprise fluoroacetyl, difluoroacetyl, trifluoroacetyl, (R)-1-fluoroethylcarbonyl, (S)-1-fluoroethylcarbonyl, 2-fluoroethylcarbonyl, 1,1-difluoroethylcarbonyl, 2,2-difluoroethylcarbonyl, 2,2,2-trifluoroethylcarbonyl, (R)-1-fluoropropylcarbonyl, (S)-1-fluoropropylcarbonyl, 2-fluoropropylcarbonyl, 3-fluoropropylcarbonyl, 1,1-difluoropropylcarbonyl, 2,2-difluoropropylcarbonyl, 3,3-difluoropropylcarbonyl, 3,3,3-trifluoropropylcarbonyl, (R)-2-fluoro-1-methylethylcarbonyl, (S)-2-fluoro-1-methylethylcarbonyl, (R)-2,2-difluoro-1-methylethylcarbonyl, (S)-2,2-difluoro-1-methylethylcarbonyl, (R)-1,2-difluoro-1-methylethylcarbonyl, (S)-1,2-difluoro-1-methylethylcarbonyl, (R)-2,2,2-trifluoro-1-methylethylcarbonyl, (S)-2,2,2-trifluoro-1-methylethylcarbonyl, 2-fluoro-1-(fluoromethyl)ethylcarbonyl, 1-(difluoromethyl)-2,2-difluoroethylcarbonyl, (R)-1-fluorobutylcarbonyl, (S)-1-fluorobutylcarbonyl, 2-fluorobutylcarbonyl, 3-fluorobutylcarbonyl, 4-fluorobutylcarbonyl, 1,1-difluorobutylcarbonyl, 2,2-difluorobutylcarbonyl, 3,3-difluorobutylcarbonyl, 4,4-difluorobutylcarbonyl, 4,4,4-trifluorobutylcarbonyl, etc.

Fluorinated $C_1$-$C_6$ alkylcarbonylamino is a radical of the formula R—C(O)—NH—, wherein R is a fluorinated alkyl radical having from 1 to 6 carbon atoms as defined above. Examples comprise fluoroacetamido, difluoroacetamido, trifluoroacetamido, (R)-1-fluoroethylcarbonylamino, (S)-1-fluoroethylcarbonylamino, 2-fluoroethylcarbonylamino, 1,1-difluoroethylcarbonylamino, 2,2-difluoroethylcarbonylamino, 2,2,2-trifluoroethylcarbonylamino, (R)-1-fluoropropylcarbonylamino, (S)-1-fluoropropylcarbonylamino, 2-fluoropropylcarbonylamino, 3-fluoropropylcarbonylamino, 1,1-difluoropropylcarbonylamino, 2,2-difluoropropylcarbonylamino, 3,3-difluoropropylcarbonylamino, 3,3,3-trifluoropropylcarbonylamino, (R)-2-fluoro-1-methylethylcarbonylamino, (S)-2-fluoro-1-methylethylcarbonylamino, (R)-2,2-difluoro-1-methylethylcarbonylamino, (S)-2,2-difluoro-1-methylethylcarbonylamino, (R)-1,2-difluoro-1-methylethylcarbonylamino, (S)-1,2-difluoro-1-methylethylcarbonylamino, (R)-2,2,2-trifluoro-1-methylethylcarbonylamino, (S)-2,2,2-trifluoro-1-methylethylcarbonylamino, 2-fluoro-1-(fluoromethyl)ethylcarbonylamino, 1-(difluoromethyl)-2,2-difluoroethylcarbonylamino, (R)-1-fluorobutylcarbonylamino, (S)-1-fluorobutylcarbonylamino, 2-fluorobutylcarbonylamino, 3-fluorobutylcarbonylamino, 4-fluorobutylcarbonylamino, 1,1-difluorobutylcarbonylamino, 2,2-difluorobutylcarbonylamino, 3,3-difluorobutylcarbonylamino, 4,4-difluorobutylcarbonylamino, 4,4,4-trifluorobutylcarbonylamino, etc.

Fluorinated $C_1$-$C_6$ alkylcarbonyloxy is a radical of the formula R—C(O)—O—, wherein R is a fluorinated alkyl radical having from 1 to 6 carbon atoms as defined above fluoroacetyl, difluoroacetyl, trifluoroacetyl, (R)-1-fluoroethylcarbonyloxy, (S)-1-fluoroethylcarbonyloxy, 2-fluoroethylcarbonyloxy, 1,1-difluoroethylcarbonyloxy, 2,2-difluoroethylcarbonyloxy, 2,2,2-trifluoroethylcarbonyloxy, (R)-1-fluoropropylcarbonyloxy, (S)-1-fluoropropylcarbonyloxy, 2-fluoropropylcarbonyloxy, 3-fluoropropylcarbonyloxy, 1,1-difluoropropylcarbonyloxy, 2,2-difluoropropylcarbonyloxy, 3,3-difluoropropylcarbonyloxy, 3,3,3-trifluoropropylcarbonyloxy, (R)-2-fluoro-1-methylethylcarbonyloxy, (S)-2-fluoro-1-methylethylcarbonyloxy, (R)-2,2-difluoro-1-methylethylcarbonyloxy, (S)-2,2-difluoro-1-methylethylcarbonyloxy, (R)-1,2-difluoro-1-methylethylcarbonyloxy, (S)-1,2-difluoro-1-methylethylcarbonyloxy, (R)-2,2,2-trifluoro-1-methylethylcarbonyloxy, (S)-2,2,2-trifluoro-1-methylethylcarbonyloxy, 2-fluoro-1-(fluoromethyl)ethylcarbonyloxy, 1-(difluoromethyl)-2,2-difluoroethylcarbonyloxy, (R)-1-fluorobutylcarbonyloxy, (S)-1-fluorobutylcarbonyloxy, 2-fluorobutylcarbonyloxy, 3-fluorobutylcarbonyloxy, 4-fluorobutylcarbonyloxy, 1,1-difluorobutylcarbonyloxy, 2,2-difluorobutylcarbonyloxy, 3,3-difluorobutylcarbonyloxy, 4,4-difluorobutylcarbonyloxy, 4,4,4-trifluorobutylcarbonyloxy, etc.

Fluorinated $C_1$-$C_6$ alkylthio (also termed as fluorinated $C_1$-$C_6$-alkylsulfanyl) is a radical of the formula R—S—, wherein R is a fluorinated alkyl radical having from 1 to 6 carbon atoms as defined above. Examples comprise fluoromethylthio, difluoromethylthio, trifluoromethylthio, (R)-1-fluoroethylthio, (S)-1-fluoroethylthio, 2-fluoroethylthio, 1,1-difluoroethylthio, 2,2-difluoroethylthio, 2,2,2-trifluoroethylthio, (R)-1-fluoropropylthio, (S)-1-fluoropropylthio, 2-fluoropropylthio, 3-fluoropropylthio, 1,1-difluoropropylthio, 2,2-difluoropropylthio, 3,3-difluoropropylthio, 3,3,3-trifluoropropylthio, (R)-2-fluoro-1-methylethylthio, (S)-2-fluoro-1-methylethylthio, (R)-2,2-difluoro-1-methylethylthio, (S)-2,2-difluoro-1-methylethylthio, (R)-1,2-difluoro-1-methylethylthio, (S)-1,2-difluoro-1-methylethylthio, (R)-2,2,2-trifluoro-1-methylethylthio, (S)-2,2,2-trifluoro-1-methylethylthio, 2-fluoro-1-(fluoromethyl)ethylthio, 1-(difluoromethyl)-2,2-difluoroethylthio, (R)-1-fluorobutylthio, (S)-1-fluorobutylthio, 2-fluorobutylthio, 3-fluorobutylthio, 4-fluorobutylthio, 1,1-difluorobutylthio, 2,2-difluorobutylthio, 3,3-difluorobutylthio, 4,4-difluorobutylthio, 4,4,4-trifluorobutylthio, etc.

Fluorinated $C_1$-$C_6$ alkylsulfinyl is a radical of the formula R—S(O)—, wherein R is a fluorinated alkyl radical having from 1 to 6 carbon atoms as defined above. Examples comprise fluoromethylsulfinyl, difluoromethylsulfinyl, trifluoromethylsulfinyl, (R)-1-fluoroethylsulfinyl, (S)-1-fluoroethylsulfinyl, 2-fluoroethylsulfinyl, 1,1-difluoroethylsulfinyl, 2,2-difluoroethylsulfinyl, 2,2,2-trifluoroethylsulfinyl, (R)-1-fluoropropylsulfinyl, (S)-1-fluoropropylsulfinyl, 2-fluoropropylsulfinyl, 3-fluoropropylsulfinyl, 1,1-difluoropropylsulfinyl, 2,2-difluoropropylsulfinyl, 3,3-difluoropropylsulfinyl, 3,3,3-trifluoropropylsulfinyl, (R)-2-fluoro-1-methylethylsulfinyl, (S)-2-fluoro-1-methylethylsulfinyl, (R)-2,2-difluoro-1-methylethylsulfinyl, (S)-2,2-difluoro-1-methylethylsulfinyl, (R)-1,2-difluoro-1-methylethylsulfinyl, (S)-1,2-difluoro-1-methylethylsulfinyl, (R)-2,2,2-trifluoro-1-methylethylsulfinyl, (S)-2,2,2-trifluoro-1-methylethylsulfinyl, 2-fluoro-1-(fluoromethyl)ethylsulfinyl, 1-(difluoromethyl)-2,2-difluoroethylsulfinyl, (R)-1-fluorobutylsulfinyl, (S)-1-fluorobutylsulfinyl, 2-fluorobutylsulfinyl, 3-fluorobutylsulfinyl, 4-fluorobutylsulfinyl, 1,1-difluorobutylsulfinyl, 2,2-difluorobutylsulfinyl, 3,3-difluorobutylsulfinyl, 4,4-difluorobutylsulfinyl, 4,4,4-trifluorobutylsulfinyl, etc.

Fluorinated $C_1$-$C_6$ alkylsulfonyl is a radical of the formula R—S(O)$_2$—, wherein R is a fluorinated alkyl radical having from 1 to 6 carbon atoms as defined above. Examples comprise fluoroethylsulfonyl, difluoromethylsulfonyl, trifluoromethylsulfonyl, (R)-1-fluoroethylsulfonyl, (S)-1-fluoroethylsulfonyl, 2-fluoroethylsulfonyl, 1,1-difluoroethylsulfonyl, 2,2-difluoroethylsulfonyl, 2,2,2-trifluoroethylsulfonyl, (R)-1-fluoropropylsulfonyl, (S)-1-fluoropropylsulfonyl, 2-fluoropropylsulfonyl, 3-fluoropropylsulfonyl, 1,1-difluoropropylsulfonyl, 2,2-difluoropropylsulfonyl, 3,3-difluoropropylsulfonyl, 3,3,3-trifluoropropylsulfonyl, (R)-2-fluoro-1-methylethylsulfonyl, (S)-2-fluoro-1-methylethylsulfonyl, (R)-2,2-difluoro-1-methylethylsulfonyl, (S)-2,2-difluoro-1-methylethylsulfonyl, (R)-1,2-difluoro-1-methylethylsulfonyl, (S)-1,2-difluoro-1-methylethylsulfonyl, (R)-2,2,2-trifluoro-1-methylethylsulfonyl, (S)-2,2,2-trifluoro-1-methylethylsulfonyl, 2-fluoro-1-(fluoromethyl)ethylsulfonyl, 1-(difluoromethyl)-2,2-difluoroethylsulfonyl, (R)-1-fluorobutylsulfonyl, (S)-1-fluorobutylsulfonyl, 2-fluorobutylsulfonyl, 3-fluorobutylsulfonyl, 4-fluorobutylsulfonyl, 1,1-difluorobutylsulfonyl, 2,2-difluorobutylsulfonyl, 3,3-difluorobutylsulfonyl, 4,4-difluorobutylsulfonyl, 4,4,4-trifluorobutylsulfonyl, etc.

$C_3$-$C_6$ Cycloalkyl is a cycloaliphatic radical having from 3 to 6 C atoms, such as cyclopropyl, cyclobutyl and cyclopentyl. The cycloalkyl radical may be unsubstituted or may carry 1, 2, 3 or 4 $C_1$-$C_4$ alkyl radicals, preferably a methyl radical.

One alkyl radical is preferably located in the 1-position of the cycloalkyl radical, such as in 1-methylcyclopropyl or 1-methylcyclobutyl.

Fluorinated $C_3$-$C_6$ cycloalkyl is a cycloaliphatic radical having from 3 to 6 C atoms, such as cyclopropyl, cyclobutyl and cyclopentyl, wherein at least one, e.g. 1, 2, 3, 4 or all of the hydrogen atoms are replaced by a fluorine atoms such as in 1-fluorocyclopropyl, 2-fluorocyclopropyl, 2,2-difluorocyclopropyl, 1,2-difluorocyclopropyl, 2,3-difluorocyclopropyl, pentafluorocyclopropyl, 1-fluorocyclobutyl, 2-fluorocyclobutyl, 3-fluorocyclobutyl, 2,2-difluorocyclobutyl, 3,3-difluorocyclobutyl, 1,2-difluorocyclobutyl, 1,3-difluorocyclobutyl, 2,3-difluorocyclobutyl, 2,4-difluorocyclobutyl, or 1,2,2-trifluorocyclobutyl.

$C_2$-$C_6$-Alkenyl is a singly unsaturated hydrocarbon radical having 2, 3, 4, 5 or 6 C-atoms, e.g. vinyl, allyl(2-propen-1-yl), 1-propen-1-yl, 2-propen-2-yl, methallyl(2-methylprop-2-en-1-yl) and the like. $C_3$-$C_4$-Alkenyl is, in particular, allyl, 1-methylprop-2-en-1-yl, 2-buten-1-yl, 3-buten-1-yl, methallyl, 2-penten-1-yl, 3-penten-1-yl, 4-penten-1-yl, 1-methylbut-2-en-1-yl or 2-ethylprop-2-en-1-yl.

Fluorinated $C_2$-$C_6$-alkenyl is a singly unsaturated hydrocarbon radical having 2, 3, 4, 5 or 6 C-atoms, I, wherein at least one, e.g. 1, 2, 3, 4 or all of the hydrogen atoms are replaced by a fluorine atoms such as in 1-fluorovinyl, 2-fluorovinyl, 2,2-fluorovinyl, 3,3,3-fluoropropenyl, 1,1-difluoro-2-propenyl 1-fluoro-2-propenyl etc.

3- to 7-membered heterocyclic radicals comprise saturated heterocyclic radicals, which generally have 3-, 4-, 5-, 6- or 7 ring-forming atoms (ring members), unsaturated non-aromatic heterocyclic radicals, which generally have 5-, 6- or 7 ring forming atoms, and heteroaromatic radicals, which generally have 5-, 6- or 7 ring forming atoms. The heterocylcic radicals may be bound via a carbon atom (C-bound) or an nitrogen atom (N-bound). Preferred heterocyclic radicals comprise 1 nitrogen atom as ring member atom and optionally 1, 2 or 3 further heteroatoms as ring members, which are selected, independently of each other from O, S and N. Likewise preferred heterocyclic radicals comprise 1 heteroatom as ring member, which is selected from O, S and N, and optionally 1, 2 or 3 further nitrogen atoms as ring members. The heterocyclic radicals may also comprise 1 to 3 heteroatom-containing groups as ring members, like CO, SO and $SO_2$. Examples therefore are the below-mentioned oxo-containing heterocycles.

Examples of 3- to 7-membered, saturated heterocyclic radicals comprise 1- or 2-aziridinyl, 1-, 2- or 3-azetidinyl, 1-, 2- or 3-pyrrolidinyl, 2- or 3-oxopyrrolidinyl, 1-, 2-, 3- or 4-piperidinyl, 2-, 3- or 4-morpholinyl, 2-, 3- or 4-thiomorpholinyl, 1-oxo-thiomorpholinyl, 1,1-dioxothiomorpholinyl, 1-, 2- or 3-piperazinyl, 2-, 3-4- or 5-oxazolidinyl, 2-, 4- or 5-oxo-oxazolidinyl, 2-, 3-, 4- or 5-isoxazolidinyl, 2-oxiranyl, 2- or 3-oxetanyl, 2- or 3-oxolanyl, 2-, 3- or 4-oxanyl, 1,3-dioxolan-2- or 4-yl and the like, which may be unsubstituted or which may carry 1, 2 or 3 of the aforementioned radicals $R^a$ and/or hydroxy.

Unsaturated non-aromatic heterocyclic radicals are heterocyclic radicals which generally have 5-, 6- or 7 ring-forming atoms and which have 1 or 2 double bonds that do not form an aromatic π-electron system. Examples are 2,3-dihydropyrrolyl, 3,4-dihydropyrrolyl, 2,3-dihydrofuranyl, 3,4-dihydrofuranyl, 2,3-dihydrothiophenyl, 3,4-dihydrothiophenyl, 1,2-dihydropyridinyl, 2,3-Dihydropyridinyl, 3,4-dihydropyridinyl, 1,2,3,4-tetrahydropyridinyl, 2,3,4,5-tetrahydropyridinyl, and the like.

5- or 6-membered heteroaromatic radicals are heteroaromatic cyclic radicals, wherein the cyclic radical has 5 or 6 atoms which form the ring (ring members) and wherein generally 1, 2, 3 or 4 ring member atoms are selected from O, S and N, the other ring member atoms being carbon atoms. The heteroaromatic radicals may be bound via a carbon atom (C-bound) or an nitrogen atom (N-bound). Preferred heteroaromatic radicals comprise 1 nitrogen atom as ring member atom and optionally 1, 2 or 3 further heteroatoms as ring members, which are selected, independently of each other from O, S and N. Likewise preferred heteroaromatic radicals comprise 1 heteroatom as ring member, which is selected from O, S and N, and optionally 1, 2 or 3 further nitrogen atoms as ring members. Examples of 5- or 6-membered heteroaromatic radicals comprise 2-, 3-, or 4-pyridyl, 2-, 4- or 5-pyrimidinyl, pyrazinyl, 3- or 4-pyridazinyl, 2- or 3-thienyl, 2- or 3-furyl, 1-, 2- or 3-pyrrolyl, 1-, 2- or 4-imidazolyl, 1-, 3- or 4-pyrazolyl, 1- or 3-[1,2,4]-triazolyl, 1- or 4-[1,2,3]-triazolyl, 1-, 2- or 5-tetrazolyl, 2-, 3- or 5-oxazolyl, 3-, 4- or 5-isoxazolyl, 2-, 3- or 5-thiazolyl, 3-, 4- or 5-isothiazolyl, 4- or 5-[1,2,3]-oxadiazolyl, [1,2,5]-oxadiazolyl(=furazanyl), 3- or 5-[1,2,4]-oxadizolyl, [1,3,4]-oxadizolyl, 4- or 5-[1,2,3]-thiadiazolyl, [1,2,5]-thiadiazolyl, 3- or 5-[1,2,4]-thiadizolyl or [1,3,4]-thiadiazolyl, which may be unsubstituted or which may carry 1, 2 or 3 of the aforementioned radicals $R^a$ and/or hydroxy.

Examples of a phenyl ring fused to a saturated or unsaturated 5- or 6-membered carbocyclic or heterocyclic ring comprise indenyl, indanyl, naphthyl, 1,2- or 2,3-dihydronaphthyl, tetralin, benzofuranyl, 2,3-dihydrobenzofuranyl, benzothienyl, indolyl, indazolyl, benzimidazolyl, benzoxathiazolyl, benzoxadiazolyl, benzothiadiazolyl, benzoxazinyl, dihydrobenzoxazinyl, chinolinyl, isochinolinyl, tetrahydroisochinolinyl, chromenyl, chromanyl and the like, which may be unsubstituted or which may carry 1, 2 or 3 of the aforementioned radicals $R^a$. This fused system may be bonded to the remainder of the molecule (more precisely to the sulfonyl group) via carbon atoms of the phenyl moiety or via ring atoms (C- or N-atoms) of the ring fused to phenyl.

If $R^6$ and $R^7$ form together with N a 4-, 5- or 6-membered ring, examples for this type of radical comprise, apart from the above-defined 5- or 6-membered heteroaromatic radicals containing at least one N atom as ring member, the N-atom further being bound to Ar (like in pyrrol-1-yl, pyrazol-1-yl, imidazol-1-yl, [1,2,3]-triazol-1-yl and the like), azetidinyl, azetinyl, pyrrolinyl, pyrrolidinyl, pyrazolinyl, pyrazolidinyl, imidazolinyl, imidazolidinyl, oxazolinyl, oxazolidinyl, piperidinyl, piperazinyl, morpholinyl and the like.

A skilled person will appreciate that the radical -E-$SO_2$-Ar may be bound to any of the carbon atoms of the phenyl part of the bicyclic moiety in formula I, thereby substituting a hydrogen atom. Specifically, the radical -E-$SO_2$—Ar is bound to a carbon atom, which is not adjacent to a bridgehead carbon atom of the bicyclic moiety. A skilled person will further appreciate that for Y being $CHR^{2a}CH_2$ or $CHR^{2a}CH_2CH_2$ the $CHR^{2a}$ moiety is attached to the carbon atom that carries the $CH_2NR^1R^{1a}$ radical. Similarly, for X being $CHR^2CH_2$ the $CHR^2$ moiety is attached to the carbon atom that carries the $CH_2NR^1R^{1a}$ radical. A skilled person will also appreciate that for X being N or C—$R^2$ the ≔ indicates a double bond while for X being N—$R^2$, $CHR^2$ or $CHR^2CH_2$ the ---- indicates a single bond. A skilled person will also appreciate that for X being absent, i.e. a covalent bond, the carbon atom, to which $CH_2$—$NR^1R^{1a}$ is bound, is linked to the benzene ring via a covalent (single) bond.

In a specific embodiment, the compounds of the invention are compounds of formula (I.1)

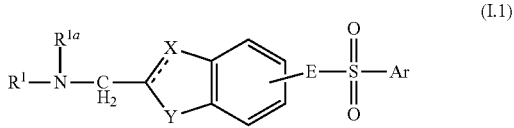

(I.1)

wherein

Ar is phenyl or an aromatic 5- or 6-membered C-bound heteroaromatic radical, comprising 1 nitrogen atom as ring member and 0, 1, 2 or 3 further heteroatoms, independently of each other, selected from O, S and N, as ring members, wherein Ar may carry 1, 2 or 3 radicals $R^a$ which are, independently of each other, selected from the group consisting of halogen, $C_1$-$C_6$-alkyl, $C_3$-$C_6$-cycloalkyl, $C_1$-$C_6$-alkoxy, fluorinated $C_1$-$C_6$-alkyl, fluorinated $C_3$-$C_6$-cycloalkyl, fluorinated $C_1$-$C_6$-alkoxy, $NR^4R^5$, 1-aziridinyl, azetidin-1-yl, pyrrolidin-1-yl or piperidin-1-yl, wherein the last four mentioned radicals may be fluorinated, a phenyl group and an aromatic 5- or 6-membered C-bound heteroaromatic radical, comprising 1 nitrogen atom as ring member and 0, 1, 2 or 3 further heteroatoms, independently of each other, selected from O, S and N, wherein the last two mentioned radicals may carry 1, 2, 3 or 4 radicals selected from Halogen and the radicals $R^a$;

$R^4$, $R^5$ independently of each other are selected from H, $C_1$-$C_2$-alkyl and fluorinated $C_1$-$C_2$-alkyl;

and X, Y, ----- E, $R^1$, $R^{1a}$, $R^2$, $R^{2a}$ and $R^3$ are as defined above.

Preferably, Ar is phenyl or an aromatic 5- or 6-membered C-bound heteroaromatic radical, comprising 1 nitrogen atom as ring member and 0, 1, 2 or 3 further heteroatoms, independently of each other, selected from O, S and N, as ring members which may be unsubstituted or which may carry 1, 2 or 3 of the aforementioned radicals $R^a$ and/or $R^b$. Amongst these heteroaromatic radicals those are preferred, which comprise 1, 2 or 3 nitrogen atoms and no further heteroatom as ring members, or 1 or 2 nitrogen atoms and 1 atom, selected from O and S, as ring members. However, thienyl and furyl are likewise preferred. Particularly preferred radicals Ar are 2- or 3-thienyl, 2-, 3- or 4-pyridyl, 2-, 4- or 5-pyrimidinyl, 2-, 3- or 5-thiazolyl, 1,2,4-triazol-3-yl, 1,2,3-triazol-4-yl, 1,3,4-thiadiazol-2-yl, in particular 2-thienyl, 2-pyrimidinyl, 5-pyrimidinyl, 2-pyridinyl and more particularly phenyl which may be unsubstituted or which may carry 1, 2 or 3 of the aforementioned radicals $R^a$.

Preferred radicals Ar are phenyl, 2- or 3-thienyl, 2-, 3- or 4-pyridyl, 2-, 4- or 5-pyrimidinyl, 2-, 3-or 5-thiazolyl, 1,2,4-triazol-3-yl, 1,2,3-triazol-4-yl, 1,3,4-thiadiazol-2-yl, in particular phenyl, 2-thienyl, 2-pyrimidinyl, 5-pyrimidinyl, 2-pyridinyl and more particularly phenyl.

Preferably the aromatic radical Ar carries one radical $R^a$ and optionally one or two further radicals $R^b$ selected from CN, OH, methyl, fluorinated methyl, halogen, in particular fluorine or chlorine.

The aforementioned 5-membered heteroaromatic radicals Ar carry preferably one radical $R^a$ in the 3-position (related to the position of the $SO_2$-radical) and optionally one or two further radicals $R^b$, which are preferably selected from halogen, in particular fluorine or chlorine.

Phenyl and the aforementioned 6-membered heteroaromatic radicals Ar preferably carry one radical $R^a$ in the 4-position (related to the position of the $SO_2$-radical) and optionally one or two further radicals $R^b$, which are preferably selected from halogen, in particular fluorine or chlorine.

In one preferred embodiment of the invention Ar is phenyl that carries a radical $R^a$ in the 4-position of the phenyl ring and optionally 1 or 2 further radicals $R^b$, which are preferably selected from halogen, in particular from fluorine or chlorine. More preferably, Ar is phenyl that carries a radical $R^a$ in the 4-position of the phenyl ring and no further radical.

In another preferred embodiment of the invention Ar is 2-pyrimidinyl that carries a radical $R^a$ in the 5-position of the pyrimidine ring and optionally 1 or 2 further radicals $R^b$, which are preferably selected from halogen, in particular from fluorine or chlorine.

In another preferred embodiment of the invention Ar is 5-pyrimidinyl that carries a radical $R^a$ in the 2-position of the pyrimidine ring and optionally 1 or 2 further radicals $R^b$, which are preferably selected from halogen, in particular from fluorine or chlorine.

In another preferred embodiment of the invention Ar is 2-thienyl that carries a radical $R^a$ in the 3-position of the thiophene ring and optionally 1 or 2 further radicals $R^b$, which are preferably selected from halogen, in particular from fluorine or chlorine.

In another preferred embodiment of the invention, Ar is phenyl, which is fused to a 5-or 6-membered heterocyclic or carbocyclic ring as described above and which is unsubstituted or which may carry 1, 2 or 3 radicals $R^a$ as given above. Preferably, this fused system is selected from indenyl, indanyl, naphthyl, tetralin, benzofuranyl, 2,3-dihydrobenzofuranyl, benzothienyl, indolyl, indazolyl, benzimidazolyl, benzoxathiazolyl, benzoxadiazolyl, benzothiadiazolyl, benzoxazinyl, dihydrobenzoxazinyl, chinolinyl, isochinolinyl, tetrahydroisochinolinyl, chromenyl, chromanyl and the like, which may be unsubstituted or which may carry 1, 2 or 3 of the aforementioned radicals $R^a$. Preferred substituents $R^a$ for this fused system are selected from halogen, $C_1$-$C_4$-alkyl, fluorinated $C_1$-$C_4$-alkyl, $C_1$-$C_4$-alkoxy, fluorinated $C_1$-$C_4$-alkoxy, $C_1$-$C_4$-alkylcarbonyl and fluorinated $C_1$-$C_4$-alkylcarbonyl. More preferred substituents $R^a$ for this fused system are selected from halogen, $C_1$-$C_4$-alkyl and fluorinated $C_1$-$C_4$-alkylcarbonyl.

In a more preferred embodiment of the invention, Ar is phenyl. Preferably, Ar is phenyl that carries a radical $R^a$ in the 4-position of the phenyl ring and optionally 1 or 2 further radicals $R^b$, which are preferably selected from halogen, in particular from fluorine or chlorine. More preferably, Ar is phenyl that carries a radical $R^a$ in the 4-position of the phenyl ring and no further radical.

In one preferred embodiment, the radical Ar carries one radical $R^a$, which has the formula $R^{a'}$.

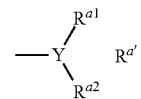

wherein

Y is N, CH or CF, $R^{a1}$ and $R^{a2}$ are independently of each other selected from $C_1$-$C_2$-alkyl, in particular methyl, fluorinated $C_1$-$C_2$-alkyl, in particular fluoromethyl, difluoromethyl or trifluoromethyl, provided for Y being CH or CF one of the radicals $R^{a1}$ or $R^{a2}$ may also be hydrogen or fluorine, or $R^{a1}$ and $R^{a2}$ form a radical $(CH_2)_m$ wherein 1 or 2 of the hydrogen atoms may be replaced by fluorine, hydroxy, oxo, $C_1$-$C_2$-alkyl or $C_1$-$C_2$-alkoxy, wherein one $CH_2$ moiety may be replaced by O, S, S=O, $SO_2$ or N—$R^c$, $R^c$ being hydrogen or $C_1$-$C_2$-alkyl and wherein m is 2, 3, 4, 5 or 6, preferably 2, 3 or 4, in particular $CH_2$—$CH_2$, CHF—$CH_2$ $CF_2$—$CH_2$, $CH_2$—$CH_2$—$CH_2$, CHF—$CH_2$—$CH_2$, $CF_2$—$CH_2$—$CH_2$, $CH_2$—CHF—$CH_2$, $CH_2$—$CF_2$—$CH_2$.

In case $R^{a1}$ and $R^{a2}$ form a radical $(CH_2)_m$ it is preferred that 1 or 2 of the hydrogen atoms may be replaced by fluorine. Examples therefore are $CH_2$—$CH_2$, CHF—$CH_2$—$CF_2$—$CH_2$, $CH_2$—$CH_2$—$CH_2$, CHF—$CH_2$—$CH_2$, $CF_2$—$CH_2$—$CH_2$, $CH_2$—CHF—$CH_2$, and $CH_2$—$CF_2$—$CH_2$.

In case $R^{a1}$ and $R^{a2}$ are different from each other, the radical of the aforementioned formula $R^a$ may have either (R)- or (S)-configuration with regard to the Y-moiety.

Examples for preferred radicals of the formula $R^{a'}$ comprise isopropyl, (R)-1-fluoroethyl, (S)-1-fluoroethyl, 2-fluoroethyl, 1,1-difluoroethyl, 2,2-difluoroethyl, 2,2,2-trifluoroethyl, (R)-1-fluoropropyl, (S)-1-fluoropropyl, (R)-2-fluoropropyl, (S)-2-fluoropropyl, 3-fluoropropyl, 1,1-difluoropropyl, 2,2-difluoropropyl, 3,3-difluoropropyl, 3,3,3-trifluoropropyl, (R)-2-fluoro-1-methylethyl, (S)-2-fluoro-1-methylethyl, (R)-2,2-difluoro-1-methylethyl, (S)-2,2-difluoro-1-methylethyl, (R)-1,2-difluoro-1-methylethyl, (S)-1,2-difluoro-1-methylethyl, (R)-2,2,2-trifluoro-1-methylethyl, (S)-2,2,2-trifluoro-1-methylethyl, 2-fluoro-1-(fluoromethyl)ethyl, 1-(difluoromethyl)-2,2-difluoroethyl, cyclopropyl, cyclobutyl, 1-fluorocyclopropyl, (R)- and (S)-2,2-difluorocyclopropyl, (R)- and (S)-2-fluorocyclopropyl.

Amongst the radicals of the formula $R^{a'}$ those are preferred which carry 1, 2, 3 or 4, in particular 1, 2 or 3 fluorine atoms.

Examples for alternatively preferred radicals of the formula $R^{a'}$ comprise 4-morpholinyl, 4-thiomorpholinyl, 4-(1,1-dioxo)thiomorpholinyl, piperazin-1-yl, 4-methylpiperazin-1-yl, azetidin-1-yl, 2-methylazetidin-1-yl, (S)-2-methylazetidin-1-yl, (R)-2-methylazetidin-1-yl, 3-fluoroazetidin-1-yl, 3-methoxyazetidin-1-yl, 3-hydroxyazetidin-1-yl, pyrrolidin-1-yl, pyrrolidin-2-yl, (S)-pyrrolidin-2-yl, (R)-pyrrolidin-2-yl, pyrrolidin-3-yl, (S)-pyrrolidin-3-yl, (R)-pyrrolidin-3-yl, 2-fluoropyrrolidin-1-yl, (S)-2-fluoropyrrolidin-1-yl, (R)-2-fluoropyrrolidin-1-yl, 3-fluoropyrrolidin-1-yl, (S)-3-fluoropyrrolidin-1-yl, (R)-3-fluoropyrrolidin-1-yl, 2,2-difluoropyrrolidin-1-yl, 3,3-difluoropyrrolidin-1-yl, 2-methylpyrrolidin-1-yl, (S)-2-methylpyrrolidin-1-yl, (R)-2-methylpyrrolidin-1-yl, 3-methylpyrrolidin-1-yl, (S)-3-methylpyrrolidin-1-yl, (R)-3-methylpyrrolidin-1-yl, 1-methylpyrrolidin-2-yl, (S)-1-methylpyrrolidin-2-yl, (R)-1-methylpyrrolidin-2-yl, 1-methylpyrrolidin-3-yl, (S)-1-methylpyrrolidin-3-yl, (R)-1-methylpyrrolidin-3-yl, 2,2-dimethylpyrrolidin-1-yl, 3,3-dimethylpyrrolidin-1-yl, 2-trifluoromethylpyrrolidin-1-yl, (S)-2-trifluoromethylpyrrolidin-1-yl, (R)-2-trifluoromethylpyrrolidin-1-yl, 3-trifluoromethylpyrrolidin-1-yl, (S)-3-trifluoromethylpyrrolidin-1-yl, (R)-3-trifluoromethylpyrrolidin-1-yl, 2-oxopyrrolidin-1-yl, 2-oxooxazolidin-3-yl, piperidin-1-yl, 2-methylpiperidin-1-yl, (S)-2-methylpiperidin-1-yl and (R)-2-methylpiperidin-1-yl.

More preferably, $R^{a'}$ is selected from isopropyl and fluorinated isopropyl, like (R)-2-fluoro-1-methylethyl, (S)-2-fluoro-1-methylethyl, (R)-2,2-difluoro-1-methylethyl, (S)-2,2-difluoro-1-methylethyl, (R)-1,2-difluoro-1-methylethyl, (S)-1,2-difluoro-1-methylethyl, (R)-2,2,2-trifluoro-1-methylethyl, (S)-2,2,2-trifluoro-1-methylethyl, 2-fluoro-1-(fluoromethyl)ethyl and 1-(difluoromethyl)-2,2-difluoroethyl.

In another preferred embodiment Ar carries one radical $R^a$, which is selected from 5- or 6-membered heteroaromatic radicals having as ring members 1 heteroatom selected from O, S and N and which may further have 1, 2 or 3 nitrogen atoms as ring members, and wherein the 5- or 6-membered heteroaromatic radical may carry 1, 2 or 3 substituents selected from halogen, $NO_2$, $NH_2$, OH, CN, $C_1$-$C_6$-alkyl, $C_3$-$C_6$-cycloalkyl, $C_1$-$C_6$-alkoxy, fluorinated $C_1$-$C_6$-alkyl, fluorinated $C_3$-$C_6$-cycloalkyl, fluorinated $C_1$-$C_6$-alkoxy, $C_1$-$C_6$-hydroxyalkyl, $C_1$-$C_4$-alkoxy-$C_2$-$C_4$-alkyl, $C_1$-$C_6$-hydroxyalkoxy, $C_1$-$C_4$-alkoxy-$C_2$-$C_4$-alkoxy, $C_1$-$C_6$-alkylcarbonyl, $C_1$-$C_6$-alkylamino, di-$C_1$-$C_6$-alkylamino, $C_1$-$C_6$-alkylaminocarbonyl, di-$C_1$-$C_6$-alkylaminocarbonyl, fluorinated $C_1$-$C_6$-alkylcarbonyl, $C_1$-$C_6$-alkylcarbonylamino, fluorinated $C_1$-$C_6$-alkylcarbonylamino, $C_1$-$C_6$-alkylcarbonyloxy, fluorinated $C_1$-$C_6$-alkylcarbonyloxy, $C_1$-$C_6$-alkoxycarbonyl, $C_1$-$C_6$-alkylthio, fluorinated $C_1$-$C_6$-alkylthio, $C_1$-$C_6$-alkylsulfinyl, $C_1$-$C_6$-alkylsulfonyl, fluorinated $C_1$-$C_6$-alkylsulfinyl and fluorinated $C_1$-$C_6$-alkylsulfonyl. Amongst these radicals $R^a$, preference is given to radicals selected from 2-, 3-, or 4-pyridyl, 2-, 4- or 5-pyrimidinyl, pyrazinyl, 3- or 4-pyridazinyl, 2- or 3-thienyl, 2- or 3-furyl, 1-, 2- or 3-pyrrolyl, 1-, 2- or 4-imidazolyl, 1-, 3- or 4-pyrazolyl, 1- or 3-[1,2,4]-triazolyl, 1- or 4-[1,2,3]-triazolyl, 1-, 2- or 5-tetrazolyl, 2-, 3- or 5-oxazolyl, 3-, 4- or 5-isoxazolyl, 2-, 3- or 5-thiazolyl, 3-, 4- or 5-isothiazolyl, 4- or 5-[1,2,3]-oxadiazolyl, [1,2,5]-oxadiazolyl(=furazanyl), 3- or 5-[1,2,4]-oxadizolyl, [1,3,4]-oxadizolyl, 4- or 5-[1,2,3]-thiadiazolyl, [1,2,5]-thiadiazolyl, 3- or 5-[1,2,4]-thiadiazolyl or [1,3,4]-thiadiazolyl, in particular from 2- or 3-furanyl, 2- or 3-thienyl, 1-, 2- or 3-pyrrolyl, pyrazolyl, imidazolyl, oxazolyl, isoxazolyl, 1,3,4-thiadiazolyl, 1,2,4-triazolyl, 1,2,3-triazolyl and tetrazolyl, where the heteroaromatic radical may be unsubstituted or may carry 1 to 3 substituents as given above. Preferred substituents on heteroaromatic $R^a$ are selected from halogen, $C_1$-$C_4$-alkyl, $C_1$-$C_4$-alkoxy, fluorinated $C_1$-$C_4$-alkyl and fluorinated $C_1$-$C_4$-alkoxy.

In another preferred embodiment of the invention, Ar carries 1 radical $R^a$ which selected from the group consisting of $C_1$-$C_6$-alkenyl, fluorinated $C_1$-$C_6$-alkenyl, $C_1$-$C_6$-hydroxyalkyl, $C_1$-$C_6$-alkoxy-$C_1$-$C_4$-alkyl, $C_1$-$C_6$-hydroxyalkoxy, $C_1$-$C_6$-alkoxy-$C_1$-$C_4$-alkoxy, COOH, $CH_2NR^4R^5$, $ONR^4R^5$, $NHC(O)NR^4R^5$, $C(O)NR^4R^5$, $SO_2NR^4R^5$, $C_1$-$C_6$-alkylcarbonyl, fluorinated $C_2$-$C_6$-alkylcarbonyl, $C_1$-$C_6$-alkylcarbonylamino, fluorinated $C_1$-$C_6$-alkylcarbonylamino, $C_1$-$C_6$-alkylcarbonyloxy, fluorinated $C_1$-$C_6$-alkylcarbonyloxy, $C_1$-$C_6$-alkoxycarbonyl, $C_1$-$C_6$-alkylthio, fluorinated $C_1$-$C_6$-alkylthio, $C_1$-$C_6$-alkylsulfinyl, $C_1$-$C_6$-alkylsulfonyl, fluorinated $C_1$-$C_6$-alkylsulfinyl, fluorinated $C_1$-$C_6$-alkylsulfonyl, phenylsulfonyl, phenoxy, benzyloxy and a 5-or 6-membered N-bound heteroaromatic radical, wherein the four last mentioned radicals may carry 1, 2, 3 or 4 radicals selected from halogen, $NO_2$, —$NH_2$, OH, CN, $C_1$-$C_6$-alkyl, $C_3$-$C_6$-cycloalkyl, $C_1$-$C_6$-alkoxy, fluorinated $C_1$-$C_6$-alkyl, fluorinated $C_3$-$C_6$-cycloalkyl, fluorinated $C_1$-$C_6$-alkoxy, $C_1$-$C_6$-hydroxyalkyl, $C_1$-$C_4$-alkoxy-$C_2$-$C_4$-alkyl, $C_1$-$C_6$-hydroxyalkoxy, $C_1$-$C_4$-alkoxy-$C_2$-$C_4$-alkoxy, $C_1$-$C_6$-alkylcarbonyl, $C_1$-$C_6$-alkylamino, di-$C_1$-$C_6$-alkylamino, $C_1$-$C_6$-alkylaminocarbonyl, di-$C_1$-$C_6$-alkylaminocarbonyl, fluorinated $C_1$-$C_6$-alkylcarbonyl, $C_1$-$C_6$-alkylcarbonylamino, fluorinated $C_1$-$C_6$-alkylcarbonylamino, $C_1$-$C_6$-alkylcarbonyloxy, fluorinated $C_1$-$C_6$-alkylcarbonyloxy, $C_1$-$C_6$-alkoxycarbonyl, $C_1$-$C_6$-alkylthio, fluorinated $C_1$-$C_6$-alkylthio, $C_1$-$C_6$-alkylsulfonyl, fluorinated $C_1$-$C_6$-alkylsulfinyl and fluorinated $C_1$-$C_6$-alkylsulfonyl.

In another preferred embodiment, Ar carries 1 radical $R^a$ which selected from fluorinated $C_1$-$C_4$-alkoxy, more preferably from fluorinated $C_1$-$C_2$-alkoxy and in particular from $OCH_2F$, $OCHF_2$ and $OCF_3$.

In a more preferred embodiment of the invention, Ar carries 1 radical $R^a$ which selected from a radical of the formula $R^{a'}$, in particular isopropyl or fluorinated isopropyl like (R)-

2-fluoro-1-methylethyl, (S)-2-fluoro-1-methylethyl, (R)-2,2-difluoro-1-methylethyl, (S)-2,2-difluoro-1-methylethyl, (R)-1,2-difluoro-1-methylethyl, (S)-1,2-difluoro-1-methylethyl, (R)-2,2,2-trifluoro-1-methylethyl, (S)-2,2,2-trifluoro-1-methylethyl, 2-fluoro-1-(fluoromethyl)ethyl and 1-(difluoromethyl)-2,2-difluoroethyl, and fluorinated $C_1$-$C_4$-alkoxy, in particular $OCH_2F$, $OCHF_2$ and $OCF_3$.

In a very preferred embodiment, Ar is phenyl that carries a radical $R^a$ in the 4-position of the phenyl ring, where $R^a$ is selected from a radical of the formula $R^{a'}$, in particular isopropyl or fluorinated isopropyl like (R)-2-fluoro-1-methylethyl, (S)-2-fluoro-1-methylethyl, (R)-2,2-difluoro-1-methylethyl, (S)-2,2-difluoro-1-methylethyl, (R)-1,2-difluoro-1-methylethyl, (S)-1,2-difluoro-1-methylethyl, (R)-2,2,2-trifluoro-1-methylethyl, (S)-2,2,2-trifluoro-1-methylethyl, 2-fluoro-1-(fluoromethyl)ethyl and 1-(difluoromethyl)-2,2-difluoroethyl, and fluorinated $C_1$-$C_4$-alkoxy, in particular $OCH_2F$, $OCHF_2$ and $OCF_3$. Particularly, Ar does not carry any radical $R^b$.

The radical $R^1$ is preferably different from hydrogen, in particular $C_2$-$C_4$-alkyl, $C_3$-$C_4$-cycloalkyl, $C_3$-$C_4$-alkenyl, fluorinated $C_2$-$C_4$-alkyl, fluorinated $C_3$-$C_4$-cycloalkyl or fluorinated $C_3$-$C_4$-alkenyl, more preferably n-propyl, fluorinated $C_2$-$C_3$-alkyl or 1-propen-3-yl(allyl), most preferably propyl or 1-propen-3-yl.

Preferably the moiety E is N—$R^3$ wherein $R^3$ is as defined above. $R^3$ is in particular H or methyl and most preferred H.

One preferred embodiment of the invention relates to compounds of the formula I, wherein $R^{1a}$ is hydrogen.

Another embodiment of the invention relates to compounds of the formula I, wherein $R^{1a}$ is $C_2$-$C_4$-alkyl, $C_3$-$C_4$-cycloalkyl, $C_3$-$C_4$-alkenyl, fluorinated $C_2$-$C_4$-alkyl, fluorinated $C_3$-$C_4$-cycloalkyl or fluorinated $C_3$-$C_4$-alkenyl, in particular n-propyl, fluorinated $C_2$-$C_3$-alkyl or 1-propen-3-yl, more particularly propyl or 1-propen-3-yl.

The radicals $R^2$ and $R^{2a}$ are preferably methyl, fluorinated methyl or hydrogen, in particular hydrogen.

Together with the benzene ring, the moiety X ⋯ C(R)—Y (R is $CH_2NR^1R^{1a}$) forms a bicyclic moiety. The fused ring, which is formed by the moiety X ⋯ C(R)—Y, is preferably a 5- or 6-membered ring.

In one embodiment of the invention, the moiety X ⋯ C(R)—Y (R is $CH_2NR^1R^{1a}$) forms a fused carbocyclic moiety, i.e. neither X nor Y comprise a heteroatom as ring member. Preferably the fused carbocyclic moiety is a 5- or 6-membered ring.

In this embodiment X is preferably $CHR^2$ and in particular $CH_2$. In this embodiment Y is preferably $CHR^{2a}$ or $CHR^{2a}CH_2$, in particular $CH_2$ or $CH_2CH_2$. In this embodiment, X may also be absent, i.e. X depicts a single bond, which connects the CR-moiety with the carbon atom of the fused benzene ring. Y is then preferably $CHR^{2a}CH_2$ or $CHR^{2a}CH_2CH_2$, in particular $CH_2CH_2$ or $CH_2CH_2CH_2$.

In another embodiment of the invention, the moiety X ⋯ C(R)—Y (R is $CH_2NR^1R^{1a}$) forms a fused heterocyclic moiety, i.e. X and/or Y comprise a nitrogen atom as ring member. Preferably the fused heterocyclic moiety is a 5- or 6-membered ring.

This embodiment X relates in particular to compounds I, wherein X is $CHR^2$ and in particular $CH_2$, while Y is N—$R^2$, in particular NH. This embodiment also relates to compounds wherein X is N or $CR^2$ and in particular N or CH, while Y is N—$R^2$, in particular NH.

Although it is generally preferred that $R^2$ and $R^{2a}$ are hydrogen, it may also be preferred that $R^{1a}$ and $R^2$ or $R^{1a}$ and $R^{2a}$, if present, together form a moiety $(CH_2)_n$, wherein n is as defined above and in particular 1 or 2. Thereby an additional fused ring is formed, which may be transfused or cis-fused. In particular, this embodiment relates to compounds of the general formula I, wherein X is $CR^2$, $CHR^2$ or $CHR^2CH_2$ and $R^{1a}$ and $R^2$ together are $(CH_2)_n$ with n being 1, 2 or 3, more preferably 1 or 2. Amongst these compounds, those are preferred, wherein Y is $NR^{2a}$, $CH_2$ or $CH_2CH_2$. This embodiment also relates to compounds of the general formula I, wherein Y is $CHR^{2a}$, $CHR^{2a}CH_2$ or $CHR^{2a}CH_2CH_2$ and $R^{1a}$ and $R^{2a}$ together are $(CH_2)_n$ with n being 1, 2 or 3, more preferably 1 or 2. Amongst these compounds, those are preferred, wherein X is $NR^2$, $CH_2$ or $CH_2CH_2$. This embodiment also relates to compounds of the general formula I, wherein X a covalent bond and Y is $CHR^{2a}CH_2CH_2$ and $R^{1a}$ and $R^{2a}$ together are $(CH_2)_n$ with n being 1, 2 or 3, more preferably 1. Alternatively, this embodiment relates to compounds of the general formula I, wherein X $CH_2CH_2$ and Y is $CHR^{2a}$ and $R^{1a}$ and $R^{2a}$ together are $(CH_2)_n$ with n being 1, 2 or 3, more preferably 1. Preferred examples for these tricyclic systems are compounds of the following formulae:

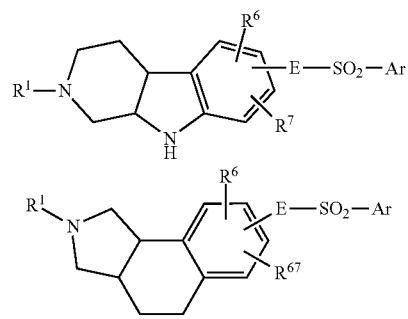

Preferably, $R^4$ and $R^5$ are independently H, $C_1$-$C_4$-alkyl or $C_1$-$C_4$-alkoxy.

Preferably, $R^6$ and $R^7$ are both hydrogen or both halogen, more preferably both hydrogen or both chlorine. In case there is no tricyclic system as described above, i.e. $R^{1a}$ and $R^{2a}$ or $R^{1a}$ and $R^2$ do not form an alkylene bridge $(CH_2)_m$, it is preferred that $R^6$ and $R^7$ are both hydrogen.

Particularly preferred compounds I are those of formulae I.a, I.b, I.c, I.d, I.e, I.f, I.g, I.h and I.i, wherein $R^1$ and Ar have the above-defined meanings. Preferred meanings of $R^1$ and Ar are as defined above.

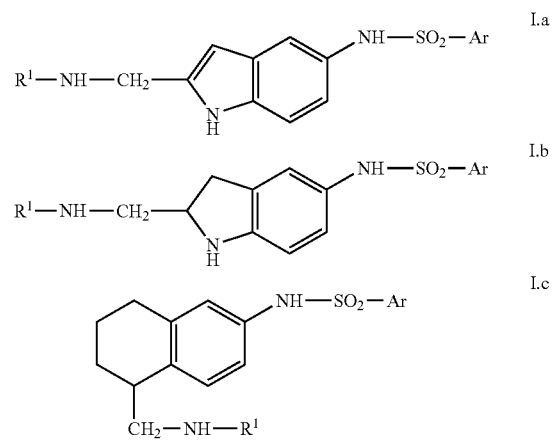

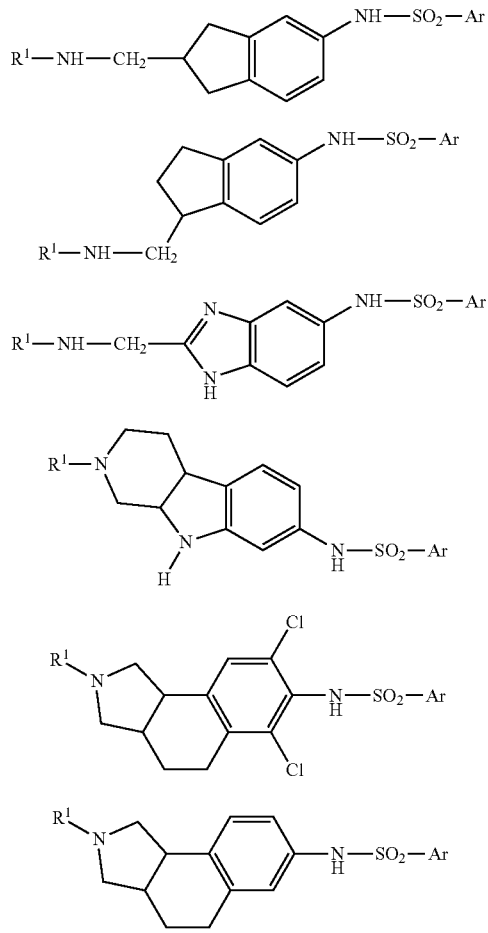

Examples of preferred compounds which are represented by the formulae I.a, I.b, I.c, I.d, I.e, I.f, I.g, I.h and I.i are the individual compounds I.a, I.b, I.c, I.d, I.e, I.f, I.g, I.h and I.i compiled above, where the variables Ar and $R^1$ have the meanings given in one row of table A:

TABLE A

| No. | $R^1$ | Ar |
|---|---|---|
| 1. | propyl | 4-methylphenyl |
| 2. | propyl | 4-ethylphenyl |
| 3. | propyl | 4-propylphenyl |
| 4. | propyl | 4-isopropylphenyl |
| 5. | propyl | 4-sec-butylphenyl |
| 6. | propyl | 4-isobutylphenyl |
| 7. | propyl | 4-(1,1-dimethylpropyl)-phenyl |
| 8. | propyl | 4-vinylphenyl |
| 9. | propyl | 4-isopropenylphenyl |
| 10. | propyl | 4-fluorophenyl |
| 11. | propyl | 4-chlorophenyl |
| 12. | propyl | 4-bromophenyl |
| 13. | propyl | 4-(fluoromethyl)phenyl |
| 14. | propyl | 3-(fluoromethyl)phenyl |
| 15. | propyl | 2-(fluoromethyl)phenyl |
| 16. | propyl | 4-(difluoromethyl)phenyl |
| 17. | propyl | 3-(difluoromethyl)phenyl |
| 18. | propyl | 2-(difluoromethyl)phenyl |
| 19. | propyl | 4-(trifluoromethyl)phenyl |
| 20. | propyl | 3-(trifluoromethyl)phenyl |
| 21. | propyl | 2-(trifluoromethyl)phenyl |
| 22. | propyl | 4-(1-fluoroethyl)-phenyl |
| 23. | propyl | 4-((S)-1-fluoroethyl)-phenyl |
| 24. | propyl | 4-((R)-1-fluoroethyl)-phenyl |
| 25. | propyl | 4-(2-fluoroethyl)-phenyl |
| 26. | propyl | 4-(1,1-difluoroethyl)-phenyl |
| 27. | propyl | 4-(2,2-difluoroethyl)-phenyl |
| 28. | propyl | 4-(2,2,2-trifluoroethyl)-phenyl |
| 29. | propyl | 4-(3-fluoropropyl)-phenyl |
| 30. | propyl | 4-(2-fluoropropyl)-phenyl |
| 31. | propyl | 4-((S)-2-fluoropropyl)-phenyl |
| 32. | propyl | 4-((R)-2-fluoropropyl)-phenyl |
| 33. | propyl | 4-(3,3-difluoropropyl)-phenyl |
| 34. | propyl | 4-(3,3,3-trifluoropropyl)-phenyl |
| 35. | propyl | 4-(1-fluoro-1-methylethyl)-phenyl |
| 36. | propyl | 4-(2-fluoro-1-methylethyl)-phenyl |
| 37. | propyl | 4-((S)-2-fluoro-1-methylethyl)-phenyl |
| 38. | propyl | 4-((R)-2-fluoro-1-methylethyl)-phenyl |
| 39. | propyl | 4-(2,2-difluoro-1-methylethyl)-phenyl |
| 40. | propyl | 4-((S)-2,2-difluoro-1-methylethyl)-phenyl |
| 41. | propyl | 4-((R)-2,2-difluoro-1-methylethyl)-phenyl |
| 42. | propyl | 4-(2,2,2-trifluoro-1-methylethyl)-phenyl |
| 43. | propyl | 4-((S)-2,2,2-trifluoro-1-methylethyl)-phenyl |
| 44. | propyl | 4-((R)-2,2,2-trifluoro-1-methylethyl)-phenyl |
| 45. | propyl | 4-(2-fluoro-1-fluoromethylethyl)-phenyl |
| 46. | propyl | 4-(1-difluoromethyl-2,2-difluoroethyl)-phenyl |
| 47. | propyl | 4-(1,1-dimethyl-2-fluoroethyl)-phenyl |
| 48. | propyl | 4-methoxyphenyl |
| 49. | propyl | 4-ethoxyphenyl |
| 50. | propyl | 4-propoxyphenyl |
| 51. | propyl | 4-isopropoxyphenyl |
| 52. | propyl | 4-butoxyphenyl |
| 53. | propyl | 4-(fluoromethoxy)-phenyl |
| 54. | propyl | 4-(difluoromethoxy)-phenyl |
| 55. | propyl | 4-(trifluoromethoxy)-phenyl |
| 56. | propyl | 3-(trifluoromethoxy)-phenyl |
| 57. | propyl | 4-(2-fluoroethoxy)-phenyl |
| 58. | propyl | 4-(2,2-difluoroethoxy)-phenyl |
| 59. | propyl | 4-(2,2,2-trifluoroethoxy)-phenyl |
| 60. | propyl | 4-(1,1,2,2-tetrafluoroethoxy)-phenyl |
| 61. | propyl | 4-cyclopropylphenyl |
| 62. | propyl | 4-cyclobutylphenyl |
| 63. | propyl | 4-cyclopentylphenyl |
| 64. | propyl | 4-(2,2-difluorocyclopropyl)-phenyl |
| 65. | propyl | 3,4-difluorophenyl |
| 66. | propyl | 4-bromo-3-fluorophenyl |
| 67. | propyl | 4-bromo-2-fluorophenyl |
| 68. | propyl | 4-bromo-2,5-difluorophenyl |
| 69. | propyl | 2-fluoro-4-isopropylphenyl |
| 70. | propyl | 3-fluoro-4-isopropylphenyl |
| 71. | propyl | 4-(1-hydroxy-1-methylethyl)-phenyl |
| 72. | propyl | 4-(2-hydroxy-2-methylpropyl)-phenyl |
| 73. | propyl | 4-acetylphenyl |
| 74. | propyl | 4-carboxyphenyl |
| 75. | propyl | 4-cyanophenyl |
| 76. | propyl | 4-hydroxyphenyl |
| 77. | propyl | 4-(O-benzyl)-phenyl |
| 78. | propyl | 4-(2-methoxyethoxy)-phenyl |
| 79. | propyl | 4-(CH$_2$—N(CH$_3$)$_2$)-phenyl |
| 80. | propyl | 4-(NH—CO—NH$_2$)-phenyl |
| 81. | propyl | 4-(methylsulfanyl)-phenyl |
| 82. | propyl | 4-(fluoromethylsulfanyl)-phenyl |
| 83. | propyl | 4-(difluoromethylsulfanyl)-phenyl |
| 84. | propyl | 4-(trifluoromethylsulfanyl)-phenyl |
| 85. | propyl | 4-(methylsulfonyl)-phenyl |
| 86. | propyl | 4-(N-methoxy-N-methyl-amino)-phenyl |
| 87. | propyl | 4-(methoxyamino)-phenyl |
| 88. | propyl | 4-(ethoxyamino)-phenyl |
| 89. | propyl | 4-(N-methylaminooxy)-phenyl |
| 90. | propyl | 4-(N,N-dimethylaminooxy)-phenyl |
| 91. | propyl | 4-(azetidin-1-yl)-phenyl |
| 92. | propyl | 4-(2-methylazetidin-1-yl)-phenyl |
| 93. | propyl | 4-((S)-2-methylazetidin-1-yl)-phenyl |
| 94. | propyl | 4-((R)-2-methylazetidin-1-yl)-phenyl |
| 95. | propyl | 4-(3-fluoroazetidin-1-yl)-phenyl |
| 96. | propyl | 4-(3-methoxyazetidin-1-yl)-phenyl |
| 97. | propyl | 4-(3-hydroxyazetidin-1-yl)-phenyl |
| 98. | propyl | 4-(pyrrolidin-1-yl)-phenyl |
| 99. | propyl | 4-(pyrrolidin-2-yl)-phenyl |
| 100. | propyl | 4-((S)-pyrrolidin-2-yl)-phenyl |

TABLE A-continued

| No. | R¹ | Ar |
|---|---|---|
| 101. | propyl | 4-((R)-pyrrolidin-2-yl)-phenyl |
| 102. | propyl | 4-(pyrrolidin-3-yl)-phenyl |
| 103. | propyl | 4-((S)-pyrrolidin-3-yl)-phenyl |
| 104. | propyl | 4-((R)-pyrrolidin-3-yl)-phenyl |
| 105. | propyl | 4-(2-fluoropyrrolidin-1-yl)-phenyl |
| 106. | propyl | 4-((S)-2-fluoropyrrolidin-1-yl)-phenyl |
| 107. | propyl | 4-((R)-2-fluoropyrrolidin-1-yl)-phenyl |
| 108. | propyl | 4-(3-fluoropyrrolidin-1-yl)-phenyl |
| 109. | propyl | 4-((S)-3-fluoropyrrolidin-1-yl)-phenyl |
| 110. | propyl | 4-((R)-3-fluoropyrrolidin-1-yl)-phenyl |
| 111. | propyl | 4-(2,2-difluoropyrrolidin-1-yl)-phenyl |
| 112. | propyl | 4-(3,3-difluoropyrrolidin-1-yl)-phenyl |
| 113. | propyl | 4-(2-methylpyrrolidin-1-yl)-phenyl |
| 114. | propyl | 4-((S)-2-methylpyrrolidin-1-yl)-phenyl |
| 115. | propyl | 4-((R)-2-methylpyrrolidin-1-yl)-phenyl |
| 116. | propyl | 4-(3-methylpyrrolidin-1-yl)-phenyl |
| 117. | propyl | 4-((S)-3-methylpyrrolidin-1-yl)-phenyl |
| 118. | propyl | 4-((R)-3-methylpyrrolidin-1-yl)-phenyl |
| 119. | propyl | 4-(1-methylpyrrolidin-2-yl)-phenyl |
| 120. | propyl | 4-((S)-1-methylpyrrolidin-2-yl)-phenyl |
| 121. | propyl | 4-((R)-1-methylpyrrolidin-2-yl)-phenyl |
| 122. | propyl | 4-(1-methylpyrrolidin-3-yl)-phenyl |
| 123. | propyl | 4-((S)-1-methylpyrrolidin-3-yl)-phenyl |
| 124. | propyl | 4-((R)-1-methylpyrrolidin-3-yl)-phenyl |
| 125. | propyl | 4-(2,2-dimethylpyrrolidin-1-yl)-phenyl |
| 126. | propyl | 4-(3,3-dimethylpyrrolidin-1-yl)-phenyl |
| 127. | propyl | 4-(2-trifluoromethylpyrrolidin-1-yl)-phenyl |
| 128. | propyl | 4-((S)-2-trifluoromethylpyrrolidin-1-yl)-phenyl |
| 129. | propyl | 4-((R)-2-trifluoromethylpyrrolidin-1-yl)-phenyl |
| 130. | propyl | 4-(3-trifluoromethylpyrrolidin-1-yl)-phenyl |
| 131. | propyl | 4-((S)-3-trifluoromethylpyrrolidin-1-yl)-phenyl |
| 132. | propyl | 4-((R)-3-trifluoromethylpyrrolidin-1-yl)-phenyl |
| 133. | propyl | 4-(2-oxopyrrolidin-1-yl)-phenyl |
| 134. | propyl | 4-(2-oxo-oxazolidin-3-yl)-phenyl |
| 135. | propyl | 4-(piperidin-1-yl)-phenyl |
| 136. | propyl | 4-(2-methylpiperidin-1-yl)-phenyl |
| 137. | propyl | 4-((S)-2-methylpiperidin-1-yl)-phenyl |
| 138. | propyl | 4-((R)-2-methylpiperidin-1-yl)-phenyl |
| 139. | propyl | 4-(piperazin-1-yl)-phenyl |
| 140. | propyl | 4-(4-methylpiperazin-1-yl)-phenyl |
| 141. | propyl | 4-(morpholin-4-yl)-phenyl |
| 142. | propyl | 4-(thiomorpholin-4-yl)-phenyl |
| 143. | propyl | 4-(1-oxo-thiomorpholin-4-yl)-phenyl |
| 144. | propyl | 4-(1,1-dioxo-thiomorpholin-4-yl)-phenyl |
| 145. | propyl | 4-(pyrrol-1-yl)-phenyl |
| 146. | propyl | 4-(pyrrol-2-yl)-phenyl |
| 147. | propyl | 4-(pyrrol-3-yl)-phenyl |
| 148. | propyl | 4-(1-methylpyrrol-2-yl)-phenyl |
| 149. | propyl | 4-(1-methylpyrrol-3-yl)-phenyl |
| 150. | propyl | 4-(furan-2-yl)-phenyl |
| 151. | propyl | 4-(furan-3-yl)-phenyl |
| 152. | propyl | 4-(thiophen-2-yl)-phenyl |
| 153. | propyl | 4-(thiophen-3-yl)-phenyl |
| 154. | propyl | 4-(5-propylthien-2-yl)-phenyl |
| 155. | propyl | 4-(pyrazol-1-yl)-phenyl |
| 156. | propyl | 4-(pyrazol-3-yl)-phenyl |
| 157. | propyl | 4-(pyrazol-4-yl)-phenyl |
| 158. | propyl | 4-(1-methyl-1H-pyrazol-4-yl)-phenyl |
| 159. | propyl | 4-(1-ethyl-1H-pyrazol-4-yl)-phenyl |
| 160. | propyl | 4-(1-methyl-1H-pyrazol-5-yl)-phenyl |
| 161. | propyl | 4-(1H-imidazol-2-yl)-phenyl |
| 162. | propyl | 4-(imidazol-1-yl)-phenyl |
| 163. | propyl | 4-(1-methylimidazol-2-yl)-phenyl |
| 164. | propyl | 4-(oxazol-2-yl)-phenyl |
| 165. | propyl | 4-(oxazol-4-yl)-phenyl |
| 166. | propyl | 4-(oxazol-5-yl)-phenyl |
| 167. | propyl | 4-(isoxazol-3-yl)-phenyl |
| 168. | propyl | 4-(isoxazol-4-yl)-phenyl |
| 169. | propyl | 4-(isoxazol-5-yl)-phenyl |
| 170. | propyl | 4-([1,2,3]-triazol-1-yl)-phenyl |
| 171. | propyl | 4-([1,2,4]-triazol-1-yl)-phenyl |
| 172. | propyl | 4-([1,2,3]-triazol-2-yl)-phenyl |
| 173. | propyl | 4-(4H-[1,2,4]-triazol-3-yl)-phenyl |
| 174. | propyl | 4-([1,2,4]-triazol-4-yl)-phenyl |
| 175. | propyl | 4-(2H-[1,2,3]-triazol-4-yl)-phenyl |
| 176. | propyl | 4-(4-methyl-4H-[1,2,4]-triazol-3-yl)-phenyl |
| 177. | propyl | 4-(2-methyl-2H-[1,2,3]-triazol-4-yl)-phenyl |
| 178. | propyl | 4-([1,3,4]-oxadiazol-2-yl)-phenyl |
| 179. | propyl | 4-([1,2,4]-oxadiazol-3-yl)-phenyl |
| 180. | propyl | 4-([1,2,4]-oxadiazol-5-yl)-phenyl |
| 181. | propyl | 4-([1,2,5]-oxadiazol-4-yl)-phenyl |
| 182. | propyl | 4-([1,2,3]-oxadiazol-5-yl)-phenyl |
| 183. | propyl | 4-([1,2,3]-thiadiazol-4-yl)-phenyl |
| 184. | propyl | 4-(1H-tetrazol-5-yl)-phenyl |
| 185. | propyl | 4-(tetrazol-1-yl)-phenyl |
| 186. | propyl | 4-(2-methyl-2H-tetrazol-5-yl)-phenyl |
| 187. | propyl | 4-(1-methyl-1H-tetrazol-5-yl)-phenyl |
| 188. | propyl | 4-furazan-3-yl-phenyl |
| 189. | propyl | 4-(pyrid-2-yl)-phenyl |
| 190. | propyl | 4-(pyrid-3-yl)-phenyl |
| 191. | propyl | 4-(pyrid-4-yl)-phenyl |
| 192. | propyl | 4-(pyrimidin-2-yl)-phenyl |
| 193. | propyl | 4-(pyrimidin-4-yl)-phenyl |
| 194. | propyl | 4-(pyrimidin-5-yl)-phenyl |
| 195. | propyl | 5-isopropylthiophen-2-yl |
| 196. | propyl | 2-chlorothiophen-5-yl |
| 197. | propyl | 2,5-dichlorothiophen-4-yl |
| 198. | propyl | 2,3-dichlorothiophen-5-yl |
| 199. | propyl | 2-chloro-3-nitrothiophen-5-yl |
| 200. | propyl | 2-(phenylsulfonyl)-thiophen-5-yl |
| 201. | propyl | 2-(pyridin-2-yl)thiophen-5-yl |
| 202. | propyl | 2-(5-(trifluoromethyl)isoxazol-3-yl)-thiophen-5-yl |
| 203. | propyl | 2-(2-methylthiazol-4-yl)-thiophen-5-yl |
| 204. | propyl | 1-methyl-1H-imidazol-4-yl |
| 205. | propyl | 1,2-dimethyl-1H-imidazol-4-yl |
| 206. | propyl | 3,5-dimethylisoxazol-4-yl |
| 207. | propyl | thiazol-2-yl |
| 208. | propyl | 4-methylthiazol-2-yl |
| 209. | propyl | 4-isopropylthiazol-2-yl |
| 210. | propyl | 4-trifluoromethylthiazol-2-yl |
| 211. | propyl | 5-methylthiazol-2-yl |
| 212. | propyl | 5-isopropylthiazol-2-yl |
| 213. | propyl | 5-trifluoromethylthiazol-2-yl |
| 214. | propyl | 2,4-dimethylthiazol-5-yl |
| 215. | propyl | 2-acetamido-4-methylthiazol-5-yl |
| 216. | propyl | 4H-[1,2,4]triazol-3-yl |
| 217. | propyl | 5-methyl-4H-[1,2,4]triazol-3-yl |
| 218. | propyl | 4-methyl-4H-[1,2,4]triazol-3-yl |
| 219. | propyl | 5-isopropyl-4H-[1,2,4]triazol-3-yl |
| 220. | propyl | 5-trifluoromethyl-4H-[1,2,4]triazol-3-yl |
| 221. | propyl | 4,5-dimethyl-4H-[1,2,4]triazol-3-yl |
| 222. | propyl | 5-isopropyl-4-methyl-4H-[1,2,4]triazol-3-yl |
| 223. | propyl | 5-trifluoromethyl-4-methyl-4H-[1,2,4]triazol-3-yl |
| 224. | propyl | [1,3,4]thiadiazol-2-yl |
| 225. | propyl | 5-methyl-[1,3,4]thiadiazol-2-yl |
| 226. | propyl | 5-isopropyl-[1,3,4]thiadiazol-2-yl |
| 227. | propyl | 5-trifluoromethyl-[1,3,4]thiadiazol-2-yl |
| 228. | propyl | 3-bromo-2-chloropyrid-5-yl |
| 229. | propyl | 2-(4-morpholino)-pyrid-5-yl |
| 230. | propyl | 2-phenoxypyrid-5-yl |
| 231. | propyl | (2-isopropyl)-pyrimidin-5-yl |
| 232. | propyl | (5-isopropyl)-pyrimidin-2-yl |
| 233. | propyl | 8-quinolyl |
| 234. | propyl | 5-isoquinolyl |
| 235. | propyl | 2-(trifluoroacetyl)-1,2,3,4-tetrahydroisoquinolin-7-yl |
| 236. | propyl | 5-chloro-3-methylbenzothiophen-2-yl |
| 237. | propyl | 3,4-dihydro-4-methyl-2H-benzo[b][1,4]oxazinyl |
| 238. | propyl | benzothiazol-6-yl |
| 239. | propyl | benzo[2,1,3]oxadiazol-4-yl |
| 240. | propyl | 5-chlorobenzo[2,1,3]oxadiazol-4-yl |
| 241. | propyl | 7-chlorobenzo[2,1,3]oxadiazol-4-yl |
| 242. | propyl | benzo[2,1,3]thiadiazol-4-yl |
| 243. | ethyl | 4-methylphenyl |
| 244. | ethyl | 4-ethylphenyl |
| 245. | ethyl | 4-propylphenyl |
| 246. | ethyl | 4-isopropylphenyl |
| 247. | ethyl | 4-sec-butylphenyl |
| 248. | ethyl | 4-isobutylphenyl |

TABLE A-continued

| No. | R¹ | Ar |
|---|---|---|
| 249. | ethyl | 4-(1,1-dimethylpropyl)-phenyl |
| 250. | ethyl | 4-vinylphenyl |
| 251. | ethyl | 4-isopropenylphenyl |
| 252. | ethyl | 4-fluorophenyl |
| 253. | ethyl | 4-chlorophenyl |
| 254. | ethyl | 4-bromophenyl |
| 255. | ethyl | 4-(fluoromethyl)phenyl |
| 256. | ethyl | 3-(fluoromethyl)phenyl |
| 257. | ethyl | 2-(fluoromethyl)phenyl |
| 258. | ethyl | 4-(difluoromethyl)phenyl |
| 259. | ethyl | 3-(difluoromethyl)phenyl |
| 260. | ethyl | 2-(difluoromethyl)phenyl |
| 261. | ethyl | 4-(trifluoromethyl)phenyl |
| 262. | ethyl | 3-(trifluoromethyl)phenyl |
| 263. | ethyl | 2-(trifluoromethyl)phenyl |
| 264. | ethyl | 4-(1-fluoroethyl)-phenyl |
| 265. | ethyl | 4-((S)-1-fluoroethyl)-phenyl |
| 266. | ethyl | 4-((R)-1-fluoroethyl)-phenyl |
| 267. | ethyl | 4-(2-fluoroethyl)-phenyl |
| 268. | ethyl | 4-(1,1-difluoroethyl)-phenyl |
| 269. | ethyl | 4-(2,2-difluoroethyl)-phenyl |
| 270. | ethyl | 4-(2,2,2-trifluoroethyl)-phenyl |
| 271. | ethyl | 4-(3-fluoropropyl)-phenyl |
| 272. | ethyl | 4-(2-fluoropropyl)-phenyl |
| 273. | ethyl | 4-((S)-2-fluoropropyl)-phenyl |
| 274. | ethyl | 4-((R)-2-fluoropropyl)-phenyl |
| 275. | ethyl | 4-(3,3-difluoropropyl)-phenyl |
| 276. | ethyl | 4-(3,3,3-trifluoropropyl)-phenyl |
| 277. | ethyl | 4-(1-fluoro-1-methylethyl)-phenyl |
| 278. | ethyl | 4-(2-fluoro-1-methylethyl)-phenyl |
| 279. | ethyl | 4-((S)-2-fluoro-1-methylethyl)-phenyl |
| 280. | ethyl | 4-((R)-2-fluoro-1-methylethyl)-phenyl |
| 281. | ethyl | 4-(2,2-difluoro-1-methylethyl)-phenyl |
| 282. | ethyl | 4-((S)-2,2-difluoro-1-methylethyl)-phenyl |
| 283. | ethyl | 4-((R)-2,2-difluoro-1-methylethyl)-phenyl |
| 284. | ethyl | 4-(2,2,2-trifluoro-1-methylethyl)-phenyl |
| 285. | ethyl | 4-((S)-2,2,2-trifluoro-1-methylethyl)-phenyl |
| 286. | ethyl | 4-((R)-2,2,2-trifluoro-1-methylethyl)-phenyl |
| 287. | ethyl | 4-(2-fluoro-1-fluoromethylethyl)-phenyl |
| 288. | ethyl | 4-(1-difluoromethyl-2,2-difluoroethyl)-phenyl |
| 289. | ethyl | 4-(1,1-dimethyl-2-fluoroethyl)-phenyl |
| 290. | ethyl | 4-methoxyphenyl |
| 291. | ethyl | 4-ethoxyphenyl |
| 292. | ethyl | 4-propoxyphenyl |
| 293. | ethyl | 4-isopropoxyphenyl |
| 294. | ethyl | 4-butoxyphenyl |
| 295. | ethyl | 4-(fluoromethoxy)-phenyl |
| 296. | ethyl | 4-(difluoromethoxy)-phenyl |
| 297. | ethyl | 4-(trifluoromethoxy)-phenyl |
| 298. | ethyl | 3-(trifluoromethoxy)-phenyl |
| 299. | ethyl | 4-(2-fluoroethoxy)-phenyl |
| 300. | ethyl | 4-(2,2-difluoroethoxy)-phenyl |
| 301. | ethyl | 4-(2,2,2-trifluoroethoxy)-phenyl |
| 302. | ethyl | 4-(1,1,2,2-tetrafluoroethoxy)-phenyl |
| 303. | ethyl | 4-cyclopropylphenyl |
| 304. | ethyl | 4-cyclobutylphenyl |
| 305. | ethyl | 4-cyclopentylphenyl |
| 306. | ethyl | 4-(2,2-difluorocyclopropyl)-phenyl |
| 307. | ethyl | 3,4-difluorophenyl |
| 308. | ethyl | 4-bromo-3-fluorophenyl |
| 309. | ethyl | 4-bromo-2-fluorophenyl |
| 310. | ethyl | 4-bromo-2,5-difluorophenyl |
| 311. | ethyl | 2-fluoro-4-isopropylphenyl |
| 312. | ethyl | 3-fluoro-4-isopropylphenyl |
| 313. | ethyl | 4-(1-hydroxy-1-methylethyl)-phenyl |
| 314. | ethyl | 4-(2-hydroxy-2-methylpropyl)-phenyl |
| 315. | ethyl | 4-acetylphenyl |
| 316. | ethyl | 4-carboxyphenyl |
| 317. | ethyl | 4-cyanophenyl |
| 318. | ethyl | 4-hydroxyphenyl |
| 319. | ethyl | 4-(O-benzyl)-phenyl |
| 320. | ethyl | 4-(2-methoxyethoxy)-phenyl |
| 321. | ethyl | 4-(CH₂—N(CH₃)₂)-phenyl |
| 322. | ethyl | 4-(NH—CO—NH₂)-phenyl |
| 323. | ethyl | 4-(methylsulfanyl)-phenyl |
| 324. | ethyl | 4-(fluoromethylsulfanyl)-phenyl |
| 325. | ethyl | 4-(difluoromethylsulfanyl)-phenyl |
| 326. | ethyl | 4-(trifluoromethylsulfanyl)-phenyl |
| 327. | ethyl | 4-(methylsulfonyl)-phenyl |
| 328. | ethyl | 4-(N-methoxy-N-methyl-amino)-phenyl |
| 329. | ethyl | 4-(methoxyamino)-phenyl |
| 330. | ethyl | 4-(ethoxyamino)-phenyl |
| 331. | ethyl | 4-(N-methylaminooxy)-phenyl |
| 332. | ethyl | 4-(N,N-dimethylaminooxy)-phenyl |
| 333. | ethyl | 4-(azetidin-1-yl)-phenyl |
| 334. | ethyl | 4-(2-methylazetidin-1-yl)-phenyl |
| 335. | ethyl | 4-((S)-2-methylazetidin-1-yl)-phenyl |
| 336. | ethyl | 4-((R)-2-methylazetidin-1-yl)-phenyl |
| 337. | ethyl | 4-(3-fluoroazetidin-1-yl)-phenyl |
| 338. | ethyl | 4-(3-methoxyazetidin-1-yl)-phenyl |
| 339. | ethyl | 4-(3-hydroxyazetidin-1-yl)-phenyl |
| 340. | ethyl | 4-(pyrrolidin-1-yl)-phenyl |
| 341. | ethyl | 4-(pyrrolidin-2-yl)-phenyl |
| 342. | ethyl | 4-((S)-pyrrolidin-2-yl)-phenyl |
| 343. | ethyl | 4-((R)-pyrrolidin-2-yl)-phenyl |
| 344. | ethyl | 4-(pyrrolidin-3-yl)-phenyl |
| 345. | ethyl | 4-((S)-pyrrolidin-3-yl)-phenyl |
| 346. | ethyl | 4-((R)-pyrrolidin-3-yl)-phenyl |
| 347. | ethyl | 4-(2-fluoropyrrolidin-1-yl)-phenyl |
| 348. | ethyl | 4-((S)-2-fluoropyrrolidin-1-yl)-phenyl |
| 349. | ethyl | 4-((R)-2-fluoropyrrolidin-1-yl)-phenyl |
| 350. | ethyl | 4-(3-fluoropyrrolidin-1-yl)-phenyl |
| 351. | ethyl | 4-((S)-3-fluoropyrrolidin-1-yl)-phenyl |
| 352. | ethyl | 4-((R)-3-fluoropyrrolidin-1-yl)-phenyl |
| 353. | ethyl | 4-(2,2-difluoropyrrolidin-1-yl)-phenyl |
| 354. | ethyl | 4-(3,3-difluoropyrrolidin-1-yl)-phenyl |
| 355. | ethyl | 4-(2-methylpyrrolidin-1-yl)-phenyl |
| 356. | ethyl | 4-((S)-2-methylpyrrolidin-1-yl)-phenyl |
| 357. | ethyl | 4-((R)-2-methylpyrrolidin-1-yl)-phenyl |
| 358. | ethyl | 4-(3-methylpyrrolidin-1-yl)-phenyl |
| 359. | ethyl | 4-((S)-3-methylpyrrolidin-1-yl)-phenyl |
| 360. | ethyl | 4-((R)-3-methylpyrrolidin-1-yl)-phenyl |
| 361. | ethyl | 4-(1-methylpyrrolidin-2-yl)-phenyl |
| 362. | ethyl | 4-((S)-1-methylpyrrolidin-2-yl)-phenyl |
| 363. | ethyl | 4-((R)-1-methylpyrrolidin-2-yl)-phenyl |
| 364. | ethyl | 4-(1-methylpyrrolidin-3-yl)-phenyl |
| 365. | ethyl | 4-((S)-1-methylpyrrolidin-3-yl)-phenyl |
| 366. | ethyl | 4-((R)-1-methylpyrrolidin-3-yl)-phenyl |
| 367. | ethyl | 4-(2,2-dimethylpyrrolidin-1-yl)-phenyl |
| 368. | ethyl | 4-(3,3-dimethylpyrrolidin-1-yl)-phenyl |
| 369. | ethyl | 4-(2-trifluoromethylpyrrolidin-1-yl)-phenyl |
| 370. | ethyl | 4-((S)-2-trifluoromethylpyrrolidin-1-yl)-phenyl |
| 371. | ethyl | 4-((R)-2-trifluoromethylpyrrolidin-1-yl)-phenyl |
| 372. | ethyl | 4-(3-trifluoromethylpyrrolidin-1-yl)-phenyl |
| 373. | ethyl | 4-((S)-3-trifluoromethylpyrrolidin-1-yl)-phenyl |
| 374. | ethyl | 4-((R)-3-trifluoromethylpyrrolidin-1-yl)-phenyl |
| 375. | ethyl | 4-(2-oxopyrrolidin-1-yl)-phenyl |
| 376. | ethyl | 4-(2-oxo-oxazolidin-3-yl)-phenyl |
| 377. | ethyl | 4-(piperidin-1-yl)-phenyl |
| 378. | ethyl | 4-(2-methylpiperidin-1-yl)-phenyl |
| 379. | ethyl | 4-((S)-2-methylpiperidin-1-yl)-phenyl |
| 380. | ethyl | 4-((R)-2-methylpiperidin-1-yl)-phenyl |
| 381. | ethyl | 4-(piperazin-1-yl)-phenyl |
| 382. | ethyl | 4-(4-methylpiperazin-1-yl)-phenyl |
| 383. | ethyl | 4-(morpholin-4-yl)-phenyl |
| 384. | ethyl | 4-(thiomorpholin-4-yl)-phenyl |
| 385. | ethyl | 4-(1-oxo-thiomorpholin-4-yl)-phenyl |
| 386. | ethyl | 4-(1,1-dioxo-thiomorpholin-4-yl)-phenyl |
| 387. | ethyl | 4-(pyrrol-1-yl)-phenyl |
| 388. | ethyl | 4-(pyrrol-2-yl)-phenyl |
| 389. | ethyl | 4-(pyrrol-3-yl)-phenyl |
| 390. | ethyl | 4-(1-methylpyrrol-2-yl)-phenyl |
| 391. | ethyl | 4-(1-methylpyrrol-3-yl)-phenyl |
| 392. | ethyl | 4-(furan-2-yl)-phenyl |
| 393. | ethyl | 4-(furan-3-yl)-phenyl |
| 394. | ethyl | 4-(thiophen-2-yl)-phenyl |
| 395. | ethyl | 4-(thiophen-3-yl)-phenyl |
| 396. | ethyl | 4-(5-propylthien-2-yl)-phenyl |
| 397. | ethyl | 4-(pyrazol-1-yl)-phenyl |
| 398. | ethyl | 4-(pyrazol-3-yl)-phenyl |
| 399. | ethyl | 4-(pyrazol-4-yl)-phenyl |

TABLE A-continued

| No. | R¹ | Ar |
|---|---|---|
| 400. | ethyl | 4-(1-methyl-1H-pyrazol-4-yl)-phenyl |
| 401. | ethyl | 4-(1-ethyl-1H-pyrazol-4-yl)-phenyl |
| 402. | ethyl | 4-(1-methyl-1H-pyrazol-5-yl)-phenyl |
| 403. | ethyl | 4-(1H-imidazol-2-yl)-phenyl |
| 404. | ethyl | 4-(imidazol-1-yl)-phenyl |
| 405. | ethyl | 4-(1-methylimidazol-2-yl)-phenyl |
| 406. | ethyl | 4-(oxazol-2-yl)-phenyl |
| 407. | ethyl | 4-(oxazol-4-yl)-phenyl |
| 408. | ethyl | 4-(oxazol-5-yl)-phenyl |
| 409. | ethyl | 4-(isoxazol-3-yl)-phenyl |
| 410. | ethyl | 4-(isoxazol-4-yl)-phenyl |
| 411. | ethyl | 4-(isoxazol-5-yl)-phenyl |
| 412. | ethyl | 4-([1,2,3]-triazol-1-yl)-phenyl |
| 413. | ethyl | 4-([1,2,4]-triazol-1-yl)-phenyl |
| 414. | ethyl | 4-([1,2,3]-triazol-2-yl)-phenyl |
| 415. | ethyl | 4-(4H-[1,2,4]-triazol-3-yl)-phenyl |
| 416. | ethyl | 4-([1,2,4]-triazol-4-yl)-phenyl |
| 417. | ethyl | 4-(2H-[1,2,3]-triazol-4-yl)-phenyl |
| 418. | ethyl | 4-(4-methyl-4H-[1,2,4]-triazol-3-yl)-phenyl |
| 419. | ethyl | 4-(2-methyl-2H-[1,2,3]-triazol-4-yl)-phenyl |
| 420. | ethyl | 4-([1,3,4]-oxadiazol-2-yl)-phenyl |
| 421. | ethyl | 4-([1,2,4]-oxadiazol-3-yl)-phenyl |
| 422. | ethyl | 4-([1,2,4]-oxadiazol-5-yl)-phenyl |
| 423. | ethyl | 4-([1,2,3]-oxadiazol-4-yl)-phenyl |
| 424. | ethyl | 4-([1,2,3]-oxadiazol-5-yl)-phenyl |
| 425. | ethyl | 4-([1,2,3]-thiadiazol-4-yl)-phenyl |
| 426. | ethyl | 4-(1H-tetrazol-5-yl)-phenyl |
| 427. | ethyl | 4-(tetrazol-1-yl)-phenyl |
| 428. | ethyl | 4-(2-methyl-2H-tetrazol-5-yl)-phenyl |
| 429. | ethyl | 4-(1-methyl-1H-tetrazol-5-yl)-phenyl |
| 430. | ethyl | 4-furazan-3-yl-phenyl |
| 431. | ethyl | 4-(pyrid-2-yl)-phenyl |
| 432. | ethyl | 4-(pyrid-3-yl)-phenyl |
| 433. | ethyl | 4-(pyrid-4-yl)-phenyl |
| 434. | ethyl | 4-(pyrimidin-2-yl)-phenyl |
| 435. | ethyl | 4-(pyrimidin-4-yl)-phenyl |
| 436. | ethyl | 4-(pyrimidin-5-yl)-phenyl |
| 437. | ethyl | 5-isopropylthiophen-2-yl |
| 438. | ethyl | 2-chlorothiophen-5-yl |
| 439. | ethyl | 2,5-dichlorothiophen-4-yl |
| 440. | ethyl | 2,3-dichlorothiophen-5-yl |
| 441. | ethyl | 2-chloro-3-nitrothiophen-5-yl |
| 442. | ethyl | 2-(phenylsulfonyl)-thiophen-5-yl |
| 443. | ethyl | 2-(pyridin-2-yl)thiophen-5-yl |
| 444. | ethyl | 2-(5-(trifluoromethyl)isoxazol-3-yl)-thiophen-5-yl |
| 445. | ethyl | 2-(2-methylthiazol-4-yl)-thiophen-5-yl |
| 446. | ethyl | 1-methyl-1H-imidazol-4-yl |
| 447. | ethyl | 1,2-dimethyl-1H-imidazol-4-yl |
| 448. | ethyl | 3,5-dimethylisoxazol-4-yl |
| 449. | ethyl | thiazol-2-yl |
| 450. | ethyl | 4-methylthiazol-2-yl |
| 451. | ethyl | 4-isopropylthiazol-2-yl |
| 452. | ethyl | 4-trifluoromethylthiazol-2-yl |
| 453. | ethyl | 5-methylthiazol-2-yl |
| 454. | ethyl | 5-isopropylthiazol-2-yl |
| 455. | ethyl | 5-trifluoromethylthiazol-2-yl |
| 456. | ethyl | 2,4-dimethylthiazol-5-yl |
| 457. | ethyl | 2-acetamido-4-methylthiazol-5-yl |
| 458. | ethyl | 4H-[1,2,4]triazol-3-yl |
| 459. | ethyl | 5-methyl-4H-[1,2,4]triazol-3-yl |
| 460. | ethyl | 4-methyl-4H-[1,2,4]triazol-3-yl |
| 461. | ethyl | 5-isopropyl-4H-[1,2,4]triazol-3-yl |
| 462. | ethyl | 5-trifluoromethyl-4H-[1,2,4]triazol-3-yl |
| 463. | ethyl | 4,5-dimethyl-4H-[1,2,4]triazol-3-yl |
| 464. | ethyl | 5-isopropyl-4-methyl-4H-[1,2,4]triazol-3-yl |
| 465. | ethyl | 5-trifluoromethyl-4-methyl-4H-[1,2,4]triazol-3-yl |
| 466. | ethyl | [1,3,4]thiadiazol-2-yl |
| 467. | ethyl | 5-methyl-[1,3,4]thiadiazol-2-yl |
| 468. | ethyl | 5-isopropyl-[1,3,4]thiadiazol-2-yl |
| 469. | ethyl | 5-trifluoromethyl-[1,3,4]thiadiazol-2-yl |
| 470. | ethyl | 3-bromo-2-chloropyrid-5-yl |
| 471. | ethyl | 2-(4-morpholino)-pyrid-5-yl |
| 472. | ethyl | 2-phenoxypyrid-5-yl |
| 473. | ethyl | (2-isopropyl)-pyrimidin-5-yl |
| 474. | ethyl | (5-isopropyl)-pyrimidin-2-yl |
| 475. | ethyl | 8-quinolyl |
| 476. | ethyl | 5-isoquinolyl |
| 477. | ethyl | 2-(trifluoroacetyl)-1,2,3,4-tetrahydroisoquinolin-7-yl |
| 478. | ethyl | 5-chloro-3-methylbenzothiophen-2-yl |
| 479. | ethyl | 3,4-dihydro-4-methyl-2H-benzo[b][1,4]oxazinyl |
| 480. | ethyl | benzothiazol-6-yl |
| 481. | ethyl | benzo[2,1,3]oxadiazol-4-yl |
| 482. | ethyl | 5-chlorobenzo[2,1,3]oxadiazol-4-yl |
| 483. | ethyl | 7-chlorobenzo[2,1,3]oxadiazol-4-yl |
| 484. | ethyl | benzo[2,1,3]thiadiazol-4-yl |
| 485. | methyl | 4-methylphenyl |
| 486. | methyl | 4-ethylphenyl |
| 487. | methyl | 4-propylphenyl |
| 488. | methyl | 4-isopropylphenyl |
| 489. | methyl | 4-sec-butylphenyl |
| 490. | methyl | 4-isobutylphenyl |
| 491. | methyl | 4-(1,1-dimethylpropyl)-phenyl |
| 492. | methyl | 4-vinylphenyl |
| 493. | methyl | 4-isopropenylphenyl |
| 494. | methyl | 4-fluorophenyl |
| 495. | methyl | 4-chlorophenyl |
| 496. | methyl | 4-bromophenyl |
| 497. | methyl | 4-(fluoromethyl)phenyl |
| 498. | methyl | 3-(fluoromethyl)phenyl |
| 499. | methyl | 2-(fluoromethyl)phenyl |
| 500. | methyl | 4-(difluoromethyl)phenyl |
| 501. | methyl | 3-(difluoromethyl)phenyl |
| 502. | methyl | 2-(difluoromethyl)phenyl |
| 503. | methyl | 4-(trifluoromethyl)phenyl |
| 504. | methyl | 3-(trifluoromethyl)phenyl |
| 505. | methyl | 2-(trifluoromethyl)phenyl |
| 506. | methyl | 4-(1-fluoroethyl)-phenyl |
| 507. | methyl | 4-((S)-1-fluoroethyl)-phenyl |
| 508. | methyl | 4-((R)-1-fluoroethyl)-phenyl |
| 509. | methyl | 4-(2-fluoroethyl)-phenyl |
| 510. | methyl | 4-(1,1-difluoroethyl)-phenyl |
| 511. | methyl | 4-(2,2-difluoroethyl)-phenyl |
| 512. | methyl | 4-(2,2,2-trifluoroethyl)-phenyl |
| 513. | methyl | 4-(3-fluoropropyl)-phenyl |
| 514. | methyl | 4-(2-fluoropropyl)-phenyl |
| 515. | methyl | 4-((S)-2-fluoropropyl)-phenyl |
| 516. | methyl | 4-((R)-2-fluoropropyl)-phenyl |
| 517. | methyl | 4-(3,3-difluoropropyl)-phenyl |
| 518. | methyl | 4-(3,3,3-trifluoropropyl)-phenyl |
| 519. | methyl | 4-(1-fluoro-1-methylethyl)-phenyl |
| 520. | methyl | 4-(2-fluoro-1-methylethyl)-phenyl |
| 521. | methyl | 4-((S)-2-fluoro-1-methylethyl)-phenyl |
| 522. | methyl | 4-((R)-2-fluoro-1-methylethyl)-phenyl |
| 523. | methyl | 4-(2,2-difluoro-1-methylethyl)-phenyl |
| 524. | methyl | 4-((S)-2,2-difluoro-1-methylethyl)-phenyl |
| 525. | methyl | 4-((R)-2,2-difluoro-1-methylethyl)-phenyl |
| 526. | methyl | 4-(2,2,2-trifluoro-1-methylethyl)-phenyl |
| 527. | methyl | 4-((S)-2,2,2-trifluoro-1-methylethyl)-phenyl |
| 528. | methyl | 4-((R)-2,2,2-trifluoro-1-methylethyl)-phenyl |
| 529. | methyl | 4-(2-fluoro-1-fluoromethylethyl)-phenyl |
| 530. | methyl | 4-(1-difluoromethyl-2,2-difluoroethyl)-phenyl |
| 531. | methyl | 4-(1,1-dimethyl-2-fluoroethyl)-phenyl |
| 532. | methyl | 4-methoxyphenyl |
| 533. | methyl | 4-ethoxyphenyl |
| 534. | methyl | 4-propoxyphenyl |
| 535. | methyl | 4-isopropoxyphenyl |
| 536. | methyl | 4-butoxyphenyl |
| 537. | methyl | 4-(fluoromethoxy)-phenyl |
| 538. | methyl | 4-(difluoromethoxy)-phenyl |
| 539. | methyl | 4-(trifluoromethoxy)-phenyl |
| 540. | methyl | 3-(trifluoromethoxy)-phenyl |
| 541. | methyl | 4-(2-fluoroethoxy)-phenyl |
| 542. | methyl | 4-(2,2-difluoroethoxy)-phenyl |
| 543. | methyl | 4-(2,2,2-trifluoroethoxy)-phenyl |
| 544. | methyl | 4-(1,1,2,2-tetrafluoroethoxy)-phenyl |
| 545. | methyl | 4-cyclopropylphenyl |
| 546. | methyl | 4-cyclobutylphenyl |
| 547. | methyl | 4-cyclopentylphenyl |
| 548. | methyl | 4-(2,2-difluorocyclopropyl)-phenyl |
| 549. | methyl | 3,4-difluorophenyl |
| 550. | methyl | 4-bromo-3-fluorophenyl |

TABLE A-continued

| No. | R¹ | Ar |
|---|---|---|
| 551. | methyl | 4-bromo-2-fluorophenyl |
| 552. | methyl | 4-bromo-2,5-difluorophenyl |
| 553. | methyl | 2-fluoro-4-isopropylphenyl |
| 554. | methyl | 3-fluoro-4-isopropylphenyl |
| 555. | methyl | 4-(1-hydroxy-1-methylethyl)-phenyl |
| 556. | methyl | 4-(2-hydroxy-2-methylpropyl)-phenyl |
| 557. | methyl | 4-acetylphenyl |
| 558. | methyl | 4-carboxyphenyl |
| 559. | methyl | 4-cyanophenyl |
| 560. | methyl | 4-hydroxyphenyl |
| 561. | methyl | 4-(O-benzyl)-phenyl |
| 562. | methyl | 4-(2-methoxyethoxy)-phenyl |
| 563. | methyl | 4-(CH$_2$—N(CH$_3$)$_2$)-phenyl |
| 564. | methyl | 4-(NH—CO—NH$_2$)-phenyl |
| 565. | methyl | 4-(methylsulfanyl)-phenyl |
| 566. | methyl | 4-(fluoromethylsulfanyl)-phenyl |
| 567. | methyl | 4-(difluoromethylsulfanyl)-phenyl |
| 568. | methyl | 4-(trifluoromethylsulfanyl)-phenyl |
| 569. | methyl | 4-(methylsulfonyl)-phenyl |
| 570. | methyl | 4-(N-methoxy-N-methyl-amino)-phenyl |
| 571. | methyl | 4-(methoxyamino)-phenyl |
| 572. | methyl | 4-(ethoxyamino)-phenyl |
| 573. | methyl | 4-(N-methylaminooxy)-phenyl |
| 574. | methyl | 4-(N,N-dimethylaminooxy)-phenyl |
| 575. | methyl | 4-(azetidin-1-yl)-phenyl |
| 576. | methyl | 4-(2-methylazetidin-1-yl)-phenyl |
| 577. | methyl | 4-((S)-2-methylazetidin-1-yl)-phenyl |
| 578. | methyl | 4-((R)-2-methylazetidin-1-yl)-phenyl |
| 579. | methyl | 4-(3-fluoroazetidin-1-yl)-phenyl |
| 580. | methyl | 4-(3-methoxyazetidin-1-yl)-phenyl |
| 581. | methyl | 4-(3-hydroxyazetidin-1-yl)-phenyl |
| 582. | methyl | 4-(pyrrolidin-1-yl)-phenyl |
| 583. | methyl | 4-(pyrrolidin-2-yl)-phenyl |
| 584. | methyl | 4-((S)-pyrrolidin-2-yl)-phenyl |
| 585. | methyl | 4-((R)-pyrrolidin-2-yl)-phenyl |
| 586. | methyl | 4-(pyrrolidin-3-yl)-phenyl |
| 587. | methyl | 4-((S)-pyrrolidin-3-yl)-phenyl |
| 588. | methyl | 4-((R)-pyrrolidin-3-yl)-phenyl |
| 589. | methyl | 4-(2-fluoropyrrolidin-1-yl)-phenyl |
| 590. | methyl | 4-((S)-2-fluoropyrrolidin-1-yl)-phenyl |
| 591. | methyl | 4-((R)-2-fluoropyrrolidin-1-yl)-phenyl |
| 592. | methyl | 4-(3-fluoropyrrolidin-1-yl)-phenyl |
| 593. | methyl | 4-((S)-3-fluoropyrrolidin-1-yl)-phenyl |
| 594. | methyl | 4-((R)-3-fluoropyrrolidin-1-yl)-phenyl |
| 595. | methyl | 4-(2,2-difluoropyrrolidin-1-yl)-phenyl |
| 596. | methyl | 4-(3,3-difluoropyrrolidin-1-yl)-phenyl |
| 597. | methyl | 4-(2-methylpyrrolidin-1-yl)-phenyl |
| 598. | methyl | 4-((S)-2-methylpyrrolidin-1-yl)-phenyl |
| 599. | methyl | 4-((R)-2-methylpyrrolidin-1-yl)-phenyl |
| 600. | methyl | 4-(3-methylpyrrolidin-1-yl)-phenyl |
| 601. | methyl | 4-((S)-3-methylpyrrolidin-1-yl)-phenyl |
| 602. | methyl | 4-((R)-3-methylpyrrolidin-1-yl)-phenyl |
| 603. | methyl | 4-(1-methylpyrrolidin-2-yl)-phenyl |
| 604. | methyl | 4-((S)-1-methylpyrrolidin-2-yl)-phenyl |
| 605. | methyl | 4-((R)-1-methylpyrrolidin-2-yl)-phenyl |
| 606. | methyl | 4-(1-methylpyrrolidin-3-yl)-phenyl |
| 607. | methyl | 4-((S)-1-methylpyrrolidin-3-yl)-phenyl |
| 608. | methyl | 4-((R)-1-methylpyrrolidin-3-yl)-phenyl |
| 609. | methyl | 4-(2,2-dimethylpyrrolidin-1-yl)-phenyl |
| 610. | methyl | 4-(3,3-dimethylpyrrolidin-1-yl)-phenyl |
| 611. | methyl | 4-(2-trifluoromethylpyrrolidin-1-yl)-phenyl |
| 612. | methyl | 4-((S)-2-trifluoromethylpyrrolidin-1-yl)-phenyl |
| 613. | methyl | 4-((R)-2-trifluoromethylpyrrolidin-1-yl)-phenyl |
| 614. | methyl | 4-(3-trifluoromethylpyrrolidin-1-yl)-phenyl |
| 615. | methyl | 4-((S)-3-trifluoromethylpyrrolidin-1-yl)-phenyl |
| 616. | methyl | 4-((R)-3-trifluoromethylpyrrolidin-1-yl)-phenyl |
| 617. | methyl | 4-(2-oxopyrrolidin-1-yl)-phenyl |
| 618. | methyl | 4-(2-oxo-oxazolidin-3-yl)-phenyl |
| 619. | methyl | 4-(piperidin-1-yl)-phenyl |
| 620. | methyl | 4-(2-methylpiperidin-1-yl)-phenyl |
| 621. | methyl | 4-((S)-2-methylpiperidin-1-yl)-phenyl |
| 622. | methyl | 4-((R)-2-methylpiperidin-1-yl)-phenyl |
| 623. | methyl | 4-(piperazin-1-yl)-phenyl |
| 624. | methyl | 4-(4-methylpiperazin-1-yl)-phenyl |
| 625. | methyl | 4-(morpholin-4-yl)-phenyl |
| 626. | methyl | 4-(thiomorpholin-4-yl)-phenyl |
| 627. | methyl | 4-(1-oxo-thiomorpholin-4-yl)-phenyl |
| 628. | methyl | 4-(1,1-dioxo-thiomorpholin-4-yl)-phenyl |
| 629. | methyl | 4-(pyrrol-1-yl)-phenyl |
| 630. | methyl | 4-(pyrrol-2-yl)-phenyl |
| 631. | methyl | 4-(pyrrol-3-yl)-phenyl |
| 632. | methyl | 4-(1-methylpyrrol-2-yl)-phenyl |
| 633. | methyl | 4-(1-methylpyrrol-3-yl)-phenyl |
| 634. | methyl | 4-(furan-2-yl)-phenyl |
| 635. | methyl | 4-(furan-3-yl)-phenyl |
| 636. | methyl | 4-(thiophen-2-yl)-phenyl |
| 637. | methyl | 4-(thiophen-3-yl)-phenyl |
| 638. | methyl | 4-(5-propylthien-2-yl)-phenyl |
| 639. | methyl | 4-(pyrazol-1-yl)-phenyl |
| 640. | methyl | 4-(pyrazol-3-yl)-phenyl |
| 641. | methyl | 4-(pyrazol-4-yl)-phenyl |
| 642. | methyl | 4-(1-methyl-1H-pyrazol-4-yl)-phenyl |
| 643. | methyl | 4-(1-ethyl-1H-pyrazol-4-yl)-phenyl |
| 644. | methyl | 4-(1-methyl-1H-pyrazol-5-yl)-phenyl |
| 645. | methyl | 4-(1H-imidazol-2-yl)-phenyl |
| 646. | methyl | 4-(imidazol-1-yl)-phenyl |
| 647. | methyl | 4-(1-methylimidazol-2-yl)-phenyl |
| 648. | methyl | 4-(oxazol-2-yl)-phenyl |
| 649. | methyl | 4-(oxazol-4-yl)-phenyl |
| 650. | methyl | 4-(oxazol-5-yl)-phenyl |
| 651. | methyl | 4-(isoxazol-3-yl)-phenyl |
| 652. | methyl | 4-(isoxazol-4-yl)-phenyl |
| 653. | methyl | 4-(isoxazol-5-yl)-phenyl |
| 654. | methyl | 4-([1,2,3]-triazol-1-yl)-phenyl |
| 655. | methyl | 4-([1,2,4]-triazol-1-yl)-phenyl |
| 656. | methyl | 4-([1,2,3]-triazol-2-yl)-phenyl |
| 657. | methyl | 4-(4H-[1,2,4]-triazol-3-yl)-phenyl |
| 658. | methyl | 4-([1,2,4]-triazol-4-yl)-phenyl |
| 659. | methyl | 4-(2H-[1,2,3]-triazol-4-yl)-phenyl |
| 660. | methyl | 4-(4-methyl-4H-[1,2,4]-triazol-3-yl)-phenyl |
| 661. | methyl | 4-(2-methyl-2H-[1,2,3]-triazol-4-yl)-phenyl |
| 662. | methyl | 4-([1,3,4]-oxadiazol-2-yl)-phenyl |
| 663. | methyl | 4-([1,2,4]-oxadiazol-3-yl)-phenyl |
| 664. | methyl | 4-([1,2,4]-oxadiazol-5-yl)-phenyl |
| 665. | methyl | 4-([1,2,3]-oxadiazol-4-yl)-phenyl |
| 666. | methyl | 4-([1,2,3]-oxadiazol-5-yl)-phenyl |
| 667. | methyl | 4-([1,2,3]-thiadiazol-4-yl)-phenyl |
| 668. | methyl | 4-(1H-tetrazol-5-yl)-phenyl |
| 669. | methyl | 4-(tetrazol-1-yl)-phenyl |
| 670. | methyl | 4-(2-methyl-2H-tetrazol-5-yl)-phenyl |
| 671. | methyl | 4-(1-methyl-1H-tetrazol-5-yl)-phenyl |
| 672. | methyl | 4-furazan-3-yl-phenyl |
| 673. | methyl | 4-(pyrid-2-yl)-phenyl |
| 674. | methyl | 4-(pyrid-3-yl)-phenyl |
| 675. | methyl | 4-(pyrid-4-yl)-phenyl |
| 676. | methyl | 4-(pyrimidin-2-yl)-phenyl |
| 677. | methyl | 4-(pyrimidin-4-yl)-phenyl |
| 678. | methyl | 4-(pyrimidin-5-yl)-phenyl |
| 679. | methyl | 5-isopropylthiophen-2-yl |
| 680. | methyl | 2-chlorothiophen-5-yl |
| 681. | methyl | 2,5-dichlorothiophen-4-yl |
| 682. | methyl | 2,3-dichlorothiophen-5-yl |
| 683. | methyl | 2-chloro-3-nitrothiophen-5-yl |
| 684. | methyl | 2-(phenylsulfonyl)-thiophen-5-yl |
| 685. | methyl | 2-(pyridin-2-yl)thiophen-5-yl |
| 686. | methyl | 2-(5-(trifluoromethyl)isoxazol-3-yl)-thiophen-5-yl |
| 687. | methyl | 2-(2-methylthiazol-4-yl)-thiophen-5-yl |
| 688. | methyl | 1-methyl-1H-imidazol-4-yl |
| 689. | methyl | 1,2-dimethyl-1H-imidazol-4-yl |
| 690. | methyl | 3,5-dimethylisoxazol-4-yl |
| 691. | methyl | thiazol-2-yl |
| 692. | methyl | 4-methylthiazol-2-yl |
| 693. | methyl | 4-isopropylthiazol-2-yl |
| 694. | methyl | 4-trifluoromethylthiazol-2-yl |
| 695. | methyl | 5-methylthiazol-2-yl |
| 696. | methyl | 5-isopropylthiazol-2-yl |
| 697. | methyl | 5-trifluoromethylthiazol-2-yl |
| 698. | methyl | 2,4-dimethylthiazol-5-yl |
| 699. | methyl | 2-acetamido-4-methylthiazol-5-yl |
| 700. | methyl | 4H-[1,2,4]triazol-3-yl |
| 701. | methyl | 5-methyl-4H-[1,2,4]triazol-3-yl |

TABLE A-continued

| No. | R¹ | Ar |
|---|---|---|
| 702. | methyl | 4-methyl-4H-[1,2,4]triazol-3-yl |
| 703. | methyl | 5-isopropyl-4H-[1,2,4]triazol-3-yl |
| 704. | methyl | 5-trifluoromethyl-4H-[1,2,4]triazol-3-yl |
| 705. | methyl | 4,5-dimethyl-4H-[1,2,4]triazol-3-yl |
| 706. | methyl | 5-isopropyl-4-methyl-4H-[1,2,4]triazol-3-yl |
| 707. | methyl | 5-trifluoromethyl-4-methyl-4H-[1,2,4]triazol-3-yl |
| 708. | methyl | [1,3,4]thiadiazol-2-yl |
| 709. | methyl | 5-methyl-[1,3,4]thiadiazol-2-yl |
| 710. | methyl | 5-isopropyl-[1,3,4]thiadiazol-2-yl |
| 711. | methyl | 5-trifluoromethyl-[1,3,4]thiadiazol-2-yl |
| 712. | methyl | 3-bromo-2-chloropyrid-5-yl |
| 713. | methyl | 2-(4-morpholino)-pyrid-5-yl |
| 714. | methyl | 2-phenoxypyrid-5-yl |
| 715. | methyl | (2-isopropyl)-pyrimidin-5-yl |
| 716. | methyl | (5-isopropyl)-pyrimidin-2-yl |
| 717. | methyl | 8-quinolyl |
| 718. | methyl | 5-isoquinolyl |
| 719. | methyl | 2-(trifluoroacetyl)-1,2,3,4-tetrahydroisoquinolin-7-yl |
| 720. | methyl | 5-chloro-3-methylbenzothiophen-2-yl |
| 721. | methyl | 3,4-dihydro-4-methyl-2H-benzo[b][1,4]oxazinyl |
| 722. | methyl | benzothiazol-6-yl |
| 723. | methyl | benzo[2,1,3]oxadiazol-4-yl |
| 724. | methyl | 5-chlorobenzo[2,1,3]oxadiazol-4-yl |
| 725. | methyl | 7-chlorobenzo[2,1,3]oxadiazol-4-yl |
| 726. | methyl | benzo[2,1,3]thiadiazol-4-yl |
| 727. | H | 4-methylphenyl |
| 728. | H | 4-ethylphenyl |
| 729. | H | 4-propylphenyl |
| 730. | H | 4-isopropylphenyl |
| 731. | H | 4-sec-butylphenyl |
| 732. | H | 4-isobutylphenyl |
| 733. | H | 4-(1,1-dimethylpropyl)-phenyl |
| 734. | H | 4-vinylphenyl |
| 735. | H | 4-isopropenylphenyl |
| 736. | H | 4-fluorophenyl |
| 737. | H | 4-chlorophenyl |
| 738. | H | 4-bromophenyl |
| 739. | H | 4-(fluoromethyl)phenyl |
| 740. | H | 3-(fluoromethyl)phenyl |
| 741. | H | 2-(fluoromethyl)phenyl |
| 742. | H | 4-(difluoromethyl)phenyl |
| 743. | H | 3-(difluoromethyl)phenyl |
| 744. | H | 2-(difluoromethyl)phenyl |
| 745. | H | 4-(trifluoromethyl)phenyl |
| 746. | H | 3-(trifluoromethyl)phenyl |
| 747. | H | 2-(trifluoromethyl)phenyl |
| 748. | H | 4-(1-fluoroethyl)-phenyl |
| 749. | H | 4-((S)-1-fluoroethyl)-phenyl |
| 750. | H | 4-((R)-1-fluoroethyl)-phenyl |
| 751. | H | 4-(2-fluoroethyl)-phenyl |
| 752. | H | 4-(1,1-difluoroethyl)-phenyl |
| 753. | H | 4-(2,2-difluoroethyl)-phenyl |
| 754. | H | 4-(2,2,2-trifluoroethyl)-phenyl |
| 755. | H | 4-(3-fluoropropyl)-phenyl |
| 756. | H | 4-(2-fluoropropyl)-phenyl |
| 757. | H | 4-((S)-2-fluoropropyl)-phenyl |
| 758. | H | 4-((R)-2-fluoropropyl)-phenyl |
| 759. | H | 4-(3,3-difluoropropyl)-phenyl |
| 760. | H | 4-(3,3,3-trifluoropropyl)-phenyl |
| 761. | H | 4-(1-fluoro-1-methylethyl)-phenyl |
| 762. | H | 4-(2-fluoro-1-methylethyl)-phenyl |
| 763. | H | 4-((S)-2-fluoro-1-methylethyl)-phenyl |
| 764. | H | 4-((R)-2-fluoro-1-methylethyl)-phenyl |
| 765. | H | 4-(2,2-difluoro-1-methylethyl)-phenyl |
| 766. | H | 4-((S)-2,2-difluoro-1-methylethyl)-phenyl |
| 767. | H | 4-((R)-2,2-difluoro-1-methylethyl)-phenyl |
| 768. | H | 4-(2,2,2-trifluoro-1-methylethyl)-phenyl |
| 769. | H | 4-((S)-2,2,2-trifluoro-1-methylethyl)-phenyl |
| 770. | H | 4-((R)-2,2,2-trifluoro-1-methylethyl)-phenyl |
| 771. | H | 4-(2-fluoro-1-fluoromethylethyl)-phenyl |
| 772. | H | 4-(1-difluoromethyl-2,2-difluoroethyl)-phenyl |
| 773. | H | 4-(1,1-dimethyl-2-fluoroethyl)-phenyl |
| 774. | H | 4-methoxyphenyl |
| 775. | H | 4-ethoxyphenyl |
| 776. | H | 4-propoxyphenyl |
| 777. | H | 4-isopropoxyphenyl |
| 778. | H | 4-butoxyphenyl |
| 779. | H | 4-(fluoromethoxy)-phenyl |
| 780. | H | 4-(difluoromethoxy)-phenyl |
| 781. | H | 4-(trifluoromethoxy)-phenyl |
| 782. | H | 3-(trifluoromethoxy)-phenyl |
| 783. | H | 4-(2-fluoroethoxy)-phenyl |
| 784. | H | 4-(2,2-difluoroethoxy)-phenyl |
| 785. | H | 4-(2,2,2-trifluoroethoxy)-phenyl |
| 786. | H | 4-(1,1,2,2-tetrafluoroethoxy)-phenyl |
| 787. | H | 4-cyclopropylphenyl |
| 788. | H | 4-cyclobutylphenyl |
| 789. | H | 4-cyclopentylphenyl |
| 790. | H | 4-(2,2-difluorocyclopropyl)-phenyl |
| 791. | H | 3,4-difluorophenyl |
| 792. | H | 4-bromo-3-fluorophenyl |
| 793. | H | 4-bromo-2-fluorophenyl |
| 794. | H | 4-bromo-2,5-difluorophenyl |
| 795. | H | 2-fluoro-4-isopropylphenyl |
| 796. | H | 3-fluoro-4-isopropylphenyl |
| 797. | H | 4-(1-hydroxy-1-methylethyl)-phenyl |
| 798. | H | 4-(2-hydroxy-2-methylpropyl)-phenyl |
| 799. | H | 4-acetylphenyl |
| 800. | H | 4-carboxyphenyl |
| 801. | H | 4-cyanophenyl |
| 802. | H | 4-hydroxyphenyl |
| 803. | H | 4-(O-benzyl)-phenyl |
| 804. | H | 4-(2-methoxyethoxy)-phenyl |
| 805. | H | 4-(CH$_2$—N(CH$_3$)$_2$)-phenyl |
| 806. | H | 4-(NH—CO—NH$_2$)-phenyl |
| 807. | H | 4-(methylsulfanyl)-phenyl |
| 808. | H | 4-(fluoromethylsulfanyl)-phenyl |
| 809. | H | 4-(difluoromethylsulfanyl)-phenyl |
| 810. | H | 4-(trifluoromethylsulfanyl)-phenyl |
| 811. | H | 4-(methylsulfonyl)-phenyl |
| 812. | H | 4-(N-methoxy-N-methyl-amino)-phenyl |
| 813. | H | 4-(methoxyamino)-phenyl |
| 814. | H | 4-(ethoxyamino)-phenyl |
| 815. | H | 4-(N-methylaminooxy)-phenyl |
| 816. | H | 4-(N,N-dimethylaminooxy)-phenyl |
| 817. | H | 4-(azetidin-1-yl)-phenyl |
| 818. | H | 4-(2-methylazetidin-1-yl)-phenyl |
| 819. | H | 4-((S)-2-methylazetidin-1-yl)-phenyl |
| 820. | H | 4-((R)-2-methylazetidin-1-yl)-phenyl |
| 821. | H | 4-(3-fluoroazetidin-1-yl)-phenyl |
| 822. | H | 4-(3-methoxyazetidin-1-yl)-phenyl |
| 823. | H | 4-(3-hydroxyazetidin-1-yl)-phenyl |
| 824. | H | 4-(pyrrolidin-1-yl)-phenyl |
| 825. | H | 4-(pyrrolidin-2-yl)-phenyl |
| 826. | H | 4-((S)-pyrrolidin-2-yl)-phenyl |
| 827. | H | 4-((R)-pyrrolidin-2-yl)-phenyl |
| 828. | H | 4-(pyrrolidin-3-yl)-phenyl |
| 829. | H | 4-((S)-pyrrolidin-3-yl)-phenyl |
| 830. | H | 4-((R)-pyrrolidin-3-yl)-phenyl |
| 831. | H | 4-(2-fluoropyrrolidin-1-yl)-phenyl |
| 832. | H | 4-((S)-2-fluoropyrrolidin-1-yl)-phenyl |
| 833. | H | 4-((R)-2-fluoropyrrolidin-1-yl)-phenyl |
| 834. | H | 4-(3-fluoropyrrolidin-1-yl)-phenyl |
| 835. | H | 4-((S)-3-fluoropyrrolidin-1-yl)-phenyl |
| 836. | H | 4-((R)-3-fluoropyrrolidin-1-yl)-phenyl |
| 837. | H | 4-(2,2-difluoropyrrolidin-1-yl)-phenyl |
| 838. | H | 4-(3,3-difluoropyrrolidin-1-yl)-phenyl |
| 839. | H | 4-(2-methylpyrrolidin-1-yl)-phenyl |
| 840. | H | 4-((S)-2-methylpyrrolidin-1-yl)-phenyl |
| 841. | H | 4-((R)-2-methylpyrrolidin-1-yl)-phenyl |
| 842. | H | 4-(3-methylpyrrolidin-1-yl)-phenyl |
| 843. | H | 4-((S)-3-methylpyrrolidin-1-yl)-phenyl |
| 844. | H | 4-((R)-3-methylpyrrolidin-1-yl)-phenyl |
| 845. | H | 4-(1-methylpyrrolidin-2-yl)-phenyl |
| 846. | H | 4-((S)-1-methylpyrrolidin-2-yl)-phenyl |
| 847. | H | 4-((R)-1-methylpyrrolidin-2-yl)-phenyl |
| 848. | H | 4-(1-methylpyrrolidin-3-yl)-phenyl |
| 849. | H | 4-((S)-1-methylpyrrolidin-3-yl)-phenyl |
| 850. | H | 4-((R)-1-methylpyrrolidin-3-yl)-phenyl |
| 851. | H | 4-(2,2-dimethylpyrrolidin-1-yl)-phenyl |
| 852. | H | 4-(3,3-dimethylpyrrolidin-1-yl)-phenyl |
| 853. | H | 4-(2-trifluoromethylpyrrolidin-1-yl)-phenyl |

TABLE A-continued

| No. | R¹ | Ar |
|---|---|---|
| 854. | H | 4-((S)-2-trifluoromethylpyrrolidin-1-yl)-phenyl |
| 855. | H | 4-((R)-2-trifluoromethylpyrrolidin-1-yl)-phenyl |
| 856. | H | 4-(3-trifluoromethylpyrrolidin-1-yl)-phenyl |
| 857. | H | 4-((S)-3-trifluoromethylpyrrolidin-1-yl)-phenyl |
| 858. | H | 4-((R)-3-trifluoromethylpyrrolidin-1-yl)-phenyl |
| 859. | H | 4-(2-oxopyrrolidin-1-yl)-phenyl |
| 860. | H | 4-(2-oxo-oxazolidin-3-yl)-phenyl |
| 861. | H | 4-(piperidin-1-yl)-phenyl |
| 862. | H | 4-(2-methylpiperidin-1-yl)-phenyl |
| 863. | H | 4-((S)-2-methylpiperidin-1-yl)-phenyl |
| 864. | H | 4-((R)-2-methylpiperidin-1-yl)-phenyl |
| 865. | H | 4-(piperazin-1-yl)-phenyl |
| 866. | H | 4-(4-methylpiperazin-1-yl)-phenyl |
| 867. | H | 4-(morpholin-4-yl)-phenyl |
| 868. | H | 4-(thiomorpholin-4-yl)-phenyl |
| 869. | H | 4-(1-oxo-thiomorpholin-4-yl)-phenyl |
| 870. | H | 4-(1,1-dioxo-thiomorpholin-4-yl)-phenyl |
| 871. | H | 4-(pyrrol-1-yl)-phenyl |
| 872. | H | 4-(pyrrol-2-yl)-phenyl |
| 873. | H | 4-(pyrrol-3-yl)-phenyl |
| 874. | H | 4-(1-methylpyrrol-2-yl)-phenyl |
| 875. | H | 4-(1-methylpyrrol-3-yl)-phenyl |
| 876. | H | 4-(furan-2-yl)-phenyl |
| 877. | H | 4-(furan-3-yl)-phenyl |
| 878. | H | 4-(thiophen-2-yl)-phenyl |
| 879. | H | 4-(thiophen-3-yl)-phenyl |
| 880. | H | 4-(5-propylthien-2-yl)-phenyl |
| 881. | H | 4-(pyrazol-1-yl)-phenyl |
| 882. | H | 4-(pyrazol-3-yl)-phenyl |
| 883. | H | 4-(pyrazol-4-yl)-phenyl |
| 884. | H | 4-(1-methyl-1H-pyrazol-4-yl)-phenyl |
| 885. | H | 4-(1-ethyl-1H-pyrazol-4-yl)-phenyl |
| 886. | H | 4-(1-methyl-1H-pyrazol-5-yl)-phenyl |
| 887. | H | 4-(1H-imidazol-2-yl)-phenyl |
| 888. | H | 4-(imidazol-1-yl)-phenyl |
| 889. | H | 4-(1-methylimidazol-2-yl)-phenyl |
| 890. | H | 4-(oxazol-2-yl)-phenyl |
| 891. | H | 4-(oxazol-4-yl)-phenyl |
| 892. | H | 4-(oxazol-5-yl)-phenyl |
| 893. | H | 4-(isoxazol-3-yl)-phenyl |
| 894. | H | 4-(isoxazol-4-yl)-phenyl |
| 895. | H | 4-(isoxazol-5-yl)-phenyl |
| 896. | H | 4-([1,2,3]-triazol-1-yl)-phenyl |
| 897. | H | 4-([1,2,4]-triazol-1-yl)-phenyl |
| 898. | H | 4-([1,2,3]-triazol-2-yl)-phenyl |
| 899. | H | 4-(4H-[1,2,4]-triazol-3-yl)-phenyl |
| 900. | H | 4-([1,2,4]-triazol-4-yl)-phenyl |
| 901. | H | 4-(2H-[1,2,3]-triazol-4-yl)-phenyl |
| 902. | H | 4-(4-methyl-4H-[1,2,4]-triazol-3-yl)-phenyl |
| 903. | H | 4-(2-methyl-2H-[1,2,3]-triazol-4-yl)-phenyl |
| 904. | H | 4-([1,3,4]-oxadiazol-2-yl)-phenyl |
| 905. | H | 4-([1,2,4]-oxadiazol-3-yl)-phenyl |
| 906. | H | 4-([1,2,4]-oxadiazol-5-yl)-phenyl |
| 907. | H | 4-([1,2,3]-oxadiazol-4-yl)-phenyl |
| 908. | H | 4-([1,2,3]-oxadiazol-5-yl)-phenyl |
| 909. | H | 4-([1,2,3]-thiadiazol-4-yl)-phenyl |
| 910. | H | 4-(1H-tetrazol-5-yl)-phenyl |
| 911. | H | 4-(tetrazol-1-yl)-phenyl |
| 912. | H | 4-(2-methyl-2H-tetrazol-5-yl)-phenyl |
| 913. | H | 4-(1-methyl-1H-tetrazol-5-yl)-phenyl |
| 914. | H | 4-furazan-3-yl-phenyl |
| 915. | H | 4-(pyrid-2-yl)-phenyl |
| 916. | H | 4-(pyrid-3-yl)-phenyl |
| 917. | H | 4-(pyrid-4-yl)-phenyl |
| 918. | H | 4-(pyrimidin-2-yl)-phenyl |
| 919. | H | 4-(pyrimidin-4-yl)-phenyl |
| 920. | H | 4-(pyrimidin-5-yl)-phenyl |
| 921. | H | 5-isopropylthiophen-2-yl |
| 922. | H | 2-chlorothiophen-5-yl |
| 923. | H | 2,5-dichlorothiophen-4-yl |
| 924. | H | 2,3-dichlorothiophen-5-yl |
| 925. | H | 2-chloro-3-nitrothiophen-5-yl |
| 926. | H | 2-(phenylsulfonyl)-thiophen-5-yl |
| 927. | H | 2-(pyridin-2-yl)thiophen-5-yl |
| 928. | H | 2-(5-(trifluoromethyl)isoxazol-3-yl)-thiophen-5-yl |
| 929. | H | 2-(2-methylthiazol-4-yl)-thiophen-5-yl |
| 930. | H | 1-methyl-1H-imidazol-4-yl |
| 931. | H | 1,2-dimethyl-1H-imidazol-4-yl |
| 932. | H | 3,5-dimethylisoxazol-4-yl |
| 933. | H | thiazol-2-yl |
| 934. | H | 4-methylthiazol-2-yl |
| 935. | H | 4-isopropylthiazol-2-yl |
| 936. | H | 4-trifluoromethylthiazol-2-yl |
| 937. | H | 5-methylthiazol-2-yl |
| 938. | H | 5-isopropylthiazol-2-yl |
| 939. | H | 5-trifluoromethylthiazol-2-yl |
| 940. | H | 2,4-dimethylthiazol-5-yl |
| 941. | H | 2-acetamido-4-methylthiazol-5-yl |
| 942. | H | 4H-[1,2,4]triazol-3-yl |
| 943. | H | 5-methyl-4H-[1,2,4]triazol-3-yl |
| 944. | H | 4-methyl-4H-[1,2,4]triazol-3-yl |
| 945. | H | 5-isopropyl-4H-[1,2,4]triazol-3-yl |
| 946. | H | 5-trifluoromethyl-4H-[1,2,4]triazol-3-yl |
| 947. | H | 4,5-dimethyl-4H-[1,2,4]triazol-3-yl |
| 948. | H | 5-isopropyl-4-methyl-4H-[1,2,4]triazol-3-yl |
| 949. | H | 5-trifluoromethyl-4-methyl-4H-[1,2,4]triazol-3-yl |
| 950. | H | [1,3,4]thiadiazol-2-yl |
| 951. | H | 5-methyl-[1,3,4]thiadiazol-2-yl |
| 952. | H | 5-isopropyl-[1,3,4]thiadiazol-2-yl |
| 953. | H | 5-trifluoromethyl-[1,3,4]thiadiazol-2-yl |
| 954. | H | 3-bromo-2-chloropyrid-5-yl |
| 955. | H | 2-(4-morpholino)-pyrid-5-yl |
| 956. | H | 2-phenoxypyrid-5-yl |
| 957. | H | (2-isopropyl)-pyrimidin-5-yl |
| 958. | H | (5-isopropyl)-pyrimidin-2-yl |
| 959. | H | 8-quinolyl |
| 960. | H | 5-isoquinolyl |
| 961. | H | 2-(trifluoroacetyl)-1,2,3,4-tetrahydroisoquinolin-7-yl |
| 962. | H | 5-chloro-3-methylbenzothiophen-2-yl |
| 963. | H | 3,4-dihydro-4-methyl-2H-benzo[b][1,4]oxazinyl |
| 964. | H | benzothiazol-6-yl |
| 965. | H | benzo[2,1,3]oxadiazol-4-yl |
| 966. | H | 5-chlorobenzo[2,1,3]oxadiazol-4-yl |
| 967. | H | 7-chlorobenzo[2,1,3]oxadiazol-4-yl |
| 968. | H | benzo[2,1,3]thiadiazol-4-yl |
| 969. | 3-fluoropropyl | 4-methylphenyl |
| 970. | 3-fluoropropyl | 4-ethylphenyl |
| 971. | 3-fluoropropyl | 4-propylphenyl |
| 972. | 3-fluoropropyl | 4-isopropylphenyl |
| 973. | 3-fluoropropyl | 4-sec-butylphenyl |
| 974. | 3-fluoropropyl | 4-isobutylphenyl |
| 975. | 3-fluoropropyl | 4-(1,1-dimethylpropyl)-phenyl |
| 976. | 3-fluoropropyl | 4-vinylphenyl |
| 977. | 3-fluoropropyl | 4-isopropenylphenyl |
| 978. | 3-fluoropropyl | 4-fluorophenyl |
| 979. | 3-fluoropropyl | 4-chlorophenyl |
| 980. | 3-fluoropropyl | 4-bromophenyl |
| 981. | 3-fluoropropyl | 4-(fluoromethyl)phenyl |
| 982. | 3-fluoropropyl | 3-(fluoromethyl)phenyl |
| 983. | 3-fluoropropyl | 2-(fluoromethyl)phenyl |
| 984. | 3-fluoropropyl | 4-(difluoromethyl)phenyl |
| 985. | 3-fluoropropyl | 3-(difluoromethyl)phenyl |
| 986. | 3-fluoropropyl | 2-(difluoromethyl)phenyl |
| 987. | 3-fluoropropyl | 4-(trifluoromethyl)phenyl |
| 988. | 3-fluoropropyl | 3-(trifluoromethyl)phenyl |
| 989. | 3-fluoropropyl | 2-(trifluoromethyl)phenyl |
| 990. | 3-fluoropropyl | 4-(1-fluoroethyl)-phenyl |
| 991. | 3-fluoropropyl | 4-((S)-1-fluoroethyl)-phenyl |
| 992. | 3-fluoropropyl | 4-((R)-1-fluoroethyl)-phenyl |
| 993. | 3-fluoropropyl | 4-(2-fluoroethyl)-phenyl |
| 994. | 3-fluoropropyl | 4-(1,1-difluoroethyl)-phenyl |
| 995. | 3-fluoropropyl | 4-(2,2-difluoroethyl)-phenyl |
| 996. | 3-fluoropropyl | 4-(2,2,2-trifluoroethyl)-phenyl |
| 997. | 3-fluoropropyl | 4-(3-fluoropropyl)-phenyl |
| 998. | 3-fluoropropyl | 4-(2-fluoropropyl)-phenyl |
| 999. | 3-fluoropropyl | 4-((S)-2-fluoropropyl)-phenyl |
| 1000. | 3-fluoropropyl | 4-((R)-2-fluoropropyl)-phenyl |
| 1001. | 3-fluoropropyl | 4-(3,3-difluoropropyl)-phenyl |

TABLE A-continued

| No. | R¹ | Ar |
|---|---|---|
| 1002. | 3-fluoropropyl | 4-(3,3,3-trifluoropropyl)-phenyl |
| 1003. | 3-fluoropropyl | 4-(1-fluoro-1-methylethyl)-phenyl |
| 1004. | 3-fluoropropyl | 4-(2-fluoro-1-methylethyl)-phenyl |
| 1005. | 3-fluoropropyl | 4-((S)-2-fluoro-1-methylethyl)-phenyl |
| 1006. | 3-fluoropropyl | 4-((R)-2-fluoro-1-methylethyl)-phenyl |
| 1007. | 3-fluoropropyl | 4-(2,2-difluoro-1-methylethyl)-phenyl |
| 1008. | 3-fluoropropyl | 4-((S)-2,2-difluoro-1-methylethyl)-phenyl |
| 1009. | 3-fluoropropyl | 4-((R)-2,2-difluoro-1-methylethyl)-phenyl |
| 1010. | 3-fluoropropyl | 4-(2,2,2-trifluoro-1-methylethyl)-phenyl |
| 1011. | 3-fluoropropyl | 4-((S)-2,2,2-trifluoro-1-methylethyl)-phenyl |
| 1012. | 3-fluoropropyl | 4-((R)-2,2,2-trifluoro-1-methylethyl)-phenyl |
| 1013. | 3-fluoropropyl | 4-(2-fluoro-1-fluoromethylethyl)-phenyl |
| 1014. | 3-fluoropropyl | 4-(1-difluoromethyl-2,2-difluoroethyl)-phenyl |
| 1015. | 3-fluoropropyl | 4-(1,1-dimethyl-2-fluoroethyl)-phenyl |
| 1016. | 3-fluoropropyl | 4-methoxyphenyl |
| 1017. | 3-fluoropropyl | 4-ethoxyphenyl |
| 1018. | 3-fluoropropyl | 4-propoxyphenyl |
| 1019. | 3-fluoropropyl | 4-isopropoxyphenyl |
| 1020. | 3-fluoropropyl | 4-butoxyphenyl |
| 1021. | 3-fluoropropyl | 4-(fluoromethoxy)-phenyl |
| 1022. | 3-fluoropropyl | 4-(difluoromethoxy)-phenyl |
| 1023. | 3-fluoropropyl | 4-(trifluoromethoxy)-phenyl |
| 1024. | 3-fluoropropyl | 3-(trifluoromethoxy)-phenyl |
| 1025. | 3-fluoropropyl | 4-(2-fluoroethoxy)-phenyl |
| 1026. | 3-fluoropropyl | 4-(2,2-difluoroethoxy)-phenyl |
| 1027. | 3-fluoropropyl | 4-(2,2,2-trifluoroethoxy)-phenyl |
| 1028. | 3-fluoropropyl | 4-(1,1,2,2-tetrafluoroethoxy)-phenyl |
| 1029. | 3-fluoropropyl | 4-cyclopropylphenyl |
| 1030. | 3-fluoropropyl | 4-cyclobutylphenyl |
| 1031. | 3-fluoropropyl | 4-cyclopentylphenyl |
| 1032. | 3-fluoropropyl | 4-(2,2-difluorocyclopropyl)-phenyl |
| 1033. | 3-fluoropropyl | 3,4-difluorophenyl |
| 1034. | 3-fluoropropyl | 4-bromo-3-fluorophenyl |
| 1035. | 3-fluoropropyl | 4-bromo-2-fluorophenyl |
| 1036. | 3-fluoropropyl | 4-bromo-2,5-difluorophenyl |
| 1037. | 3-fluoropropyl | 2-fluoro-4-isopropylphenyl |
| 1038. | 3-fluoropropyl | 3-fluoro-4-isopropylphenyl |
| 1039. | 3-fluoropropyl | 4-(1-hydroxy-1-methylethyl)-phenyl |
| 1040. | 3-fluoropropyl | 4-(2-hydroxy-2-methylpropyl)-phenyl |
| 1041. | 3-fluoropropyl | 4-acetylphenyl |
| 1042. | 3-fluoropropyl | 4-carboxyphenyl |
| 1043. | 3-fluoropropyl | 4-cyanophenyl |
| 1044. | 3-fluoropropyl | 4-hydroxyphenyl |
| 1045. | 3-fluoropropyl | 4-(O-benzyl)-phenyl |
| 1046. | 3-fluoropropyl | 4-(2-methoxyethoxy)-phenyl |
| 1047. | 3-fluoropropyl | 4-(CH₂—N(CH₃)₂)-phenyl |
| 1048. | 3-fluoropropyl | 4-(NH—CO—NH₂)-phenyl |
| 1049. | 3-fluoropropyl | 4-(methylsulfanyl)-phenyl |
| 1050. | 3-fluoropropyl | 4-(fluoromethylsulfanyl)-phenyl |
| 1051. | 3-fluoropropyl | 4-(difluoromethylsulfanyl)-phenyl |
| 1052. | 3-fluoropropyl | 4-(trifluoromethylsulfanyl)-phenyl |
| 1053. | 3-fluoropropyl | 4-(methylsulfonyl)-phenyl |
| 1054. | 3-fluoropropyl | 4-(N-methoxy-N-methyl-amino)-phenyl |
| 1055. | 3-fluoropropyl | 4-(methoxyamino)-phenyl |
| 1056. | 3-fluoropropyl | 4-(ethoxyamino)-phenyl |
| 1057. | 3-fluoropropyl | 4-(N-methylaminooxy)-phenyl |
| 1058. | 3-fluoropropyl | 4-(N,N-dimethylaminooxy)-phenyl |
| 1059. | 3-fluoropropyl | 4-(azetidin-1-yl)-phenyl |
| 1060. | 3-fluoropropyl | 4-(2-methylazetidin-1-yl)-phenyl |
| 1061. | 3-fluoropropyl | 4-((S)-2-methylazetidin-1-yl)-phenyl |
| 1062. | 3-fluoropropyl | 4-((R)-2-methylazetidin-1-yl)-phenyl |
| 1063. | 3-fluoropropyl | 4-(3-fluoroazetidin-1-yl)-phenyl |
| 1064. | 3-fluoropropyl | 4-(3-methoxyazetidin-1-yl)-phenyl |
| 1065. | 3-fluoropropyl | 4-(3-hydroxyazetidin-1-yl)-phenyl |
| 1066. | 3-fluoropropyl | 4-(pyrrolidin-1-yl)-phenyl |
| 1067. | 3-fluoropropyl | 4-(pyrrolidin-2-yl)-phenyl |
| 1068. | 3-fluoropropyl | 4-((S)-pyrrolidin-2-yl)-phenyl |
| 1069. | 3-fluoropropyl | 4-((R)-pyrrolidin-2-yl)-phenyl |
| 1070. | 3-fluoropropyl | 4-(pyrrolidin-3-yl)-phenyl |
| 1071. | 3-fluoropropyl | 4-((S)-pyrrolidin-3-yl)-phenyl |
| 1072. | 3-fluoropropyl | 4-((R)-pyrrolidin-3-yl)-phenyl |
| 1073. | 3-fluoropropyl | 4-(2-fluoropyrrolidin-1-yl)-phenyl |
| 1074. | 3-fluoropropyl | 4-((S)-2-fluoropyrrolidin-1-yl)-phenyl |
| 1075. | 3-fluoropropyl | 4-((R)-2-fluoropyrrolidin-1-yl)-phenyl |
| 1076. | 3-fluoropropyl | 4-(3-fluoropyrrolidin-1-yl)-phenyl |
| 1077. | 3-fluoropropyl | 4-((S)-3-fluoropyrrolidin-1-yl)-phenyl |
| 1078. | 3-fluoropropyl | 4-((R)-3-fluoropyrrolidin-1-yl)-phenyl |
| 1079. | 3-fluoropropyl | 4-(2,2-difluoropyrrolidin-1-yl)-phenyl |
| 1080. | 3-fluoropropyl | 4-(3,3-difluoropyrrolidin-1-yl)-phenyl |
| 1081. | 3-fluoropropyl | 4-(2-methylpyrrolidin-1-yl)-phenyl |
| 1082. | 3-fluoropropyl | 4-((S)-2-methylpyrrolidin-1-yl)-phenyl |
| 1083. | 3-fluoropropyl | 4-((R)-2-methylpyrrolidin-1-yl)-phenyl |
| 1084. | 3-fluoropropyl | 4-(3-methylpyrrolidin-1-yl)-phenyl |
| 1085. | 3-fluoropropyl | 4-((S)-3-methylpyrrolidin-1-yl)-phenyl |
| 1086. | 3-fluoropropyl | 4-((R)-3-methylpyrrolidin-1-yl)-phenyl |
| 1087. | 3-fluoropropyl | 4-(1-methylpyrrolidin-2-yl)-phenyl |
| 1088. | 3-fluoropropyl | 4-((S)-1-methylpyrrolidin-2-yl)-phenyl |
| 1089. | 3-fluoropropyl | 4-((R)-1-methylpyrrolidin-2-yl)-phenyl |
| 1090. | 3-fluoropropyl | 4-(1-methylpyrrolidin-3-yl)-phenyl |
| 1091. | 3-fluoropropyl | 4-((S)-1-methylpyrrolidin-3-yl)-phenyl |
| 1092. | 3-fluoropropyl | 4-((R)-1-methylpyrrolidin-3-yl)-phenyl |
| 1093. | 3-fluoropropyl | 4-(2,2-dimethylpyrrolidin-1-yl)-phenyl |
| 1094. | 3-fluoropropyl | 4-(3,3-dimethylpyrrolidin-1-yl)-phenyl |
| 1095. | 3-fluoropropyl | 4-(2-trifluoromethylpyrrolidin-1-yl)-phenyl |
| 1096. | 3-fluoropropyl | 4-((S)-2-trifluoromethylpyrrolidin-1-yl)-phenyl |
| 1097. | 3-fluoropropyl | 4-((R)-2-trifluoromethylpyrrolidin-1-yl)-phenyl |
| 1098. | 3-fluoropropyl | 4-(3-trifluoromethylpyrrolidin-1-yl)-phenyl |
| 1099. | 3-fluoropropyl | 4-((S)-3-trifluoromethylpyrrolidin-1-yl)-phenyl |
| 1100. | 3-fluoropropyl | 4-((R)-3-trifluoromethylpyrrolidin-1-yl)-phenyl |
| 1101. | 3-fluoropropyl | 4-(2-oxopyrrolidin-1-yl)-phenyl |
| 1102. | 3-fluoropropyl | 4-(2-oxo-oxazolidin-3-yl)-phenyl |
| 1103. | 3-fluoropropyl | 4-(piperidin-1-yl)-phenyl |
| 1104. | 3-fluoropropyl | 4-(2-methylpiperidin-1-yl)-phenyl |
| 1105. | 3-fluoropropyl | 4-((S)-2-methylpiperidin-1-yl)-phenyl |
| 1106. | 3-fluoropropyl | 4-((R)-2-methylpiperidin-1-yl)-phenyl |
| 1107. | 3-fluoropropyl | 4-(piperazin-1-yl)-phenyl |
| 1108. | 3-fluoropropyl | 4-(4-methylpiperazin-1-yl)-phenyl |
| 1109. | 3-fluoropropyl | 4-(morpholin-4-yl)-phenyl |
| 1110. | 3-fluoropropyl | 4-(thiomorpholin-4-yl)-phenyl |
| 1111. | 3-fluoropropyl | 4-(1-oxo-thiomorpholin-4-yl)-phenyl |
| 1112. | 3-fluoropropyl | 4-(1,1-dioxo-thiomorpholin-4-yl)-phenyl |
| 1113. | 3-fluoropropyl | 4-(pyrrol-1-yl)-phenyl |
| 1114. | 3-fluoropropyl | 4-(pyrrol-2-yl)-phenyl |
| 1115. | 3-fluoropropyl | 4-(pyrrol-3-yl)-phenyl |
| 1116. | 3-fluoropropyl | 4-(1-methylpyrrol-2-yl)-phenyl |
| 1117. | 3-fluoropropyl | 4-(1-methylpyrrol-3-yl)-phenyl |
| 1118. | 3-fluoropropyl | 4-(furan-2-yl)-phenyl |
| 1119. | 3-fluoropropyl | 4-(furan-3-yl)-phenyl |
| 1120. | 3-fluoropropyl | 4-(thiophen-2-yl)-phenyl |
| 1121. | 3-fluoropropyl | 4-(thiophen-3-yl)-phenyl |
| 1122. | 3-fluoropropyl | 4-(5-propylthien-2-yl)-phenyl |
| 1123. | 3-fluoropropyl | 4-(pyrazol-1-yl)-phenyl |
| 1124. | 3-fluoropropyl | 4-(pyrazol-3-yl)-phenyl |
| 1125. | 3-fluoropropyl | 4-(pyrazol-4-yl)-phenyl |
| 1126. | 3-fluoropropyl | 4-(1-methyl-1H-pyrazol-4-yl)-phenyl |
| 1127. | 3-fluoropropyl | 4-(1-ethyl-1H-pyrazol-4-yl)-phenyl |
| 1128. | 3-fluoropropyl | 4-(1-methyl-1H-pyrazol-5-yl)-phenyl |
| 1129. | 3-fluoropropyl | 4-(1H-imidazol-2-yl)-phenyl |
| 1130. | 3-fluoropropyl | 4-(imidazol-1-yl)-phenyl |
| 1131. | 3-fluoropropyl | 4-(1-methylimidazol-2-yl)-phenyl |
| 1132. | 3-fluoropropyl | 4-(oxazol-2-yl)-phenyl |
| 1133. | 3-fluoropropyl | 4-(oxazol-4-yl)-phenyl |
| 1134. | 3-fluoropropyl | 4-(oxazol-5-yl)-phenyl |
| 1135. | 3-fluoropropyl | 4-(isoxazol-3-yl)-phenyl |
| 1136. | 3-fluoropropyl | 4-(isoxazol-4-yl)-phenyl |
| 1137. | 3-fluoropropyl | 4-(isoxazol-5-yl)-phenyl |
| 1138. | 3-fluoropropyl | 4-([1,2,3]-triazol-1-yl)-phenyl |
| 1139. | 3-fluoropropyl | 4-([1,2,4]-triazol-1-yl)-phenyl |
| 1140. | 3-fluoropropyl | 4-([1,2,3]-triazol-2-yl)-phenyl |
| 1141. | 3-fluoropropyl | 4-(4H-[1,2,4]-triazol-3-yl)-phenyl |
| 1142. | 3-fluoropropyl | 4-([1,2,4]-triazol-4-yl)-phenyl |
| 1143. | 3-fluoropropyl | 4-(2H-[1,2,3]-triazol-4-yl)-phenyl |
| 1144. | 3-fluoropropyl | 4-(4-methyl-4H-[1,2,4]-triazol-3-yl)-phenyl |
| 1145. | 3-fluoropropyl | 4-(2-methyl-2H-[1,2,3]-triazol-4-yl)-phenyl |
| 1146. | 3-fluoropropyl | 4-([1,3,4]-oxadiazol-2-yl)-phenyl |
| 1147. | 3-fluoropropyl | 4-([1,2,4]-oxadiazol-3-yl)-phenyl |
| 1148. | 3-fluoropropyl | 4-([1,2,4]-oxadiazol-5-yl)-phenyl |
| 1149. | 3-fluoropropyl | 4-([1,2,3]-oxadiazol-4-yl)-phenyl |
| 1150. | 3-fluoropropyl | 4-([1,2,3]-oxadiazol-5-yl)-phenyl |
| 1151. | 3-fluoropropyl | 4-([1,2,3]-thiadiazol-4-yl)-phenyl |
| 1152. | 3-fluoropropyl | 4-(1H-tetrazol-5-yl)-phenyl |

TABLE A-continued

| No. | R¹ | Ar |
|---|---|---|
| 1153. | 3-fluoropropyl | 4-(tetrazol-1-yl)-phenyl |
| 1154. | 3-fluoropropyl | 4-(2-methyl-2H-tetrazol-5-yl)-phenyl |
| 1155. | 3-fluoropropyl | 4-(1-methyl-1H-tetrazol-5-yl)-phenyl |
| 1156. | 3-fluoropropyl | 4-furazan-3-yl-phenyl |
| 1157. | 3-fluoropropyl | 4-(pyrid-2-yl)-phenyl |
| 1158. | 3-fluoropropyl | 4-(pyrid-3-yl)-phenyl |
| 1159. | 3-fluoropropyl | 4-(pyrid-4-yl)-phenyl |
| 1160. | 3-fluoropropyl | 4-(pyrimidin-2-yl)-phenyl |
| 1161. | 3-fluoropropyl | 4-(pyrimidin-4-yl)-phenyl |
| 1162. | 3-fluoropropyl | 4-(pyrimidin-5-yl)-phenyl |
| 1163. | 3-fluoropropyl | 5-isopropylthiophen-2-yl |
| 1164. | 3-fluoropropyl | 2-chlorothiophen-5-yl |
| 1165. | 3-fluoropropyl | 2,5-dichlorothiophen-4-yl |
| 1166. | 3-fluoropropyl | 2,3-dichlorothiophen-5-yl |
| 1167. | 3-fluoropropyl | 2-chloro-3-nitrothiophen-5-yl |
| 1168. | 3-fluoropropyl | 2-(phenylsulfonyl)-thiophen-5-yl |
| 1169. | 3-fluoropropyl | 2-(pyridin-2-yl)thiophen-5-yl |
| 1170. | 3-fluoropropyl | 2-(5-(trifluoromethyl)isoxazol-3-yl)-thiophen-5-yl |
| 1171. | 3-fluoropropyl | 2-(2-methylthiazol-4-yl)-thiophen-5-yl |
| 1172. | 3-fluoropropyl | 1-methyl-1H-imidazol-4-yl |
| 1173. | 3-fluoropropyl | 1,2-dimethyl-1H-imidazol-4-yl |
| 1174. | 3-fluoropropyl | 3,5-dimethylisoxazol-4-yl |
| 1175. | 3-fluoropropyl | thiazol-2-yl |
| 1176. | 3-fluoropropyl | 4-methylthiazol-2-yl |
| 1177. | 3-fluoropropyl | 4-isopropylthiazol-2-yl |
| 1178. | 3-fluoropropyl | 4-trifluoromethylthiazol-2-yl |
| 1179. | 3-fluoropropyl | 5-methylthiazol-2-yl |
| 1180. | 3-fluoropropyl | 5-isopropylthiazol-2-yl |
| 1181. | 3-fluoropropyl | 5-trifluoromethylthiazol-2-yl |
| 1182. | 3-fluoropropyl | 2,4-dimethylthiazol-5-yl |
| 1183. | 3-fluoropropyl | 2-acetamido-4-methylthiazol-5-yl |
| 1184. | 3-fluoropropyl | 4H-[1,2,4]triazol-3-yl |
| 1185. | 3-fluoropropyl | 5-methyl-4H-[1,2,4]triazol-3-yl |
| 1186. | 3-fluoropropyl | 4-methyl-4H-[1,2,4]triazol-3-yl |
| 1187. | 3-fluoropropyl | 5-isopropyl-4H-[1,2,4]triazol-3-yl |
| 1188. | 3-fluoropropyl | 5-trifluoromethyl-4H-[1,2,4]triazol-3-yl |
| 1189. | 3-fluoropropyl | 4,5-dimethyl-4H-[1,2,4]triazol-3-yl |
| 1190. | 3-fluoropropyl | 5-isopropyl-4-methyl-4H-[1,2,4]triazol-3-yl |
| 1191. | 3-fluoropropyl | 5-trifluoromethyl-4-methyl-4H-[1,2,4]triazol-3-yl |
| 1192. | 3-fluoropropyl | [1,3,4]thiadiazol-2-yl |
| 1193. | 3-fluoropropyl | 5-methyl-[1,3,4]thiadiazol-2-yl |
| 1194. | 3-fluoropropyl | 5-isopropyl-[1,3,4]thiadiazol-2-yl |
| 1195. | 3-fluoropropyl | 5-trifluoromethyl-[1,3,4]thiadiazol-2-yl |
| 1196. | 3-fluoropropyl | 3-bromo-2-chloropyrid-5-yl |
| 1197. | 3-fluoropropyl | 2-(4-morpholino)-pyrid-5-yl |
| 1198. | 3-fluoropropyl | 2-phenoxypyrid-5-yl |
| 1199. | 3-fluoropropyl | (2-isopropyl)-pyrimidin-5-yl |
| 1200. | 3-fluoropropyl | (5-isopropyl)-pyrimidin-2-yl |
| 1201. | 3-fluoropropyl | 8-quinolyl |
| 1202. | 3-fluoropropyl | 5-isoquinolyl |
| 1203. | 3-fluoropropyl | 2-(trifluoroacetyl)-1,2,3,4-tetrahydroisoquinolin-7-yl |
| 1204. | 3-fluoropropyl | 5-chloro-3-methylbenzothiophen-2-yl |
| 1205. | 3-fluoropropyl | 3,4-dihydro-4-methyl-2H-benzo[b][1,4]oxazinyl |
| 1206. | 3-fluoropropyl | benzothiazol-6-yl |
| 1207. | 3-fluoropropyl | benzo[2,1,3]oxadiazol-4-yl |
| 1208. | 3-fluoropropyl | 5-chlorobenzo[2,1,3]oxadiazol-4-yl |
| 1209. | 3-fluoropropyl | 7-chlorobenzo[2,1,3]oxadiazol-4-yl |
| 1210. | 3-fluoropropyl | benzo[2,1,3]thiadiazol-4-yl |
| 1211. | 2-fluoroethyl | 4-methylphenyl |
| 1212. | 2-fluoroethyl | 4-ethylphenyl |
| 1213. | 2-fluoroethyl | 4-propylphenyl |
| 1214. | 2-fluoroethyl | 4-isopropylphenyl |
| 1215. | 2-fluoroethyl | 4-sec-butylphenyl |
| 1216. | 2-fluoroethyl | 4-isobutylphenyl |
| 1217. | 2-fluoroethyl | 4-(1,1-dimethylpropyl)-phenyl |
| 1218. | 2-fluoroethyl | 4-vinylphenyl |
| 1219. | 2-fluoroethyl | 4-isopropenylphenyl |
| 1220. | 2-fluoroethyl | 4-fluorophenyl |
| 1221. | 2-fluoroethyl | 4-chlorophenyl |
| 1222. | 2-fluoroethyl | 4-bromophenyl |
| 1223. | 2-fluoroethyl | 4-(fluoromethyl)phenyl |
| 1224. | 2-fluoroethyl | 3-(fluoromethyl)phenyl |
| 1225. | 2-fluoroethyl | 2-(fluoromethyl)phenyl |
| 1226. | 2-fluoroethyl | 4-(difluoromethyl)phenyl |
| 1227. | 2-fluoroethyl | 3-(difluoromethyl)phenyl |
| 1228. | 2-fluoroethyl | 2-(difluoromethyl)phenyl |
| 1229. | 2-fluoroethyl | 4-(trifluoromethyl)phenyl |
| 1230. | 2-fluoroethyl | 3-(trifluoromethyl)phenyl |
| 1231. | 2-fluoroethyl | 2-(trifluoromethyl)phenyl |
| 1232. | 2-fluoroethyl | 4-(1-fluoroethyl)-phenyl |
| 1233. | 2-fluoroethyl | 4-((S)-1-fluoroethyl)-phenyl |
| 1234. | 2-fluoroethyl | 4-((R)-1-fluoroethyl)-phenyl |
| 1235. | 2-fluoroethyl | 4-(2-fluoroethyl)-phenyl |
| 1236. | 2-fluoroethyl | 4-(1,1-difluoroethyl)-phenyl |
| 1237. | 2-fluoroethyl | 4-(2,2-difluoroethyl)-phenyl |
| 1238. | 2-fluoroethyl | 4-(2,2,2-trifluoroethyl)-phenyl |
| 1239. | 2-fluoroethyl | 4-(3-fluoropropyl)-phenyl |
| 1240. | 2-fluoroethyl | 4-(2-fluoropropyl)-phenyl |
| 1241. | 2-fluoroethyl | 4-((S)-2-fluoropropyl)-phenyl |
| 1242. | 2-fluoroethyl | 4-((R)-2-fluoropropyl)-phenyl |
| 1243. | 2-fluoroethyl | 4-(3,3-difluoropropyl)-phenyl |
| 1244. | 2-fluoroethyl | 4-(3,3,3-trifluoropropyl)-phenyl |
| 1245. | 2-fluoroethyl | 4-(1-fluoro-1-methylethyl)-phenyl |
| 1246. | 2-fluoroethyl | 4-(2-fluoro-1-methylethyl)-phenyl |
| 1247. | 2-fluoroethyl | 4-((S)-2-fluoro-1-methylethyl)-phenyl |
| 1248. | 2-fluoroethyl | 4-((R)-2-fluoro-1-methylethyl)-phenyl |
| 1249. | 2-fluoroethyl | 4-(2,2-difluoro-1-methylethyl)-phenyl |
| 1250. | 2-fluoroethyl | 4-((S)-2,2-difluoro-1-methylethyl)-phenyl |
| 1251. | 2-fluoroethyl | 4-((R)-2,2-difluoro-1-methylethyl)-phenyl |
| 1252. | 2-fluoroethyl | 4-(2,2,2-trifluoro-1-methylethyl)-phenyl |
| 1253. | 2-fluoroethyl | 4-((S)-2,2,2-trifluoro-1-methylethyl)-phenyl |
| 1254. | 2-fluoroethyl | 4-((R)-2,2,2-trifluoro-1-methylethyl)-phenyl |
| 1255. | 2-fluoroethyl | 4-(2-fluoro-1-fluoromethylethyl)-phenyl |
| 1256. | 2-fluoroethyl | 4-(1-difluoromethyl-2,2-difluoroethyl)-phenyl |
| 1257. | 2-fluoroethyl | 4-(1,1-dimethyl-2-fluoroethyl)-phenyl |
| 1258. | 2-fluoroethyl | 4-methoxyphenyl |
| 1259. | 2-fluoroethyl | 4-ethoxyphenyl |
| 1260. | 2-fluoroethyl | 4-propoxyphenyl |
| 1261. | 2-fluoroethyl | 4-isopropoxyphenyl |
| 1262. | 2-fluoroethyl | 4-butoxyphenyl |
| 1263. | 2-fluoroethyl | 4-(fluoromethoxy)-phenyl |
| 1264. | 2-fluoroethyl | 4-(difluoromethoxy)-phenyl |
| 1265. | 2-fluoroethyl | 4-(trifluoromethoxy)-phenyl |
| 1266. | 2-fluoroethyl | 3-(trifluoromethoxy)-phenyl |
| 1267. | 2-fluoroethyl | 4-(2-fluoroethoxy)-phenyl |
| 1268. | 2-fluoroethyl | 4-(2,2-difluoroethoxy)-phenyl |
| 1269. | 2-fluoroethyl | 4-(2,2,2-trifluoroethoxy)-phenyl |
| 1270. | 2-fluoroethyl | 4-(1,1,2,2-tetrafluoroethoxy)-phenyl |
| 1271. | 2-fluoroethyl | 4-cyclopropylphenyl |
| 1272. | 2-fluoroethyl | 4-cyclobutylphenyl |
| 1273. | 2-fluoroethyl | 4-cyclopentylphenyl |
| 1274. | 2-fluoroethyl | 4-(2,2-difluorocyclopropyl)-phenyl |
| 1275. | 2-fluoroethyl | 3,4-difluorophenyl |
| 1276. | 2-fluoroethyl | 4-bromo-3-fluorophenyl |
| 1277. | 2-fluoroethyl | 4-bromo-2-fluorophenyl |
| 1278. | 2-fluoroethyl | 4-bromo-2,5-difluorophenyl |
| 1279. | 2-fluoroethyl | 2-fluoro-4-isopropylphenyl |
| 1280. | 2-fluoroethyl | 3-fluoro-4-isopropylphenyl |
| 1281. | 2-fluoroethyl | 4-(1-hydroxy-1-methylethyl)-phenyl |
| 1282. | 2-fluoroethyl | 4-(2-hydroxy-2-methylpropyl)-phenyl |
| 1283. | 2-fluoroethyl | 4-acetylphenyl |
| 1284. | 2-fluoroethyl | 4-carboxyphenyl |
| 1285. | 2-fluoroethyl | 4-cyanophenyl |
| 1286. | 2-fluoroethyl | 4-hydroxyphenyl |
| 1287. | 2-fluoroethyl | 4-(O-benzyl)-phenyl |
| 1288. | 2-fluoroethyl | 4-(2-methoxyethoxy)-phenyl |
| 1289. | 2-fluoroethyl | 4-(CH$_2$—N(CH$_3$)$_2$)-phenyl |
| 1290. | 2-fluoroethyl | 4-(NH—CO—NH$_2$)-phenyl |
| 1291. | 2-fluoroethyl | 4-(methylsulfanyl)-phenyl |
| 1292. | 2-fluoroethyl | 4-(fluoromethylsulfanyl)-phenyl |
| 1293. | 2-fluoroethyl | 4-(difluoromethylsulfanyl)-phenyl |
| 1294. | 2-fluoroethyl | 4-(trifluoromethylsulfanyl)-phenyl |
| 1295. | 2-fluoroethyl | 4-(methylsulfonyl)-phenyl |
| 1296. | 2-fluoroethyl | 4-(N-methoxy-N-methyl-amino)-phenyl |
| 1297. | 2-fluoroethyl | 4-(methoxyamino)-phenyl |
| 1298. | 2-fluoroethyl | 4-(ethoxyamino)-phenyl |
| 1299. | 2-fluoroethyl | 4-(N-methylaminooxy)-phenyl |
| 1300. | 2-fluoroethyl | 4-(N,N-dimethylaminooxy)-phenyl |
| 1301. | 2-fluoroethyl | 4-(azetidin-1-yl)-phenyl |
| 1302. | 2-fluoroethyl | 4-(2-methylazetidin-1-yl)-phenyl |
| 1303. | 2-fluoroethyl | 4-((S)-2-methylazetidin-1-yl)-phenyl |

TABLE A-continued

| No. | R¹ | Ar |
|---|---|---|
| 1304. | 2-fluoroethyl | 4-((R)-2-methylazetidin-1-yl)-phenyl |
| 1305. | 2-fluoroethyl | 4-(3-fluoroazetidin-1-yl)-phenyl |
| 1306. | 2-fluoroethyl | 4-(3-methoxyazetidin-1-yl)-phenyl |
| 1307. | 2-fluoroethyl | 4-(3-hydroxyazetidin-1-yl)-phenyl |
| 1308. | 2-fluoroethyl | 4-(pyrrolidin-1-yl)-phenyl |
| 1309. | 2-fluoroethyl | 4-(pyrrolidin-2-yl)-phenyl |
| 1310. | 2-fluoroethyl | 4-((S)-pyrrolidin-2-yl)-phenyl |
| 1311. | 2-fluoroethyl | 4-((R)-pyrrolidin-2-yl)-phenyl |
| 1312. | 2-fluoroethyl | 4-(pyrrolidin-3-yl)-phenyl |
| 1313. | 2-fluoroethyl | 4-((S)-pyrrolidin-3-yl)-phenyl |
| 1314. | 2-fluoroethyl | 4-((R)-pyrrolidin-3-yl)-phenyl |
| 1315. | 2-fluoroethyl | 4-(2-fluoropyrrolidin-1-yl)-phenyl |
| 1316. | 2-fluoroethyl | 4-((S)-2-fluoropyrrolidin-1-yl)-phenyl |
| 1317. | 2-fluoroethyl | 4-((R)-2-fluoropyrrolidin-1-yl)-phenyl |
| 1318. | 2-fluoroethyl | 4-(3-fluoropyrrolidin-1-yl)-phenyl |
| 1319. | 2-fluoroethyl | 4-((S)-3-fluoropyrrolidin-1-yl)-phenyl |
| 1320. | 2-fluoroethyl | 4-((R)-3-fluoropyrrolidin-1-yl)-phenyl |
| 1321. | 2-fluoroethyl | 4-(2,2-difluoropyrrolidin-1-yl)-phenyl |
| 1322. | 2-fluoroethyl | 4-(3,3-difluoropyrrolidin-1-yl)-phenyl |
| 1323. | 2-fluoroethyl | 4-(2-methylpyrrolidin-1-yl)-phenyl |
| 1324. | 2-fluoroethyl | 4-((S)-2-methylpyrrolidin-1-yl)-phenyl |
| 1325. | 2-fluoroethyl | 4-((R)-2-methylpyrrolidin-1-yl)-phenyl |
| 1326. | 2-fluoroethyl | 4-(3-methylpyrrolidin-1-yl)-phenyl |
| 1327. | 2-fluoroethyl | 4-((S)-3-methylpyrrolidin-1-yl)-phenyl |
| 1328. | 2-fluoroethyl | 4-((R)-3-methylpyrrolidin-1-yl)-phenyl |
| 1329. | 2-fluoroethyl | 4-(1-methylpyrrolidin-2-yl)-phenyl |
| 1330. | 2-fluoroethyl | 4-((S)-1-methylpyrrolidin-2-yl)-phenyl |
| 1331. | 2-fluoroethyl | 4-((R)-1-methylpyrrolidin-2-yl)-phenyl |
| 1332. | 2-fluoroethyl | 4-(1-methylpyrrolidin-3-yl)-phenyl |
| 1333. | 2-fluoroethyl | 4-((S)-1-methylpyrrolidin-3-yl)-phenyl |
| 1334. | 2-fluoroethyl | 4-((R)-1-methylpyrrolidin-3-yl)-phenyl |
| 1335. | 2-fluoroethyl | 4-(2,2-dimethylpyrrolidin-1-yl)-phenyl |
| 1336. | 2-fluoroethyl | 4-(3,3-dimethylpyrrolidin-1-yl)-phenyl |
| 1337. | 2-fluoroethyl | 4-(2-trifluoromethylpyrrolidin-1-yl)-phenyl |
| 1338. | 2-fluoroethyl | 4-((S)-2-trifluoromethylpyrrolidin-1-yl)-phenyl |
| 1339. | 2-fluoroethyl | 4-((R)-2-trifluoromethylpyrrolidin-1-yl)-phenyl |
| 1340. | 2-fluoroethyl | 4-(3-trifluoromethylpyrrolidin-1-yl)-phenyl |
| 1341. | 2-fluoroethyl | 4-((S)-3-trifluoromethylpyrrolidin-1-yl)-phenyl |
| 1342. | 2-fluoroethyl | 4-((R)-3-trifluoromethylpyrrolidin-1-yl)-phenyl |
| 1343. | 2-fluoroethyl | 4-(2-oxopyrrolidin-1-yl)-phenyl |
| 1344. | 2-fluoroethyl | 4-(2-oxo-oxazolidin-3-yl)-phenyl |
| 1345. | 2-fluoroethyl | 4-(piperidin-1-yl)-phenyl |
| 1346. | 2-fluoroethyl | 4-(2-methylpiperidin-1-yl)-phenyl |
| 1347. | 2-fluoroethyl | 4-((S)-2-methylpiperidin-1-yl)-phenyl |
| 1348. | 2-fluoroethyl | 4-((R)-2-methylpiperidin-1-yl)-phenyl |
| 1349. | 2-fluoroethyl | 4-(piperazin-1-yl)-phenyl |
| 1350. | 2-fluoroethyl | 4-(4-methylpiperazin-1-yl)-phenyl |
| 1351. | 2-fluoroethyl | 4-(morpholin-4-yl)-phenyl |
| 1352. | 2-fluoroethyl | 4-(thiomorpholin-4-yl)-phenyl |
| 1353. | 2-fluoroethyl | 4-(1-oxo-thiomorpholin-4-yl)-phenyl |
| 1354. | 2-fluoroethyl | 4-(1,1-dioxo-thiomorpholin-4-yl)-phenyl |
| 1355. | 2-fluoroethyl | 4-(pyrrol-1-yl)-phenyl |
| 1356. | 2-fluoroethyl | 4-(pyrrol-2-yl)-phenyl |
| 1357. | 2-fluoroethyl | 4-(pyrrol-3-yl)-phenyl |
| 1358. | 2-fluoroethyl | 4-(1-methylpyrrol-2-yl)-phenyl |
| 1359. | 2-fluoroethyl | 4-(1-methylpyrrol-3-yl)-phenyl |
| 1360. | 2-fluoroethyl | 4-(furan-2-yl)-phenyl |
| 1361. | 2-fluoroethyl | 4-(furan-3-yl)-phenyl |
| 1362. | 2-fluoroethyl | 4-(thiophen-2-yl)-phenyl |
| 1363. | 2-fluoroethyl | 4-(thiophen-3-yl)-phenyl |
| 1364. | 2-fluoroethyl | 4-(5-propylthien-2-yl)-phenyl |
| 1365. | 2-fluoroethyl | 4-(pyrazol-1-yl)-phenyl |
| 1366. | 2-fluoroethyl | 4-(pyrazol-3-yl)-phenyl |
| 1367. | 2-fluoroethyl | 4-(pyrazol-4-yl)-phenyl |
| 1368. | 2-fluoroethyl | 4-(1-methyl-1H-pyrazol-4-yl)-phenyl |
| 1369. | 2-fluoroethyl | 4-(1-ethyl-1H-pyrazol-4-yl)-phenyl |
| 1370. | 2-fluoroethyl | 4-(1-methyl-1H-pyrazol-5-yl)-phenyl |
| 1371. | 2-fluoroethyl | 4-(1H-imidazol-2-yl)-phenyl |
| 1372. | 2-fluoroethyl | 4-(imidazol-1-yl)-phenyl |
| 1373. | 2-fluoroethyl | 4-(1-methylimidazol-2-yl)-phenyl |
| 1374. | 2-fluoroethyl | 4-(oxazol-2-yl)-phenyl |
| 1375. | 2-fluoroethyl | 4-(oxazol-4-yl)-phenyl |
| 1376. | 2-fluoroethyl | 4-(oxazol-5-yl)-phenyl |
| 1377. | 2-fluoroethyl | 4-(isoxazol-3-yl)-phenyl |
| 1378. | 2-fluoroethyl | 4-(isoxazol-4-yl)-phenyl |
| 1379. | 2-fluoroethyl | 4-(isoxazol-5-yl)-phenyl |
| 1380. | 2-fluoroethyl | 4-([1,2,3]-triazol-1-yl)-phenyl |
| 1381. | 2-fluoroethyl | 4-([1,2,4]-triazol-1-yl)-phenyl |
| 1382. | 2-fluoroethyl | 4-([1,2,3]-triazol-2-yl)-phenyl |
| 1383. | 2-fluoroethyl | 4-(4H-[1,2,4]-triazol-3-yl)-phenyl |
| 1384. | 2-fluoroethyl | 4-([1,2,4]-triazol-4-yl)-phenyl |
| 1385. | 2-fluoroethyl | 4-(2H-[1,2,3]-triazol-4-yl)-phenyl |
| 1386. | 2-fluoroethyl | 4-(4-methyl-4H-[1,2,4]-triazol-3-yl)-phenyl |
| 1387. | 2-fluoroethyl | 4-(2-methyl-2H-[1,2,3]-triazol-4-yl)-phenyl |
| 1388. | 2-fluoroethyl | 4-([1,3,4]-oxadiazol-2-yl)-phenyl |
| 1389. | 2-fluoroethyl | 4-([1,2,4]-oxadiazol-3-yl)-phenyl |
| 1390. | 2-fluoroethyl | 4-([1,2,4]-oxadiazol-5-yl)-phenyl |
| 1391. | 2-fluoroethyl | 4-([1,2,3]-oxadiazol-4-yl)-phenyl |
| 1392. | 2-fluoroethyl | 4-([1,2,3]-oxadiazol-5-yl)-phenyl |
| 1393. | 2-fluoroethyl | 4-([1,2,3]-thiadiazol-4-yl)-phenyl |
| 1394. | 2-fluoroethyl | 4-(1H-tetrazol-5-yl)-phenyl |
| 1395. | 2-fluoroethyl | 4-(tetrazol-1-yl)-phenyl |
| 1396. | 2-fluoroethyl | 4-(2-methyl-2H-tetrazol-5-yl)-phenyl |
| 1397. | 2-fluoroethyl | 4-(1-methyl-1H-tetrazol-5-yl)-phenyl |
| 1398. | 2-fluoroethyl | 4-furazan-3-yl-phenyl |
| 1399. | 2-fluoroethyl | 4-(pyrid-2-yl)-phenyl |
| 1400. | 2-fluoroethyl | 4-(pyrid-3-yl)-phenyl |
| 1401. | 2-fluoroethyl | 4-(pyrid-4-yl)-phenyl |
| 1402. | 2-fluoroethyl | 4-(pyrimidin-2-yl)-phenyl |
| 1403. | 2-fluoroethyl | 4-(pyrimidin-4-yl)-phenyl |
| 1404. | 2-fluoroethyl | 4-(pyrimidin-5-yl)-phenyl |
| 1405. | 2-fluoroethyl | 5-isopropylthiophen-2-yl |
| 1406. | 2-fluoroethyl | 2-chlorothiophen-5-yl |
| 1407. | 2-fluoroethyl | 2,5-dichlorothiophen-4-yl |
| 1408. | 2-fluoroethyl | 2,3-dichlorothiophen-5-yl |
| 1409. | 2-fluoroethyl | 2-chloro-3-nitrothiophen-5-yl |
| 1410. | 2-fluoroethyl | 2-(phenylsulfonyl)-thiophen-5-yl |
| 1411. | 2-fluoroethyl | 2-(pyridin-2-yl)thiophen-5-yl |
| 1412. | 2-fluoroethyl | 2-(5-(trifluoromethyl)isoxazol-3-yl)-thiophen-5-yl |
| 1413. | 2-fluoroethyl | 2-(2-methylthiazol-4-yl)-thiophen-5-yl |
| 1414. | 2-fluoroethyl | 1-methyl-1H-imidazol-4-yl |
| 1415. | 2-fluoroethyl | 1,2-dimethyl-1H-imidazol-4-yl |
| 1416. | 2-fluoroethyl | 3,5-dimethylisoxazol-4-yl |
| 1417. | 2-fluoroethyl | thiazol-2-yl |
| 1418. | 2-fluoroethyl | 4-methylthiazol-2-yl |
| 1419. | 2-fluoroethyl | 4-isopropylthiazol-2-yl |
| 1420. | 2-fluoroethyl | 4-trifluoromethylthiazol-2-yl |
| 1421. | 2-fluoroethyl | 5-methylthiazol-2-yl |
| 1422. | 2-fluoroethyl | 5-isopropylthiazol-2-yl |
| 1423. | 2-fluoroethyl | 5-trifluoromethylthiazol-2-yl |
| 1424. | 2-fluoroethyl | 2,4-dimethylthiazol-5-yl |
| 1425. | 2-fluoroethyl | 2-acetamido-4-methylthiazol-5-yl |
| 1426. | 2-fluoroethyl | 4H-[1,2,4]triazol-3-yl |
| 1427. | 2-fluoroethyl | 5-methyl-4H-[1,2,4]triazol-3-yl |
| 1428. | 2-fluoroethyl | 4-methyl-4H-[1,2,4]triazol-3-yl |
| 1429. | 2-fluoroethyl | 5-isopropyl-4H-[1,2,4]triazol-3-yl |
| 1430. | 2-fluoroethyl | 5-trifluoromethyl-4H-[1,2,4]triazol-3-yl |
| 1431. | 2-fluoroethyl | 4,5-dimethyl-4H-[1,2,4]triazol-3-yl |
| 1432. | 2-fluoroethyl | 5-isopropyl-4-methyl-4H-[1,2,4]triazol-3-yl |
| 1433. | 2-fluoroethyl | 5-trifluoromethyl-4-methyl-4H-[1,2,4]triazol-3-yl |
| 1434. | 2-fluoroethyl | [1,3,4]thiadiazol-2-yl |
| 1435. | 2-fluoroethyl | 5-methyl-[1,3,4]thiadiazol-2-yl |
| 1436. | 2-fluoroethyl | 5-isopropyl-[1,3,4]thiadiazol-2-yl |
| 1437. | 2-fluoroethyl | 5-trifluoromethyl-[1,3,4]thiadiazol-2-yl |
| 1438. | 2-fluoroethyl | 3-bromo-2-chloropyrid-5-yl |
| 1439. | 2-fluoroethyl | 2-(4-morpholino)-pyrid-5-yl |
| 1440. | 2-fluoroethyl | 2-phenoxypyrid-5-yl |
| 1441. | 2-fluoroethyl | (2-isopropyl)-pyrimidin-5-yl |
| 1442. | 2-fluoroethyl | (5-isopropyl)-pyrimidin-2-yl |
| 1443. | 2-fluoroethyl | 8-quinolyl |
| 1444. | 2-fluoroethyl | 5-isoquinolyl |
| 1445. | 2-fluoroethyl | 2-(trifluoroacetyl)-1,2,3,4-tetrahydroisoquinolin-7-yl |
| 1446. | 2-fluoroethyl | 5-chloro-3-methylbenzothiophen-2-yl |
| 1447. | 2-fluoroethyl | 3,4-dihydro-4-methyl-2H-benzo[b][1,4]oxazinyl |
| 1448. | 2-fluoroethyl | benzothiazol-6-yl |
| 1449. | 2-fluoroethyl | benzo[2,1,3]oxadiazol-4-yl |
| 1450. | 2-fluoroethyl | 5-chlorobenzo[2,1,3]oxadiazol-4-yl |
| 1451. | 2-fluoroethyl | 7-chlorobenzo[2,1,3]oxadiazol-4-yl |

TABLE A-continued

| No. | R¹ | Ar |
|---|---|---|
| 1452. | 2-fluoroethyl | benzo[2,1,3]thiadiazol-4-yl |
| 1453. | cyclopropylmethyl | 4-methylphenyl |
| 1454. | cyclopropylmethyl | 4-ethylphenyl |
| 1455. | cyclopropylmethyl | 4-propylphenyl |
| 1456. | cyclopropylmethyl | 4-isopropylphenyl |
| 1457. | cyclopropylmethyl | 4-sec-butylphenyl |
| 1458. | cyclopropylmethyl | 4-isobutylphenyl |
| 1459. | cyclopropylmethyl | 4-(1,1-dimethylpropyl)-phenyl |
| 1460. | cyclopropylmethyl | 4-vinylphenyl |
| 1461. | cyclopropylmethyl | 4-isopropenylphenyl |
| 1462. | cyclopropylmethyl | 4-fluorophenyl |
| 1463. | cyclopropylmethyl | 4-chlorophenyl |
| 1464. | cyclopropylmethyl | 4-bromophenyl |
| 1465. | cyclopropylmethyl | 4-(fluoromethyl)phenyl |
| 1466. | cyclopropylmethyl | 3-(fluoromethyl)phenyl |
| 1467. | cyclopropylmethyl | 2-(fluoromethyl)phenyl |
| 1468. | cyclopropylmethyl | 4-(difluoromethyl)phenyl |
| 1469. | cyclopropylmethyl | 3-(difluoromethyl)phenyl |
| 1470. | cyclopropylmethyl | 2-(difluoromethyl)phenyl |
| 1471. | cyclopropylmethyl | 4-(trifluoromethyl)phenyl |
| 1472. | cyclopropylmethyl | 3-(trifluoromethyl)phenyl |
| 1473. | cyclopropylmethyl | 2-(trifluoromethyl)phenyl |
| 1474. | cyclopropylmethyl | 4-(1-fluoroethyl)-phenyl |
| 1475. | cyclopropylmethyl | 4-((S)-1-fluoroethyl)-phenyl |
| 1476. | cyclopropylmethyl | 4-((R)-1-fluoroethyl)-phenyl |
| 1477. | cyclopropylmethyl | 4-(2-fluoroethyl)-phenyl |
| 1478. | cyclopropylmethyl | 4-(1,1-difluoroethyl)-phenyl |
| 1479. | cyclopropylmethyl | 4-(2,2-difluoroethyl)-phenyl |
| 1480. | cyclopropylmethyl | 4-(2,2,2-trifluoroethyl)-phenyl |
| 1481. | cyclopropylmethyl | 4-(3-fluoropropyl)-phenyl |
| 1482. | cyclopropylmethyl | 4-(2-fluoropropyl)-phenyl |
| 1483. | cyclopropylmethyl | 4-((S)-2-fluoropropyl)-phenyl |
| 1484. | cyclopropylmethyl | 4-((R)-2-fluoropropyl)-phenyl |
| 1485. | cyclopropylmethyl | 4-(3,3-difluoropropyl)-phenyl |
| 1486. | cyclopropylmethyl | 4-(3,3,3-trifluoropropyl)-phenyl |
| 1487. | cyclopropylmethyl | 4-(1-fluoro-1-methylethyl)-phenyl |
| 1488. | cyclopropylmethyl | 4-(2-fluoro-1-methylethyl)-phenyl |
| 1489. | cyclopropylmethyl | 4-((S)-2-fluoro-1-methylethyl)-phenyl |
| 1490. | cyclopropylmethyl | 4-((R)-2-fluoro-1-methylethyl)-phenyl |
| 1491. | cyclopropylmethyl | 4-(2,2-difluoro-1-methylethyl)-phenyl |
| 1492. | cyclopropylmethyl | 4-((S)-2,2-difluoro-1-methylethyl)-phenyl |
| 1493. | cyclopropylmethyl | 4-((R)-2,2-difluoro-1-methylethyl)-phenyl |
| 1494. | cyclopropylmethyl | 4-(2,2,2-trifluoro-1-methylethyl)-phenyl |
| 1495. | cyclopropylmethyl | 4-((S)-2,2,2-trifluoro-1-methylethyl)-phenyl |
| 1496. | cyclopropylmethyl | 4-((R)-2,2,2-trifluoro-1-methylethyl)-phenyl |
| 1497. | cyclopropylmethyl | 4-(2-fluoro-1-fluoromethylethyl)-phenyl |
| 1498. | cyclopropylmethyl | 4-(1-difluoromethyl-2,2-difluoroethyl)-phenyl |
| 1499. | cyclopropylmethyl | 4-(1,1-dimethyl-2-fluoroethyl)-phenyl |
| 1500. | cyclopropylmethyl | 4-methoxyphenyl |
| 1501. | cyclopropylmethyl | 4-ethoxyphenyl |
| 1502. | cyclopropylmethyl | 4-propoxyphenyl |
| 1503. | cyclopropylmethyl | 4-isopropoxyphenyl |
| 1504. | cyclopropylmethyl | 4-butoxyphenyl |
| 1505. | cyclopropylmethyl | 4-(fluoromethoxy)-phenyl |
| 1506. | cyclopropylmethyl | 4-(difluoromethoxy)-phenyl |
| 1507. | cyclopropylmethyl | 4-(trifluoromethoxy)-phenyl |
| 1508. | cyclopropylmethyl | 3-(trifluoromethoxy)-phenyl |
| 1509. | cyclopropylmethyl | 4-(2-fluoroethoxy)-phenyl |
| 1510. | cyclopropylmethyl | 4-(2,2-difluoroethoxy)-phenyl |
| 1511. | cyclopropylmethyl | 4-(2,2,2-trifluoroethoxy)-phenyl |
| 1512. | cyclopropylmethyl | 4-(1,1,2,2-tetrafluoroethoxy)-phenyl |
| 1513. | cyclopropylmethyl | 4-cyclopropylphenyl |
| 1514. | cyclopropylmethyl | 4-cyclobutylphenyl |
| 1515. | cyclopropylmethyl | 4-cyclopentylphenyl |
| 1516. | cyclopropylmethyl | 4-(2,2-difluorocyclopropyl)-phenyl |
| 1517. | cyclopropylmethyl | 3,4-difluorophenyl |
| 1518. | cyclopropylmethyl | 4-bromo-3-fluorophenyl |
| 1519. | cyclopropylmethyl | 4-bromo-2-fluorophenyl |
| 1520. | cyclopropylmethyl | 4-bromo-2,5-difluorophenyl |
| 1521. | cyclopropylmethyl | 2-fluoro-4-isopropylphenyl |
| 1522. | cyclopropylmethyl | 3-fluoro-4-isopropylphenyl |
| 1523. | cyclopropylmethyl | 4-(1-hydroxy-1-methylethyl)-phenyl |
| 1524. | cyclopropylmethyl | 4-(2-hydroxy-2-methylpropyl)-phenyl |
| 1525. | cyclopropylmethyl | 4-acetylphenyl |
| 1526. | cyclopropylmethyl | 4-carboxyphenyl |
| 1527. | cyclopropylmethyl | 4-cyanophenyl |
| 1528. | cyclopropylmethyl | 4-hydroxyphenyl |
| 1529. | cyclopropylmethyl | 4-(O-benzyl)-phenyl |
| 1530. | cyclopropylmethyl | 4-(2-methoxyethoxy)-phenyl |
| 1531. | cyclopropylmethyl | 4-(CH$_2$—N(CH$_3$)$_2$)-phenyl |
| 1532. | cyclopropylmethyl | 4-(NH—CO—NH$_2$)-phenyl |
| 1533. | cyclopropylmethyl | 4-(methylsulfanyl)-phenyl |
| 1534. | cyclopropylmethyl | 4-(fluoromethylsulfanyl)-phenyl |
| 1535. | cyclopropylmethyl | 4-(difluoromethylsulfanyl)-phenyl |
| 1536. | cyclopropylmethyl | 4-(trifluoromethylsulfanyl)-phenyl |
| 1537. | cyclopropylmethyl | 4-(methylsulfonyl)-phenyl |
| 1538. | cyclopropylmethyl | 4-(N-methoxy-N-methyl-amino)-phenyl |
| 1539. | cyclopropylmethyl | 4-(methoxyamino)-phenyl |
| 1540. | cyclopropylmethyl | 4-(ethoxyamino)-phenyl |
| 1541. | cyclopropylmethyl | 4-(N-methylaminooxy)-phenyl |
| 1542. | cyclopropylmethyl | 4-(N,N-dimethylaminooxy)-phenyl |
| 1543. | cyclopropylmethyl | 4-(azetidin-1-yl)-phenyl |
| 1544. | cyclopropylmethyl | 4-(2-methylazetidin-1-yl)-phenyl |
| 1545. | cyclopropylmethyl | 4-((S)-2-methylazetidin-1-yl)-phenyl |
| 1546. | cyclopropylmethyl | 4-((R)-2-methylazetidin-1-yl)-phenyl |
| 1547. | cyclopropylmethyl | 4-(3-fluoroazetidin-1-yl)-phenyl |
| 1548. | cyclopropylmethyl | 4-(3-methoxyazetidin-1-yl)-phenyl |
| 1549. | cyclopropylmethyl | 4-(3-hydroxyazetidin-1-yl)-phenyl |
| 1550. | cyclopropylmethyl | 4-(pyrrolidin-1-yl)-phenyl |
| 1551. | cyclopropylmethyl | 4-(pyrrolidin-2-yl)-phenyl |
| 1552. | cyclopropylmethyl | 4-((S)-pyrrolidin-2-yl)-phenyl |
| 1553. | cyclopropylmethyl | 4-((R)-pyrrolidin-2-yl)-phenyl |
| 1554. | cyclopropylmethyl | 4-(pyrrolidin-3-yl)-phenyl |
| 1555. | cyclopropylmethyl | 4-((S)-pyrrolidin-3-yl)-phenyl |
| 1556. | cyclopropylmethyl | 4-((R)-pyrrolidin-3-yl)-phenyl |
| 1557. | cyclopropylmethyl | 4-(2-fluoropyrrolidin-1-yl)-phenyl |
| 1558. | cyclopropylmethyl | 4-(S)-2-fluoropyrrolidin-1-yl)-phenyl |
| 1559. | cyclopropylmethyl | 4-((R)-2-fluoropyrrolidin-1-yl)-phenyl |
| 1560. | cyclopropylmethyl | 4-(3-fluoropyrrolidin-1-yl)-phenyl |
| 1561. | cyclopropylmethyl | 4-((S)-3-fluoropyrrolidin-1-yl)-phenyl |
| 1562. | cyclopropylmethyl | 4-((R)-3-fluoropyrrolidin-1-yl)-phenyl |
| 1563. | cyclopropylmethyl | 4-(2,2-difluoropyrrolidin-1-yl)-phenyl |
| 1564. | cyclopropylmethyl | 4-(3,3-difluoropyrrolidin-1-yl)-phenyl |
| 1565. | cyclopropylmethyl | 4-(2-methylpyrrolidin-1-yl)-phenyl |
| 1566. | cyclopropylmethyl | 4-((S)-2-methylpyrrolidin-1-yl)-phenyl |
| 1567. | cyclopropylmethyl | 4-((R)-2-methylpyrrolidin-1-yl)-phenyl |
| 1568. | cyclopropylmethyl | 4-(3-methylpyrrolidin-1-yl)-phenyl |
| 1569. | cyclopropylmethyl | 4-((S)-3-methylpyrrolidin-1-yl)-phenyl |
| 1570. | cyclopropylmethyl | 4-((R)-3-methylpyrrolidin-1-yl)-phenyl |
| 1571. | cyclopropylmethyl | 4-(1-methylpyrrolidin-2-yl)-phenyl |
| 1572. | cyclopropylmethyl | 4-((S)-1-methylpyrrolidin-2-yl)-phenyl |
| 1573. | cyclopropylmethyl | 4-((R)-1-methylpyrrolidin-2-yl)-phenyl |
| 1574. | cyclopropylmethyl | 4-(1-methylpyrrolidin-3-yl)-phenyl |
| 1575. | cyclopropylmethyl | 4-((S)-1-methylpyrrolidin-3-yl)-phenyl |
| 1576. | cyclopropylmethyl | 4-((R)-1-methylpyrrolidin-3-yl)-phenyl |
| 1577. | cyclopropylmethyl | 4-(2,2-dimethylpyrrolidin-1-yl)-phenyl |
| 1578. | cyclopropylmethyl | 4-(3,3-dimethylpyrrolidin-1-yl)-phenyl |
| 1579. | cyclopropylmethyl | 4-(2-trifluoromethylpyrrolidin-1-yl)-phenyl |
| 1580. | cyclopropylmethyl | 4-((S)-2-trifluoromethylpyrrolidin-1-yl)-phenyl |
| 1581. | cyclopropylmethyl | 4-((R)-2-trifluoromethylpyrrolidin-1-yl)-phenyl |
| 1582. | cyclopropylmethyl | 4-(3-trifluoromethylpyrrolidin-1-yl)-phenyl |
| 1583. | cyclopropylmethyl | 4-((S)-3-trifluoromethylpyrrolidin-1-yl)-phenyl |
| 1584. | cyclopropylmethyl | 4-((R)-3-trifluoromethylpyrrolidin-1-yl)-phenyl |
| 1585. | cyclopropylmethyl | 4-(2-oxopyrrolidin-1-yl)-phenyl |
| 1586. | cyclopropylmethyl | 4-(2-oxo-oxazolidin-3-yl)-phenyl |
| 1587. | cyclopropylmethyl | 4-(piperidin-1-yl)-phenyl |
| 1588. | cyclopropylmethyl | 4-(2-methylpiperidin-1-yl)-phenyl |
| 1589. | cyclopropylmethyl | 4-((S)-2-methylpiperidin-1-yl)-phenyl |
| 1590. | cyclopropylmethyl | 4-((R)-2-methylpiperidin-1-yl)-phenyl |
| 1591. | cyclopropylmethyl | 4-(piperazin-1-yl)-phenyl |
| 1592. | cyclopropylmethyl | 4-(4-methylpiperazin-1-yl)-phenyl |
| 1593. | cyclopropylmethyl | 4-(morpholin-4-yl)-phenyl |
| 1594. | cyclopropylmethyl | 4-(thiomorpholin-4-yl)-phenyl |
| 1595. | cyclopropylmethyl | 4-(1-oxo-thiomorpholin-4-yl)-phenyl |
| 1596. | cyclopropylmethyl | 4-(1,1-dioxo-thiomorpholin-4-yl)-phenyl |
| 1597. | cyclopropylmethyl | 4-(pyrrol-1-yl)-phenyl |
| 1598. | cyclopropylmethyl | 4-(pyrrol-2-yl)-phenyl |
| 1599. | cyclopropylmethyl | 4-(pyrrol-3-yl)-phenyl |
| 1600. | cyclopropylmethyl | 4-(1-methylpyrrol-2-yl)-phenyl |
| 1601. | cyclopropylmethyl | 4-(1-methylpyrrol-3-yl)-phenyl |
| 1602. | cyclopropylmethyl | 4-(furan-2-yl)-phenyl |

TABLE A-continued

| No. | R¹ | Ar |
|---|---|---|
| 1603. | cyclopropylmethyl | 4-(furan-3-yl)-phenyl |
| 1604. | cyclopropylmethyl | 4-(thiophen-2-yl)-phenyl |
| 1605. | cyclopropylmethyl | 4-(thiophen-3-yl)-phenyl |
| 1606. | cyclopropylmethyl | 4-(5-propylthien-2-yl)-phenyl |
| 1607. | cyclopropylmethyl | 4-(pyrazol-1-yl)-phenyl |
| 1608. | cyclopropylmethyl | 4-(pyrazol-3-yl)-phenyl |
| 1609. | cyclopropylmethyl | 4-(pyrazol-4-yl)-phenyl |
| 1610. | cyclopropylmethyl | 4-(1-methyl-1H-pyrazol-4-yl)-phenyl |
| 1611. | cyclopropylmethyl | 4-(1-ethyl-1H-pyrazol-4-yl)-phenyl |
| 1612. | cyclopropylmethyl | 4-(1-methyl-1H-pyrazol-5-yl)-phenyl |
| 1613. | cyclopropylmethyl | 4-(1H-imidazol-2-yl)-phenyl |
| 1614. | cyclopropylmethyl | 4-(imidazol-1-yl)-phenyl |
| 1615. | cyclopropylmethyl | 4-(1-methylimidazol-2-yl)-phenyl |
| 1616. | cyclopropylmethyl | 4-(oxazol-2-yl)-phenyl |
| 1617. | cyclopropylmethyl | 4-(oxazol-4-yl)-phenyl |
| 1618. | cyclopropylmethyl | 4-(oxazol-5-yl)-phenyl |
| 1619. | cyclopropylmethyl | 4-(isoxazol-3-yl)-phenyl |
| 1620. | cyclopropylmethyl | 4-(isoxazol-4-yl)-phenyl |
| 1621. | cyclopropylmethyl | 4-(isoxazol-5-yl)-phenyl |
| 1622. | cyclopropylmethyl | 4-([1,2,3]-triazol-1-yl)-phenyl |
| 1623. | cyclopropylmethyl | 4-([1,2,4]-triazol-1-yl)-phenyl |
| 1624. | cyclopropylmethyl | 4-([1,2,3]-triazol-2-yl)-phenyl |
| 1625. | cyclopropylmethyl | 4-(4H-[1,2,4]-triazol-3-yl)-phenyl |
| 1626. | cyclopropylmethyl | 4-([1,2,4]-triazol-4-yl)-phenyl |
| 1627. | cyclopropylmethyl | 4-(2H-[1,2,3]-triazol-4-yl)-phenyl |
| 1628. | cyclopropylmethyl | 4-(4-methyl-4H-[1,2,4]-triazol-3-yl)-phenyl |
| 1629. | cyclopropylmethyl | 4-(2-methyl-2H-[1,2,3]-triazol-4-yl)-phenyl |
| 1630. | cyclopropylmethyl | 4-([1,3,4]-oxadiazol-2-yl)-phenyl |
| 1631. | cyclopropylmethyl | 4-([1,2,4]-oxadiazol-3-yl)-phenyl |
| 1632. | cyclopropylmethyl | 4-([1,2,4]-oxadiazol-5-yl)-phenyl |
| 1633. | cyclopropylmethyl | 4-([1,2,3]-oxadiazol-4-yl)-phenyl |
| 1634. | cyclopropylmethyl | 4-([1,2,3]-oxadiazol-5-yl)-phenyl |
| 1635. | cyclopropylmethyl | 4-([1,2,3]-thiadiazol-4-yl)-phenyl |
| 1636. | cyclopropylmethyl | 4-(1H-tetrazol-5-yl)-phenyl |
| 1637. | cyclopropylmethyl | 4-(tetrazol-1-yl)-phenyl |
| 1638. | cyclopropylmethyl | 4-(2-methyl-2H-tetrazol-5-yl)-phenyl |
| 1639. | cyclopropylmethyl | 4-(1-methyl-1H-tetrazol-5-yl)-phenyl |
| 1640. | cyclopropylmethyl | 4-furazan-3-yl-phenyl |
| 1641. | cyclopropylmethyl | 4-(pyrid-2-yl)-phenyl |
| 1642. | cyclopropylmethyl | 4-(pyrid-3-yl)-phenyl |
| 1643. | cyclopropylmethyl | 4-(pyrid-4-yl)-phenyl |
| 1644. | cyclopropylmethyl | 4-(pyrimidin-2-yl)-phenyl |
| 1645. | cyclopropylmethyl | 4-(pyrimidin-4-yl)-phenyl |
| 1646. | cyclopropylmethyl | 4-(pyrimidin-5-yl)-phenyl |
| 1647. | cyclopropylmethyl | 5-isopropylthiophen-2-yl |
| 1648. | cyclopropylmethyl | 2-chlorothiophen-5-yl |
| 1649. | cyclopropylmethyl | 2,5-dichlorothiophen-4-yl |
| 1650. | cyclopropylmethyl | 2,3-dichlorothiophen-5-yl |
| 1651. | cyclopropylmethyl | 2-chloro-3-nitrothiophen-5-yl |
| 1652. | cyclopropylmethyl | 2-(phenylsulfonyl)-thiophen-5-yl |
| 1653. | cyclopropylmethyl | 2-(pyridin-2-yl)thiophen-5-yl |
| 1654. | cyclopropylmethyl | 2-(5-(trifluoromethyl)isoxazol-3-yl)-thiophen-5-yl |
| 1655. | cyclopropylmethyl | 2-(2-methylthiazol-4-yl)-thiophen-5-yl |
| 1656. | cyclopropylmethyl | 1-methyl-1H-imidazol-4-yl |
| 1657. | cyclopropylmethyl | 1,2-dimethyl-1H-imidazol-4-yl |
| 1658. | cyclopropylmethyl | 3,5-dimethylisoxazol-4-yl |
| 1659. | cyclopropylmethyl | thiazol-2-yl |
| 1660. | cyclopropylmethyl | 4-methylthiazol-2-yl |
| 1661. | cyclopropylmethyl | 4-isopropylthiazol-2-yl |
| 1662. | cyclopropylmethyl | 4-trifluoromethylthiazol-2-yl |
| 1663. | cyclopropylmethyl | 5-methylthiazol-2-yl |
| 1664. | cyclopropylmethyl | 5-isopropylthiazol-2-yl |
| 1665. | cyclopropylmethyl | 5-trifluoromethylthiazol-2-yl |
| 1666. | cyclopropylmethyl | 2,4-dimethylthiazol-5-yl |
| 1667. | cyclopropylmethyl | 2-acetamido-4-methylthiazol-5-yl |
| 1668. | cyclopropylmethyl | 4H-[1,2,4]triazol-3-yl |
| 1669. | cyclopropylmethyl | 5-methyl-4H-[1,2,4]triazol-3-yl |
| 1670. | cyclopropylmethyl | 4-methyl-4H-[1,2,4]triazol-3-yl |
| 1671. | cyclopropylmethyl | 5-isopropyl-4H-[1,2,4]triazol-3-yl |
| 1672. | cyclopropylmethyl | 5-trifluoromethyl-4H-[1,2,4]triazol-3-yl |
| 1673. | cyclopropylmethyl | 4,5-dimethyl-4H-[1,2,4]triazol-3-yl |
| 1674. | cyclopropylmethyl | 5-isopropyl-4-methyl-4H-[1,2,4]triazol-3-yl |
| 1675. | cyclopropylmethyl | 5-trifluoromethyl-4-methyl-4H-[1,2,4]triazol-3-yl |
| 1676. | cyclopropylmethyl | [1,3,4]thiadiazol-2-yl |
| 1677. | cyclopropylmethyl | 5-methyl-[1,3,4]thiadiazol-2-yl |
| 1678. | cyclopropylmethyl | 5-isopropyl-[1,3,4]thiadiazol-2-yl |
| 1679. | cyclopropylmethyl | 5-trifluoromethyl-[1,3,4]thiadiazol-2-yl |
| 1680. | cyclopropylmethyl | 3-bromo-2-chloropyrid-5-yl |
| 1681. | cyclopropylmethyl | 2-(4-morpholino)-pyrid-5-yl |
| 1682. | cyclopropylmethyl | 2-phenoxypyrid-5-yl |
| 1683. | cyclopropylmethyl | (2-isopropyl)-pyrimidin-5-yl |
| 1684. | cyclopropylmethyl | (5-isopropyl)-pyrimidin-2-yl |
| 1685. | cyclopropylmethyl | 8-quinolyl |
| 1686. | cyclopropylmethyl | 5-isoquinolyl |
| 1687. | cyclopropylmethyl | 2-(trifluoroacetyl)-1,2,3,4-tetrahydroisoquinolin-7-yl |
| 1688. | cyclopropylmethyl | 5-chloro-3-methylbenzothiophen-2-yl |
| 1689. | cyclopropylmethyl | 3,4-dihydro-4-methyl-2H-benzo[b][1,4]oxazinyl |
| 1690. | cyclopropylmethyl | benzothiazol-6-yl |
| 1691. | cyclopropylmethyl | benzo[2,1,3]oxadiazol-4-yl |
| 1692. | cyclopropylmethyl | 5-chlorobenzo[2,1,3]oxadiazol-4-yl |
| 1693. | cyclopropylmethyl | 7-chlorobenzo[2,1,3]oxadiazol-4-yl |
| 1694. | cyclopropylmethyl | benzo[2,1,3]thiadiazol-4-yl |
| 1695. | allyl | 4-methylphenyl |
| 1696. | allyl | 4-ethylphenyl |
| 1697. | allyl | 4-propylphenyl |
| 1698. | allyl | 4-isopropylphenyl |
| 1699. | allyl | 4-sec-butylphenyl |
| 1700. | allyl | 4-isobutylphenyl |
| 1701. | allyl | 4-(1,1-dimethylpropyl)-phenyl |
| 1702. | allyl | 4-vinylphenyl |
| 1703. | allyl | 4-isopropenylphenyl |
| 1704. | allyl | 4-fluorophenyl |
| 1705. | allyl | 4-chlorophenyl |
| 1706. | allyl | 4-bromophenyl |
| 1707. | allyl | 4-(fluoromethyl)phenyl |
| 1708. | allyl | 3-(fluoromethyl)phenyl |
| 1709. | allyl | 2-(fluoromethyl)phenyl |
| 1710. | allyl | 4-(difluoromethyl)phenyl |
| 1711. | allyl | 3-(difluoromethyl)phenyl |
| 1712. | allyl | 2-(difluoromethyl)phenyl |
| 1713. | allyl | 4-(trifluoromethyl)phenyl |
| 1714. | allyl | 3-(trifluoromethyl)phenyl |
| 1715. | allyl | 2-(trifluoromethyl)phenyl |
| 1716. | allyl | 4-(1-fluoroethyl)-phenyl |
| 1717. | allyl | 4-((S)-1-fluoroethyl)-phenyl |
| 1718. | allyl | 4-((R)-1-fluoroethyl)-phenyl |
| 1719. | allyl | 4-(2-fluoroethyl)-phenyl |
| 1720. | allyl | 4-(1,1-difluoroethyl)-phenyl |
| 1721. | allyl | 4-(2,2-difluoroethyl)-phenyl |
| 1722. | allyl | 4-(2,2,2-trifluoroethyl)-phenyl |
| 1723. | allyl | 4-(3-fluoropropyl)-phenyl |
| 1724. | allyl | 4-(2-fluoropropyl)-phenyl |
| 1725. | allyl | 4-((S)-2-fluoropropyl)-phenyl |
| 1726. | allyl | 4-((R)-2-fluoropropyl)-phenyl |
| 1727. | allyl | 4-(3,3-difluoropropyl)-phenyl |
| 1728. | allyl | 4-(3,3,3-trifluoropropyl)-phenyl |
| 1729. | allyl | 4-(1-fluoro-1-methylethyl)-phenyl |
| 1730. | allyl | 4-(2-fluoro-1-methylethyl)-phenyl |
| 1731. | allyl | 4-((S)-2-fluoro-1-methylethyl)-phenyl |
| 1732. | allyl | 4-((R)-2-fluoro-1-methylethyl)-phenyl |
| 1733. | allyl | 4-(2,2-difluoro-1-methylethyl)-phenyl |
| 1734. | allyl | 4-((S)-2,2-difluoro-1-methylethyl)-phenyl |
| 1735. | allyl | 4-((R)-2,2-difluoro-1-methylethyl)-phenyl |
| 1736. | allyl | 4-(2,2,2-trifluoro-1-methylethyl)-phenyl |
| 1737. | allyl | 4-((S)-2,2,2-trifluoro-1-methylethyl)-phenyl |
| 1738. | allyl | 4-((R)-2,2,2-trifluoro-1-methylethyl)-phenyl |
| 1739. | allyl | 4-(2-fluoro-1-fluoromethylethyl)-phenyl |
| 1740. | allyl | 4-(1-difluoromethyl-2,2-difluoroethyl)-phenyl |
| 1741. | allyl | 4-(1,1-dimethyl-2-fluoroethyl)-phenyl |
| 1742. | allyl | 4-methoxyphenyl |
| 1743. | allyl | 4-ethoxyphenyl |
| 1744. | allyl | 4-propoxyphenyl |
| 1745. | allyl | 4-isopropoxyphenyl |
| 1746. | allyl | 4-butoxyphenyl |
| 1747. | allyl | 4-(fluoromethoxy)-phenyl |
| 1748. | allyl | 4-(difluoromethoxy)-phenyl |
| 1749. | allyl | 4-(trifluoromethoxy)-phenyl |
| 1750. | allyl | 3-(trifluoromethoxy)-phenyl |
| 1751. | allyl | 4-(2-fluoroethoxy)-phenyl |
| 1752. | allyl | 4-(2,2-difluoroethoxy)-phenyl |
| 1753. | allyl | 4-(2,2,2-trifluoroethoxy)-phenyl |

TABLE A-continued

| No. | R¹ | Ar |
|---|---|---|
| 1754. | allyl | 4-(1,1,2,2-tetrafluoroethoxy)-phenyl |
| 1755. | allyl | 4-cyclopropylphenyl |
| 1756. | allyl | 4-cyclobutylphenyl |
| 1757. | allyl | 4-cyclopentylphenyl |
| 1758. | allyl | 4-(2,2-difluorocyclopropyl)-phenyl |
| 1759. | allyl | 3,4-difluorophenyl |
| 1760. | allyl | 4-bromo-3-fluorophenyl |
| 1761. | allyl | 4-bromo-2-fluorophenyl |
| 1762. | allyl | 4-bromo-2,5-difluorophenyl |
| 1763. | allyl | 2-fluoro-4-isopropylphenyl |
| 1764. | allyl | 3-fluoro-4-isopropylphenyl |
| 1765. | allyl | 4-(1-hydroxy-1-methylethyl)-phenyl |
| 1766. | allyl | 4-(2-hydroxy-2-methylpropyl)-phenyl |
| 1767. | allyl | 4-acetylphenyl |
| 1768. | allyl | 4-carboxyphenyl |
| 1769. | allyl | 4-cyanophenyl |
| 1770. | allyl | 4-hydroxyphenyl |
| 1771. | allyl | 4-(O-benzyl)-phenyl |
| 1772. | allyl | 4-(2-methoxyethoxy)-phenyl |
| 1773. | allyl | 4-(CH₂—N(CH₃)₂)-phenyl |
| 1774. | allyl | 4-(NH—CO—NH₂)-phenyl |
| 1775. | allyl | 4-(methylsulfanyl)-phenyl |
| 1776. | allyl | 4-(fluoromethylsulfanyl)-phenyl |
| 1777. | allyl | 4-(difluoromethylsulfanyl)-phenyl |
| 1778. | allyl | 4-(trifluoromethylsulfanyl)-phenyl |
| 1779. | allyl | 4-(methylsulfonyl)-phenyl |
| 1780. | allyl | 4-(N-methoxy-N-methyl-amino)-phenyl |
| 1781. | allyl | 4-(methoxyamino)-phenyl |
| 1782. | allyl | 4-(ethoxyamino)-phenyl |
| 1783. | allyl | 4-(N-methylaminooxy)-phenyl |
| 1784. | allyl | 4-(N,N-dimethylaminooxy)-phenyl |
| 1785. | allyl | 4-(azetidin-1-yl)-phenyl |
| 1786. | allyl | 4-(2-methylazetidin-1-yl)-phenyl |
| 1787. | allyl | 4-((S)-2-methylazetidin-1-yl)-phenyl |
| 1788. | allyl | 4-((R)-2-methylazetidin-1-yl)-phenyl |
| 1789. | allyl | 4-(3-fluoroazetidin-1-yl)-phenyl |
| 1790. | allyl | 4-(3-methoxyazetidin-1-yl)-phenyl |
| 1791. | allyl | 4-(3-hydroxyazetidin-1-yl)-phenyl |
| 1792. | allyl | 4-(pyrrolidin-1-yl)-phenyl |
| 1793. | allyl | 4-(pyrrolidin-2-yl)-phenyl |
| 1794. | allyl | 4-(S)-pyrrolidin-2-yl)-phenyl |
| 1795. | allyl | 4-((R)-pyrrolidin-2-yl)-phenyl |
| 1796. | allyl | 4-(pyrrolidin-3-yl)-phenyl |
| 1797. | allyl | 4-((S)-pyrrolidin-3-yl)-phenyl |
| 1798. | allyl | 4-((R)-pyrrolidin-3-yl)-phenyl |
| 1799. | allyl | 4-(2-fluoropyrrolidin-1-yl)-phenyl |
| 1800. | allyl | 4-((S)-2-fluoropyrrolidin-1-yl)-phenyl |
| 1801. | allyl | 4-((R)-2-fluoropyrrolidin-1-yl)-phenyl |
| 1802. | allyl | 4-(3-fluoropyrrolidin-1-yl)-phenyl |
| 1803. | allyl | 4-((S)-3-fluoropyrrolidin-1-yl)-phenyl |
| 1804. | allyl | 4-((R)-3-fluoropyrrolidin-1-yl)-phenyl |
| 1805. | allyl | 4-(2,2-difluoropyrrolidin-1-yl)-phenyl |
| 1806. | allyl | 4-(3,3-difluoropyrrolidin-1-yl)-phenyl |
| 1807. | allyl | 4-(2-methylpyrrolidin-1-yl)-phenyl |
| 1808. | allyl | 4-((S)-2-methylpyrrolidin-1-yl)-phenyl |
| 1809. | allyl | 4-((R)-2-methylpyrrolidin-1-yl)-phenyl |
| 1810. | allyl | 4-(3-methylpyrrolidin-1-yl)-phenyl |
| 1811. | allyl | 4-((S)-3-methylpyrrolidin-1-yl)-phenyl |
| 1812. | allyl | 4-((R)-3-methylpyrrolidin-1-yl)-phenyl |
| 1813. | allyl | 4-(1-methylpyrrolidin-2-yl)-phenyl |
| 1814. | allyl | 4-((S)-1-methylpyrrolidin-2-yl)-phenyl |
| 1815. | allyl | 4-((R)-1-methylpyrrolidin-2-yl)-phenyl |
| 1816. | allyl | 4-(1-methylpyrrolidin-3-yl)-phenyl |
| 1817. | allyl | 4-((S)-1-methylpyrrolidin-3-yl)-phenyl |
| 1818. | allyl | 4-((R)-1-methylpyrrolidin-3-yl)-phenyl |
| 1819. | allyl | 4-(2,2-dimethylpyrrolidin-1-yl)-phenyl |
| 1820. | allyl | 4-(3,3-dimethylpyrrolidin-1-yl)-phenyl |
| 1821. | allyl | 4-(2-trifluoromethylpyrrolidin-1-yl)-phenyl |
| 1822. | allyl | 4-((S)-2-trifluoromethylpyrrolidin-1-yl)-phenyl |
| 1823. | allyl | 4-((R)-2-trifluoromethylpyrrolidin-1-yl)-phenyl |
| 1824. | allyl | 4-(3-trifluoromethylpyrrolidin-1-yl)-phenyl |
| 1825. | allyl | 4-((S)-3-trifluoromethylpyrrolidin-1-yl)-phenyl |
| 1826. | allyl | 4-((R)-3-trifluoromethylpyrrolidin-1-yl)-phenyl |
| 1827. | allyl | 4-(2-oxopyrrolidin-1-yl)-phenyl |
| 1828. | allyl | 4-(2-oxo-oxazolidin-3-yl)-phenyl |
| 1829. | allyl | 4-(piperidin-1-yl)-phenyl |
| 1830. | allyl | 4-(2-methylpiperidin-1-yl)-phenyl |
| 1831. | allyl | 4-((S)-2-methylpiperidin-1-yl)-phenyl |
| 1832. | allyl | 4-((R)-2-methylpiperidin-1-yl)-phenyl |
| 1833. | allyl | 4-(piperazin-1-yl)-phenyl |
| 1834. | allyl | 4-(4-methylpiperazin-1-yl)-phenyl |
| 1835. | allyl | 4-(morpholin-4-yl)-phenyl |
| 1836. | allyl | 4-(thiomorpholin-4-yl)-phenyl |
| 1837. | allyl | 4-(1-oxo-thiomorpholin-4-yl)-phenyl |
| 1838. | allyl | 4-(1,1-dioxo-thiomorpholin-4-yl)-phenyl |
| 1839. | allyl | 4-(pyrrol-1-yl)-phenyl |
| 1840. | allyl | 4-(pyrrol-2-yl)-phenyl |
| 1841. | allyl | 4-(pyrrol-3-yl)-phenyl |
| 1842. | allyl | 4-(1-methylpyrrol-2-yl)-phenyl |
| 1843. | allyl | 4-(1-methylpyrrol-3-yl)-phenyl |
| 1844. | allyl | 4-(furan-2-yl)-phenyl |
| 1845. | allyl | 4-(furan-3-yl)-phenyl |
| 1846. | allyl | 4-(thiophen-2-yl)-phenyl |
| 1847. | allyl | 4-(thiophen-3-yl)-phenyl |
| 1848. | allyl | 4-(5-propylthien-2-yl)-phenyl |
| 1849. | allyl | 4-(pyrazol-1-yl)-phenyl |
| 1850. | allyl | 4-(pyrazol-3-yl)-phenyl |
| 1851. | allyl | 4-(pyrazol-4-yl)-phenyl |
| 1852. | allyl | 4-(1-methyl-1H-pyrazol-4-yl)-phenyl |
| 1853. | allyl | 4-(1-ethyl-1H-pyrazol-4-yl)-phenyl |
| 1854. | allyl | 4-(1-methyl-1H-pyrazol-5-yl)-phenyl |
| 1855. | allyl | 4-(1H-imidazol-2-yl)-phenyl |
| 1856. | allyl | 4-(imidazol-1-yl)-phenyl |
| 1857. | allyl | 4-(1-methylimidazol-2-yl)-phenyl |
| 1858. | allyl | 4-(oxazol-2-yl)-phenyl |
| 1859. | allyl | 4-(oxazol-4-yl)-phenyl |
| 1860. | allyl | 4-(oxazol-5-yl)-phenyl |
| 1861. | allyl | 4-(isoxazol-3-yl)-phenyl |
| 1862. | allyl | 4-(isoxazol-4-yl)-phenyl |
| 1863. | allyl | 4-(isoxazol-5-yl)-phenyl |
| 1864. | allyl | 4-([1,2,3]-triazol-1-yl)-phenyl |
| 1865. | allyl | 4-([1,2,4]-triazol-1-yl)-phenyl |
| 1866. | allyl | 4-([1,2,3]-triazol-2-yl)-phenyl |
| 1867. | allyl | 4-(4H-[1,2,4]-triazol-3-yl)-phenyl |
| 1868. | allyl | 4-([1,2,4]-triazol-4-yl)-phenyl |
| 1869. | allyl | 4-(2H-[1,2,3]-triazol-4-yl)-phenyl |
| 1870. | allyl | 4-(4-methyl-4H-[1,2,4]-triazol-3-yl)-phenyl |
| 1871. | allyl | 4-(2-methyl-2H-[1,2,3]-triazol-4-yl)-phenyl |
| 1872. | allyl | 4-([1,3,4]-oxadiazol-2-yl)-phenyl |
| 1873. | allyl | 4-([1,2,4]-oxadiazol-3-yl)-phenyl |
| 1874. | allyl | 4-([1,2,4]-oxadiazol-5-yl)-phenyl |
| 1875. | allyl | 4-([1,2,3]-oxadiazol-4-yl)-phenyl |
| 1876. | allyl | 4-([1,2,3]-oxadiazol-5-yl)-phenyl |
| 1877. | allyl | 4-([1,2,3]-thiadiazol-4-yl)-phenyl |
| 1878. | allyl | 4-(1H-tetrazol-5-yl)-phenyl |
| 1879. | allyl | 4-(tetrazol-1-yl)-phenyl |
| 1880. | allyl | 4-(2-methyl-2H-tetrazol-5-yl)-phenyl |
| 1881. | allyl | 4-(1-methyl-1H-tetrazol-5-yl)-phenyl |
| 1882. | allyl | 4-furazan-3-yl-phenyl |
| 1883. | allyl | 4-(pyrid-2-yl)-phenyl |
| 1884. | allyl | 4-(pyrid-3-yl)-phenyl |
| 1885. | allyl | 4-(pyrid-4-yl)-phenyl |
| 1886. | allyl | 4-(pyrimidin-2-yl)-phenyl |
| 1887. | allyl | 4-(pyrimidin-4-yl)-phenyl |
| 1888. | allyl | 4-(pyrimidin-5-yl)-phenyl |
| 1889. | allyl | 5-isopropylthiophen-2-yl |
| 1890. | allyl | 2-chlorothiophen-5-yl |
| 1891. | allyl | 2,5-dichlorothiophen-4-yl |
| 1892. | allyl | 2,3-dichlorothiophen-5-yl |
| 1893. | allyl | 2-chloro-3-nitrothiophen-5-yl |
| 1894. | allyl | 2-(phenylsulfonyl)-thiophen-5-yl |
| 1895. | allyl | 2-(pyridin-2-yl)thiophen-5-yl |
| 1896. | allyl | 2-(5-(trifluoromethyl)isoxazol-3-yl)-thiophen-5-yl |
| 1897. | allyl | 2-(2-methylthiazol-4-yl)-thiophen-5-yl |
| 1898. | allyl | 1-methyl-1H-imidazol-4-yl |
| 1899. | allyl | 1,2-dimethyl-1H-imidazol-4-yl |
| 1900. | allyl | 3,5-dimethylisoxazol-4-yl |
| 1901. | allyl | thiazol-2-yl |
| 1902. | allyl | 4-methylthiazol-2-yl |
| 1903. | allyl | 4-isopropylthiazol-2-yl |
| 1904. | allyl | 4-trifluoromethylthiazol-2-yl |

TABLE A-continued

| No. | R¹ | Ar |
|---|---|---|
| 1905. | allyl | 5-methylthiazol-2-yl |
| 1906. | allyl | 5-isopropylthiazol-2-yl |
| 1907. | allyl | 5-trifluoromethylthiazol-2-yl |
| 1908. | allyl | 2,4-dimethylthiazol-5-yl |
| 1909. | allyl | 2-acetamido-4-methylthiazol-5-yl |
| 1910. | allyl | 4H-[1,2,4]triazol-3-yl |
| 1911. | allyl | 5-methyl-4H-[1,2,4]triazol-3-yl |
| 1912. | allyl | 4-methyl-4H-[1,2,4]triazol-3-yl |
| 1913. | allyl | 5-isopropyl-4H-[1,2,4]triazol-3-yl |
| 1914. | allyl | 5-trifluoromethyl-4H-[1,2,4]triazol-3-yl |
| 1915. | allyl | 4,5-dimethyl-4H-[1,2,4]triazol-3-yl |
| 1916. | allyl | 5-isopropyl-4-methyl-4H-[1,2,4]triazol-3-yl |
| 1917. | allyl | 5-trifluoromethyl-4-methyl-4H-[1,2,4]triazol-3-yl |
| 1918. | allyl | [1,3,4]thiadiazol-2-yl |
| 1919. | allyl | 5-methyl-[1,3,4]thiadiazol-2-yl |
| 1920. | allyl | 5-isopropyl-[1,3,4]thiadiazol-2-yl |
| 1921. | allyl | 5-trifluoromethyl-[1,3,4]thiadiazol-2-yl |
| 1922. | allyl | 3-bromo-2-chloropyrid-5-yl |
| 1923. | allyl | 2-(4-morpholino)-pyrid-5-yl |
| 1924. | allyl | 2-phenoxypyrid-5-yl |
| 1925. | allyl | (2-isopropyl)-pyrimidin-5-yl |
| 1926. | allyl | (5-isopropyl)-pyrimidin-2-yl |
| 1927. | allyl | 8-quinolyl |
| 1928. | allyl | 5-isoquinolyl |
| 1929. | allyl | 2-(trifluoroacetyl)-1,2,3,4-tetrahydroisoquinolin-7-yl |
| 1930. | allyl | 5-chloro-3-methylbenzothiophen-2-yl |
| 1931. | allyl | 3,4-dihydro-4-methyl-2H-benzo[b][1,4]oxazinyl |
| 1932. | allyl | benzothiazol-6-yl |
| 1933. | allyl | benzo[2,1,3]oxadiazol-4-yl |
| 1934. | allyl | 5-chlorobenzo[2,1,3]oxadiazol-4-yl |
| 1935. | allyl | 7-chlorobenzo[2,1,3]oxadiazol-4-yl |
| 1936. | allyl | benzo[2,1,3]thiadiazol-4-yl |
| 1937. | allyl | 6-chloroimidazo[2,1-b]thiazolyl |

The compounds of the formula I where E is NH and $R^{1a}$ is hydrogen can be prepared by analogy to methods which are well known in the art, e.g. from the international patent applications cited in the introductory part. A preferred method for the preparation of compounds I is outlined in scheme 1:

carbon atom form a carbonyl group. R has one of the meanings given for $R^1$ or may be an amino-protecting group PG such as benzyl or tert.-butoxycarbonyl. Other suitable amino-protecting groups are disclosed, for example, in P. Kocienski, Protecting Groups, Thieme-Verlag, Stuttgart 2000, Chapter 6.

In step a) of scheme 1, compound II is reacted with an arylsulfonylchloride Cl—$SO_2$—Ar, preferably in the presence of a base, according to standard procedures in the art. The reaction depicted in scheme 1 step a) takes place under the reaction conditions which are customary for preparing arylsulfonamide compounds or arylsulfonic esters, respectively, and which are described, for example, in J. March, Advanced Organic Chemistry, $3^{rd}$ edition, John Wiley & Sons, New York, 1985 p 444 and the literature cited therein, European J. Org. Chem. 2002 (13), pp. 2094-2108, Tetrahedron 2001, 57 (27) pp. 5885-5895, Bioorganic and Medicinal Chemistry Letters, 2000, 10(8), pp. 835-838 and Synthesis 2000 (1), pp. 103-108. The reaction customarily takes place in an inert solvent, for example in an ether, such as diethyl ether, diisopropyl ether, methyl tert-butyl ether or tetrahydrofuran, a halohydrocarbon, such as dichloromethane, an aliphatic or cycloaliphatic hydrocarbon, such as pentane, hexane or cyclohexane, or an aromatic hydrocarbon, such as toluene, xylene, cumene and the like, or in a mixture of the abovementioned solvents. The reaction of II with Cl—$SO_2$—Ar is customarily carried out in the presence of an auxiliary base. Suitable bases are inorganic bases, such as sodium carbonate or potassium carbonate, or sodium hydrogen carbonate or potassium hydrogen carbonate, and organic bases, for example trialkylamines, such as triethylamine, or pyridine compounds, such as pyridine, lutidine and the like. The latter compounds can at the same time serve as solvents. The auxiliary base is customarily employed in at least equimolar quantities, based on the amine compound II.

The obtained compound Ia, corresponds to compound I, if R' and R" are both hydrogen and R is $R^1$. If R' and R"

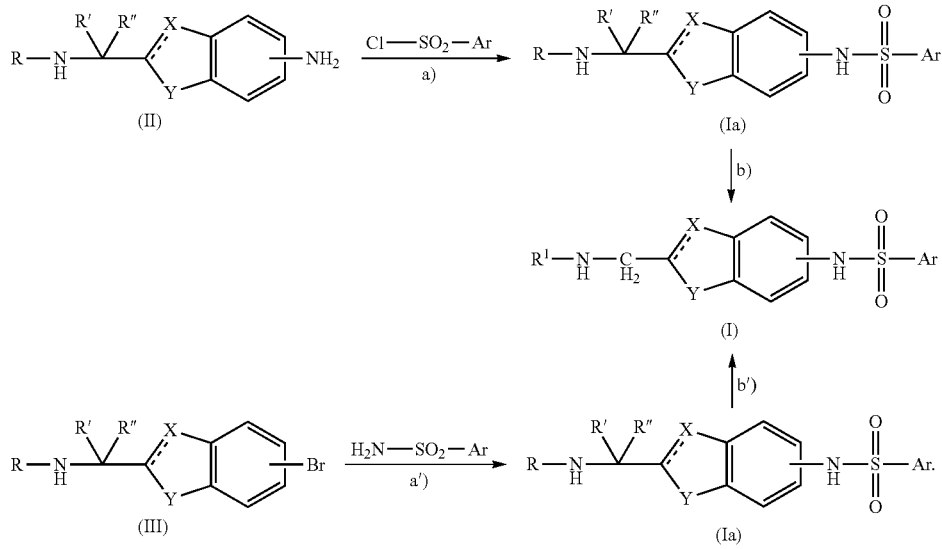

Scheme 1

In scheme 1, $R^1$, X, Y and Ar have the meanings as given above. R' and R" are both hydrogen or together with the represent a carbonyl group, this group will be reduced in step b) of scheme 1 by analogy to known methods, e.g. by reduction with borane, boranedimethylsulfide or by a complex hydride such as lithium aluminiumhydride.

If R is an amino protecting group PG, this group can be cleaved by standard methods to obtain the primary amine (see P. Kocienski, Protecting Groups, loc. cit.). This primary amine can be reacted in the sense of an alkylation, with a compound $R^1$—X. In this compound, $R^1$ is $C_1$-$C_4$-alkyl, $C_3$-$C_4$-cycloalkyl, $C_3$-$C_4$-alkenyl, fluorinated $C_1$-$C_4$-alkyl, fluorinated $C_3$-$C_4$-cycloalkyl, fluorinated $C_3$-$C_4$-alkenyl, and X is a nucleophilically displaceable leaving group, e.g. halogen, trifluoroacetate, alkylsulfonate, arylsulfonate, alkyl sulfate and the like. The reaction conditions which are required for the alkylation have been adequately disclosed, e.g. in Bioorganic and Medicinal Chemistry Lett. 2002, 12(7), pp. 2443-2446 and also 2002, 12(5), pp. 1917-1919.

In case $R^1$ in formula I is hydrogen, compound I or Ia can also be reacted with an acyl halide to obtain a compound of the formula I wherein $R^1$ is $C_1$-$C_3$-alkylcarbonyl. The carbonyl group in these compounds can be reduced with diborane to obtain compounds of the general formula I, wherein $R^1$ is $C_2$-$C_4$-alkyl. The carbonyl group can also be reacted with a fluorinating agent to obtain a compound I wherein $R^1$ is 1,1-difluoroalkyl. Acylation and reduction can be achieved by standard methods, which are discussed in J. March, Advanced Organic Chemistry, 3rd ed. J. Wiley & Sons, New York 1985, p. 370 and 373 (acylation) and p. 1099 f. and in the literature cited in this publication (with regard to acylation, see also Synth. Commun. 1986, 16, p. 267, and with regard to reduction, see also J. Heterocycl. Chem. 1979, 16, p. 1525).

The introduction of $C_2$-$C_4$-alkyl or fluorinated $C_2$-$C_4$-alkyl as a radical $R^1$ into a compound of formula I, wherein both $R^1$ and $R^{1a}$ are hydrogen, can also be achieved, in the sense of a reductive amination, by reacting I [$R^1$=$R^{1a}$=H] with a suitable ketone or aldehyde in the presence of a reducing agent, e.g. in the presence of a borohydride such as sodium borohydride, sodium cyanoborohydride or sodium triacetoxyborohydride. The skilled person is familiar with the reaction conditions which are required for a reductive amination, e.g. from Bioorganic and Medicinal Chemistry Lett. 2002, 12(5), pp. 795-798 and 12(7) pp. 1269-1273.

A skilled person will appreciate, that a compound I, wherein $R^1$ is alkenyl can be converted into a compound wherein $R^1$ is alkyl or fluorinated alkyl by hydrogenation or by addition of hydrogen fluoride or by fluorination with suitable fluorinating agents such as $XeF_2$ or $CoF_3$.

A skilled person will further appreciate, that a radical $R^3$, which is different from hydrogen, can be introduced in either compound I of scheme I or at an earlier stage of the synthesis by a conventional alkylation.

In step a') of scheme 1, a bromine compound III is reacted with an arylsulfonylamide Ar—$SO_2$—$NH_2$ in the presence of a palladium(O) compound such as tris(dibenzylideneacetone)-dipalladium(0) in the presence of a tri(substituted) phosphine, e.g. a triarylphosphine such as triphenylphosphine or tritolylphosphine, tri(cyclo)alkylphosphine such as tris-n-butylphosphine, tris(tert.-butyl)phosphine or tris(cyclohexyl)phosphine, preferably in the presence of a base such as sodium hydride according to the method described in J. Org. Chem., 68 (2993) pp 8274-8276, and outlined below. Thereby a compound Ia is obtained which can be reacted further as described above.

A skilled person will also appreciate, that the methods outlined in scheme 1, can also be applied in the synthesis of compounds I, wherein $R^{1a}$ and $R^2$ or $R^{1a}$ and $R^{2a}$ together are $(CH_2)_n$ with n being 1, 2 or 3.

The compounds of the formula I where E is $CH_2$ and $R^{1a}$ is hydrogen can be prepared by analogy to methods which are well known in the art, e.g. from the international patent applications cited in the introductory part. A preferred method for the preparation of compounds I is outlined in scheme 2:

Scheme 2:

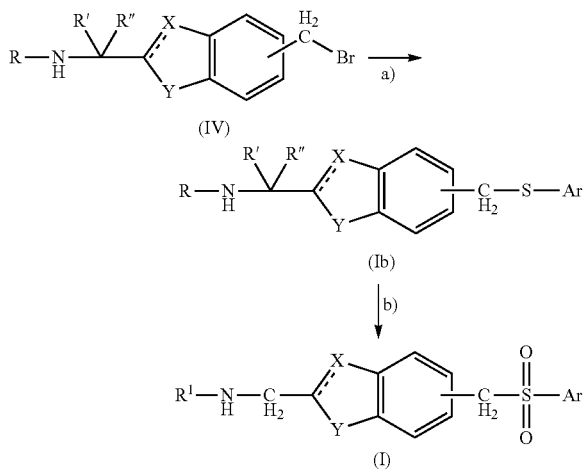

In scheme 2, R, R', R", $R^1$, Ar, X and Y have the meanings given above. According to scheme 2, compound IV is reacted in step a) with a mercapto compound HS—Ar in the presence of a base, such as sodium hydride or sodium alkoxide or with an alkali metal salt thereof thereby yielding thioether compound Ib. The thioether moiety in compound is oxidized to a sulfone moiety, e.g. by oxone (step b). If R is a protective group, R can be cleaved, thereby obtaining compound I, wherein $R^{1a}$ is H. A skilled person understands that I can be further transformed as outlined for scheme 1.

A skilled person will also appreciate, that the methods outlined in scheme 2, can also be applied in the synthesis of compounds I, wherein $R^{1a}$ and $R^2$ or $R^{1a}$ and $R^{2a}$ together are $(CH_2)_n$ with n being 1, 2 or 3.

Compounds of the formula I, wherein E is $NR^3$, X is N and Y is NH can also be prepared by the reaction sequence shown in scheme 3.

Scheme 3:

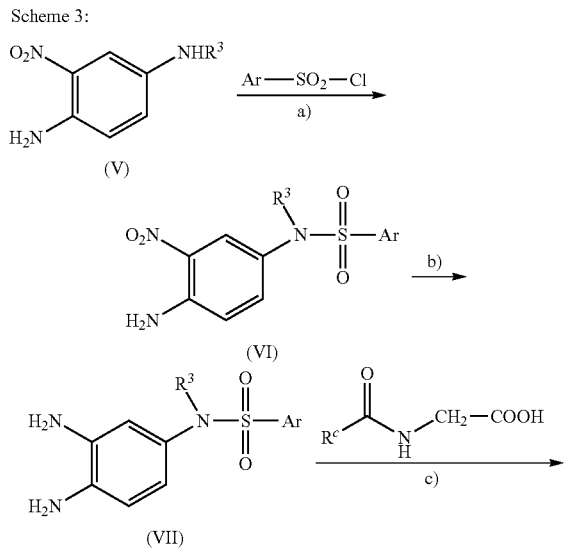

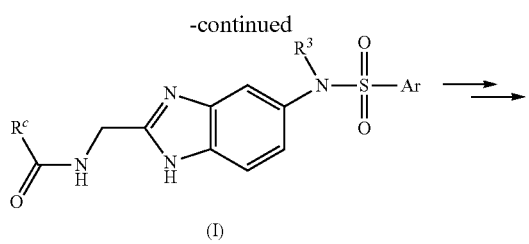

(I)

In scheme 3, $R^3$ and Ar have the meanings given above. $R^c$ is $C_1$-$C_3$-alkyl or fluorinated $C_1$-$C_3$-alkyl.

Step a) of scheme 3 can be performed according to the method described for step a) of scheme 1.

In step b), the nitro group in VI is reduced to the $NH_2$ group in VII. The reaction conditions which are required for step b) correspond to the customary conditions for reducing aromatic nitro groups which have been described extensively in the literature (see, for example, J. March, Advanced Organic Chemistry, 3rd ed., J. Wiley & Sons, New-York, 1985, p. 1183 and the literature cited in this reference). The reduction is achieved, for example, by reacting the nitro compound VI with a metal such as iron, zinc or tin under acidic reaction conditions, i.e. using nascent hydrogen, or using a complex hydride such as lithium aluminum hydride or sodium borohydride, preferably in the presence of transition metal compounds of nickel or cobalt such as $NiCl_2(P(phenyl)_3)_2$, or $CoCl_2$, (see Ono et al. Chem. Ind. (London), 1983 p. 480), or using $NaBH_2S_3$ (see Lalancette et al. Can. J. Chem. 49, 1971, p. 2990), with it being possible to carry out these reductions, depending on the given reagent, in substance or in a solvent or diluent. Alternatively, the reduction of VI to VII can be carried out with hydrogen in the presence of a transition metal catalyst, e.g. using hydrogen in the presence of catalysts based on platinum, palladium, nickel, ruthenium or rhodium. The catalysts can contain the transition metal in elemental form or in the form of a complex compound, of a salt or of an oxide of the transition metal, with it being possible, for the purpose of modifying the activity, to use customary coligands, e.g. organic phosphine compounds, such as triphenylphosphine, tricyclohexylphosphine or tri-n-butylphosphine or phosphites. The catalyst is customarily employed in quantities of from 0.001 to 1 mol per mol of compound VI, calculated as catalyst metal. In a preferred variant, the reduction is effected using tin(II) chloride in analogy with the methods described in Bioorganic and Medicinal Chemistry Letters, 2002, 12(15), pp. 1917-1919 and J. Med. Chem. 2002, 45(21), pp. 4679-4688. The reaction of VI with tin(II) chloride is preferably carried out in an inert organic solvent, preferably an alcohol such as methanol, ethanol, isopropanol or butanol.

In step c) compound VII is reacted with an acylated derivative of glycine in the presence of a carbodiimide such as N'-(3-dimethylamino)propyl-N'-ethylcarbodiimid and optionally an organic buffer such as hydroxy-7-azabenzotriazole/tertiary amine such as diisopropylethylamine. Thereby a compound I is obtained, wherein $R^1$ is $C_1$-$C_3$-alkylcarbonyl or fluorinated $C_1$-$C_3$-alkylcarbonyl. The carbonyl group in these compounds can be reduced to a $CH_2$-moiety either with diborane, borane-dimethylsulfide or lithium aluminium hydride to obtain compounds of the general formula I, wherein R is $CH_2$-(optionally fluorinated $C_1$-$C_3$-alkyl) (see e.g. see also J. Heterocycl. Chem. 1979, 16, p. 1525). The carbonyl group can also be reacted with a fluorinating agent to obtain a compound I wherein $R^1$ is 1,1-difluoroalkyl. The optionally fluorinated $C_1$-$C_3$-alkylcarbonyl group can also be cleaved.

Compounds of the formula II, III, IV and V are known in the art. They can also be prepared by standard methods, e.g. by a nitration/reduction sequence (compounds II), by bromination of the aromatic core (compounds III) or by side chain bromination or by hydroxymethylation followed by OH/bromine exchange (compounds IV). Each of these methods may apply suitable protecting groups.

Compounds of the formula II, wherein X ⋯ C(R)—Y form a saturated carbocycle can be obtained by the reaction sequences shown in the following schemes 4 and 5:

Scheme 4:

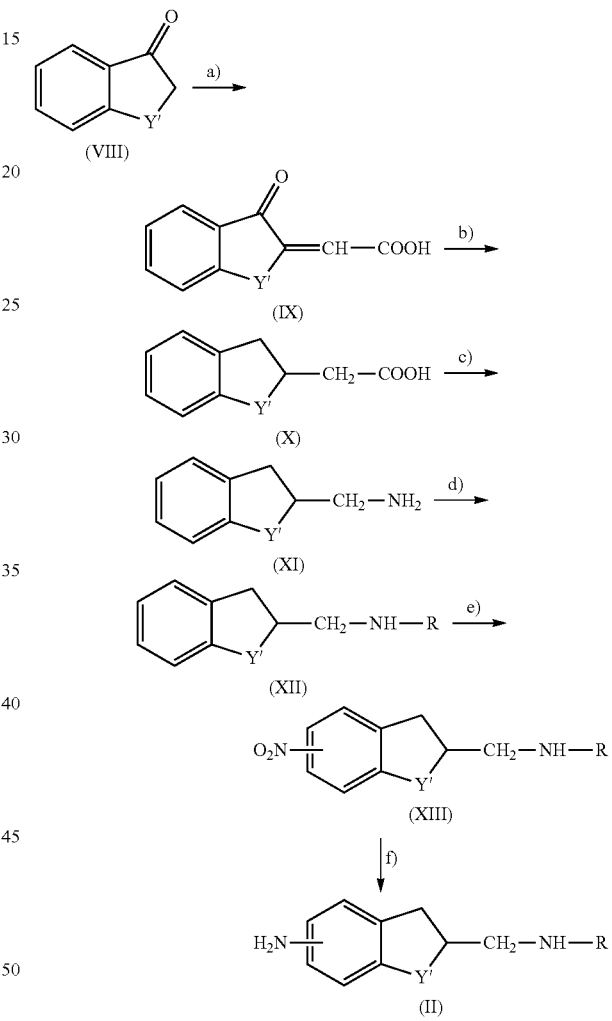

In scheme 4 Y' is $CH_2$ or $CH_2CH_2$. R is $C_1$-$C_3$-alkylcarbonyl or an amino-protecting group PG.

In step a) a one-pot reaction involving the addition of glycolic acid to ketone VIII, with subsequent dehydration in the presence of an acid such as sulphuric acid (J. Org. Chem. 1994, 37, 2071-2078), generates the requisite α,β-unsaturated ketone IX. Concomitant catalytic hydrogenation of the double bond and reduction of the keto-group in IX can be performed using a catalyst such as Pd—C (step b, J. Org. Chem. 1994, 37, 2071-2078). Conversion of the carboxylic acid X to the primary amine may XI be accomplished by reaction of DPPA in benzyl alcohol followed by catalytic hydrogenation using a catalyst such as Pd—C (step c, Bioorg. Med. Chem. Lett., 1999, 9(3), 401-406). In step d, the amine XI is acylated or protected as outlined for scheme 1. Subsequent nitration (step e) and reduction of the nitro group (as outlined for scheme 2) yields the desired amine II.

Scheme 5:

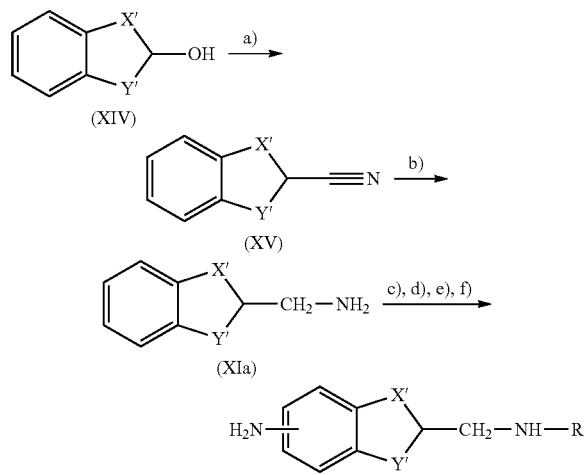

In scheme 5 X' is absent, CH$_2$ or CH$_2$CH$_2$, Y' is CH$_2$, CH$_2$CH$_2$ or CH$_2$CH$_2$CH$_2$. R is C$_1$-C$_3$-alkylcarbonyl or an amino-protecting group PG.

According to scheme 5, compound XIV is converted into the mesylate by reacting XIV with mesylchloride in the presence of a tertiary amine such as diisopropylethylamine and optionally a catalyst such as dimethylaminophenol. The mesylate of XIV is then reacted with a cyanide such as tetraethylammonium cyanide to obtain the nitrile compound XV. The nitrile XV is then hydrogenated by suitable means, e.g. by a complex hydride such as lithium aluminiumhydride, thereby yielding the primary amine XIa, which can be converted into the amine II by analogy to scheme 4.

Compounds of the formula III, wherein X⋯C(R)—Y form a saturated carbocycle can be obtained by the reaction sequences shown in the following scheme 6.

Scheme 6:

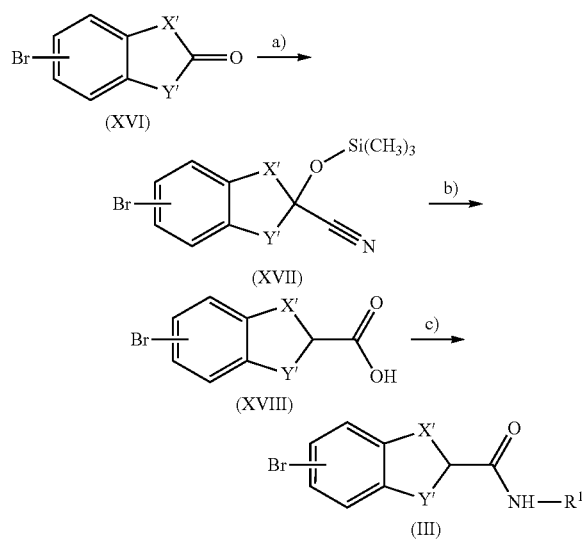

In scheme 6 X' is absent, i.e. a single bond, or CH$_2$ or CH$_2$CH$_2$, Y' is CH$_2$, CH$_2$CH$_2$ or CH$_2$CH$_2$CH$_2$. R$^1$ has the meanings as given above.

In step a) of scheme 6, the ketone XVI is reacted with trimethylsilylcyanide in the presence of a weak Lewis acid such as zinc iodide, whereby compound XVII is obtained. Compound XVII is then reacted with stannous(II) chloride in methanolic HCl, whereby the acid XVIII is obtained. The acid is then reacted with an amine R$^1$—NH$_2$ to obtain compound III.

A further approach to compounds I, wherein E is NH is shown in scheme 7.

Scheme 7:

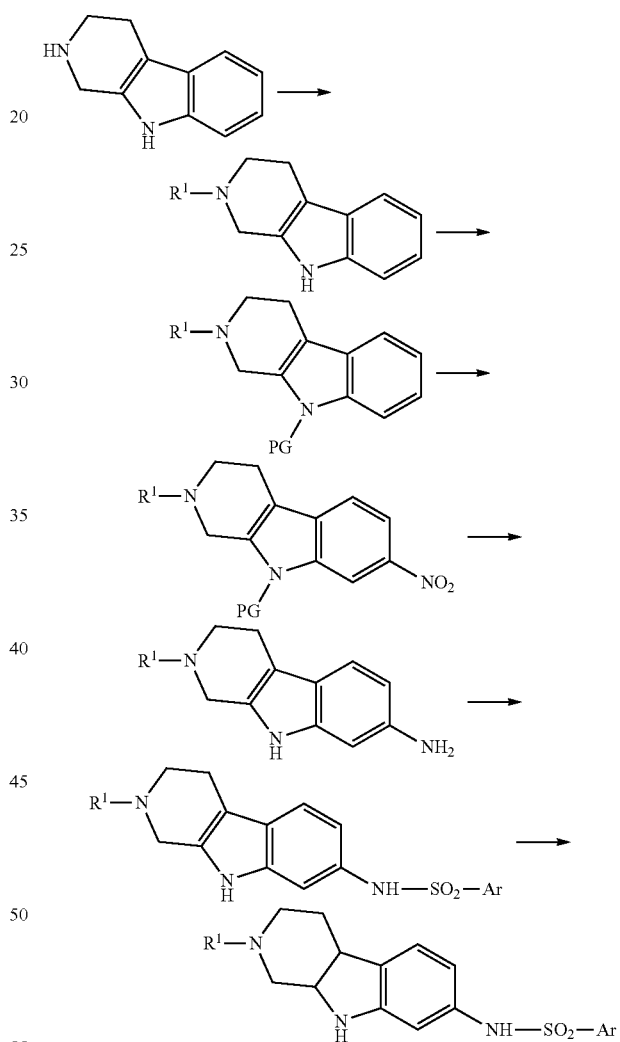

In scheme 7, R$^1$ is different from hydrogen. PG is a protective group, e.g. an acetyl group.

Starting from commercially available tryptoline (2,3,4,9-tetrahydro-1H-beta-carboline), a radical R$^1$ is introduced either by alkylation or acylation as outlined for scheme 1. After protection of the indoline nitrogen, a nitration is performed according to Synthetic Communications (2003), 33, 3707-3716. The separation of the obtained isomers can be achieved by flash chromatography. Nitration and reduction to the amine can also be achieved according to the method described in Journal of the Chemical Society, Perkin Transactions 2: Physical Organic Chemistry (1991), 11, 1729-1734 and in Taiwan Yixuehui Zazki (1960), 59, 550-555. The amine is then reacted with Ar—SO$_2$—Cl as described for scheme 1 and the obtained compound can be hydrogenated.

If not indicated otherwise, the above-described reactions are generally carried out in a solvent at temperatures between room temperature and the boiling temperature of the solvent employed. Alternatively, the activation energy which is required for the reaction can be introduced into the reaction mixture using microwaves, something which has proved to be of value, in particular, in the case of the reactions catalyzed by transition metals (with regard to reactions using microwaves, see Tetrahedron 2001, 57, p. 9199 ff. p. 9225 ff. and also, in a general manner, "Microwaves in Organic Synthesis", André Loupy (Ed.), Wiley-VCH 2002).

C$_6$H$_5$—CH$_2$—S—Ar with chlorine (Synthesis, 1998, 36-38; J. Am. Chem. Soc., 1950, 74, 4890-92) directly to the corresponding sulfonyl chlorides. The further are known in the art or may be prepared by standard methods. E.g. mercaptopyrimidines or pyrimidinyl-benzylthioether precursors can be prepared according to literature (Chemische Berichte, 1960, 1208-11; Chemische Berichte, 1960, 95, 230-235; Collection Czechoslow. Chem. Comm., 1959, 24, 1667-1671; Austr. J. Chem., 1966, 19, 2321-30; Chemiker-Zeitung, 101, 6, 1977, 305-7; Tetrahedron, 2002, 58, 887-890; Synthesis, 1983, 641-645.

In the following schemes 8 to 10 several routes are shown which are suitable to prepare benzenesulfonyl chlorides carrying fluorinated propyl radical.

Scheme 8:

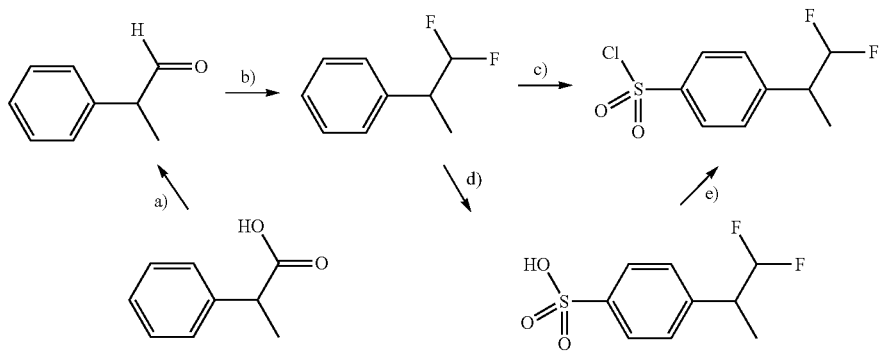

The sulfonylchlorides Cl—SO$_2$—Ar are either commercially available or can be prepared according to standard synthetic methods. Sulfonylchlorides containing a fluorinated radical R$^a$ may be prepared by different synthetic routes, e.g. by reacting suitable hydroxy or oxo precursor (e.g. a compound Cl—SO$_2$—Ar, carrying a hydroxy or oxo substituted radical) with fluorinating reagents like DAST (diethylaminosulfurtrifluoride), morpholine-DAST, deoxofluor (bis(2-methoxyethyl)aminosulfur trifluoride), Ishikawa's reagent (N,N-diethyl-(1,1,2,3,3,3-hexafluoropropyl)amine; Journal of Fluorine Chemistry, 1989, 43, 371-377). More conventionally, the hydroxy group of an aromatic compound which carries a hydroxy substituted radical but not a chlorosulfonyl group, is transformed into a leaving group which is then replaced by a fluoride ion (J. Org. Chem., 1994, 59, 2898-22901; Tetrahedron Letters, 1998, 7305-6; J. Org. Chem., 1998, 63, 9587-9589, Synthesis, 1987, 920-21)). Subsequent direct chlorosulfonylation with chlorosulfonic acid (Heterocycles, 2001, 55, 9, 1789-1803; J. Org. Chem., 2000, 65, 1399-1406) or a two step process preparing first the sulfonic acid derivatives which are then transformed to the sulfonylchlorides with e.g. chlorosulfonic acid, phosphorous pentachloride (Eur. J. Med. Chem., 2002, 36, 809-828) and the like, yields the desired sulfonylchloride (Tetrahedron Letters, 1991, 33,50 7787-7788)). Sulfonylchlorides may also be prepared by diazotization of suitable amine precursor Ar—NH$_2$ with sodium nitrite under acidic conditions and reaction with sulfur dioxide in acetic acid (scheme (iii); J. Org. Chem., 1960, 25, 1824-26); by oxidation of suitable heteroaryl-thiols HS—Ar or heteroaryl-benzyl-thioethers The 4-(1,1-difluoropropan-2-yl)benzene-1-sulfonyl chloride intermediate can be prepared from the commercially available 2-phenylpropanoic acid. In the first step a) the 2-phenylpropanic acid is converted to the alkyl ester by esterification with an alcohol (e.g. methanol or ethanol) under acid catalysis (e.g. HCl, SO$_2$Cl$_2$). The ester can be reduced to the corresponding 2-phenyl propanal by a reducing agent such as DIBAL (diisobutylaluminium hydride). The aldehyde is converted to the 1,1-difluoro-2-propyl derivative by reaction with a suitable fluorinating reagent like DAST (diethylaminosulfurtrifluoride), morpholine-DAST, deoxo-fluor (bis(2-methoxyethyl)aminosulfur trifluoride), Ishikawa's reagent (N,N-diethyl-(1,1,2,3,3,3-hexafluoropropyl)amine; Journal of Fluorine Chemistry, 1989, 43, 371-377) (step b). The thus obtained 1,1-difluoro-2-phenylpropane can be converted into 4-(1,1-difluoro-2-propyl)benzenesulfonyl chloride by either direct chlorosulfonylation with chlorosulfonic acid (Heterocycles, 2001, 55, 9, 1789-1803; J. Org. Chem., 2000, 65, 1399-1406) (step c) or by a two step process preparing first the sulfonic acid derivatives (step d) which are then transformed to the sulfonylchlorides (step e) by reaction with e.g. chlorosulfonic acid, phosphorous pentachloride (Eur. J. Med. Chem., 2002, 36, 809-828); through diazotisation of suitable amine precursors with sodium nitrite under acidic conditions and reaction with sulfur dioxide in acetic acid (J. Org. Chem., 1960, 25, 1824-26); oxidation of suitable heteroaryl-thiols or heteroaryl-benzyl-thioethers with chlorine (Synthesis, 1998, 36-38; J. Am. Chem. Soc., 1950, 74, 4890-92) directly to the corresponding sulfonyl chlorides.

The synthesis shown in scheme 8 can also be performed using (R)-2-phenylpropanic acid and (S)-2-phenylpropanic acid respectively to give the corresponding chiral 4-(1,1-difluoropropan-2-yl)benzene-1-sulfonyl chlorides.

Scheme 9:

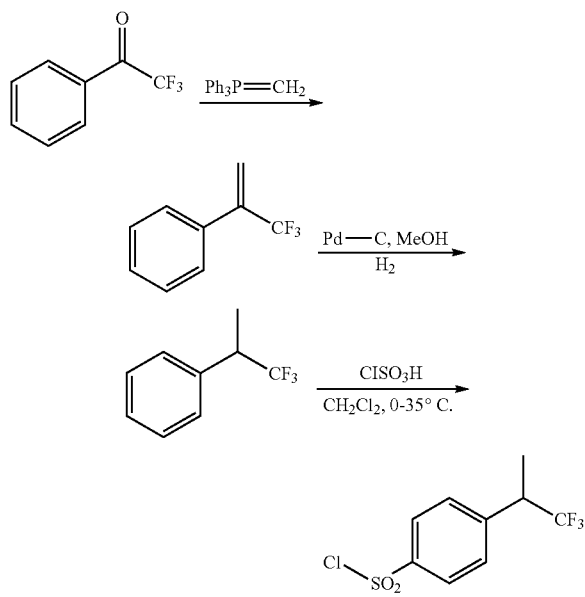

4-(1,1,1-Trifluoropropan-2-yl)benzene-1-sulfonyl chloride intermediate can be prepared from the commercially available 2,2,2-trifluoro-1-phenylethanone by a synthetic route shown in scheme 9. The ketone can be converted to the 3,3,3-trifluoro-2-phenylpropene by a Wittig reaction with a suitable ylide such as methylene-triphenylphosphane (prepared by reaction of methyltriphenylphosphonium halide and a suitable base such as lithium diisopropylamide or potassium tert-butoxide) or according to a Horner-Emmons reaction by reacting the ketone with a suitable phosphonate such as diethyl methylphosphonate and a suitable base such as lithium diisopropylamide or potassium tert-butoxide. The thus obtained 3,3,3-trifluoro-2-phenylpropene can then be reduced to the saturated alkane by catalytic hydrogenation (eg Pd—C) followed by conversion to the sulfonyl chloride by the methods described in scheme 8.

The synthesis of scheme 9 can also be performed using a chiral catalyst for the alkene hydrogenation to allow the preparation of the corresponding chiral 4-(1,1,1-triifluoropropan-2-yl)benzene-1-sulfonyl chlorides.

Scheme 10:

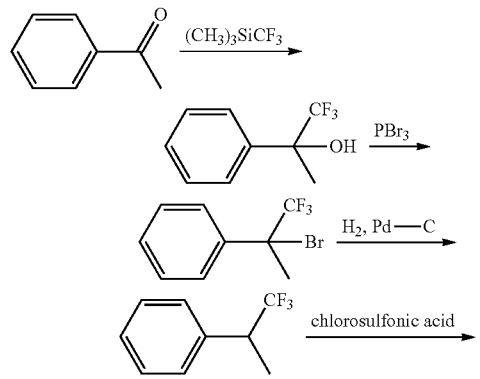

-continued

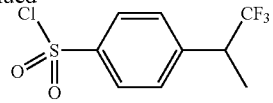

The 4-(1,1,1-trifluoropropan-2-yl)benzene-1-sulfonyl chloride can be also prepared from the commercially available 1-phenyl-ethanone by a four step procedure as shown in scheme 10. The ketone can be converted to the trifluoromethyl hydroxyl intermediate by reaction with trimethyl-trifluoromethyl-silane (Journal of Organic Chemistry, 2000, 65, 8848-8856; Journal of Fluorine Chemistry, 2003, 122, 243-246) which can then be converted to the trifluoromethyl bromide (Journal of the American Chemical Society, 1987, 109, 2435-4). Dehalogenation by catalytic hydrogenation (eg Pd—C) can then be followed by conversion to the sulfonyl chloride by the methods discussed above.

Examples of solvents which can be used are ethers, such as diethyl ether, diisopropyl ether, methyl tert-butyl ether or tetrahydrofuran, aprotic polar solvent, such as dimethylformamide, dimethyl sulfoxide, dimethoxyethane, and acetonitrile, aromatic hydrocarbons, such as toluene and xylene, ketones, such as acetone or methyl ethyl ketone, halohydrocarbons, such as dichloromethane, trichloromethane and dichloroethane, esters, such as ethyl acetate and methyl butyrate, carboxylic acids, such as acetic acid or propionic acid, and alcohols, such as methanol, ethanol, n-propanol, isopropanol, n-butanol, isobutanol, 2-butanol and tert.-butanol.

If desired, it is possible for a base to be present in order to neutralize protons which are released in the reactions. Suitable bases include inorganic bases, such as sodium carbonate, potassium carbonate, sodium hydrogen carbonate or potassium hydrogen carbonate, and, in addition, alkoxides, such as sodium methoxide or sodium ethoxide, alkali metal hydrides, such as sodium hydride, and also organometallic compounds, such as butyllithium compounds or alkylmagnesium compounds, or organic nitrogen bases, such as triethylamine or pyridine. The latter compounds can at the same time serve as solvents.

The crude product is isolated in a customary manner, for example by filtering, distilling off the solvent or extracting from the reaction mixture, etc. The resulting compounds can be purified in a customary manner, for example by means of recrystallizing from a solvent, by means of chromatography or by means of converting into an acid addition salt.

The acid addition salts are prepared in a customary manner by mixing the free base with a corresponding acid, where appropriate in solution in an organic solvent, for example a lower alcohol, such as methanol, ethanol or propanol, an ether, such as methyl tert-butyl ether or diisopropyl ether, a ketone, such as acetone or methyl ethyl ketone, or an ester, such as ethyl acetate.

The compounds according to the invention of the formula I are surprisingly highly selective dopamine $D_3$ receptor ligands which, because of their low affinity for other receptors such as $D_1$ receptors, $D_4$ receptors, $\alpha$1-adrenergic and/or $\alpha$2-adrenergic receptors, muscarinergic receptors, histamine receptors, opiate receptors and, in particular, dopamine $D_2$ receptors, give rise to fewer side-effects than do the classic neuroleptics, which are $D_2$ receptor antagonists. A compound of the invention can be a dopamine $D_3$ receptor agonist, including partial agonistic activity, or a dopamine $D_3$ receptor antagonist, including partial antagonistic activity.

The high affinity of the compounds according to the invention for $D_3$ receptors is reflected in very low in-vitro receptor binding constants ($K_i(D_3)$ values) of as a rule less than 50 nM (nmol/l), preferably of less than 10 nM and, in particular of less than 5 nM. The displacement of [$^{125}$I]-iodosulpride can, for example, be used in receptor binding studies for determining binding affinities for $D_3$ receptors.

The selectivity of the compounds according to the invention, i.e. the ratio $K_i(D_2)/K_i(D_3)$ of the receptor binding constants, is as a rule at least 50, preferably at least 100, even better at least 150. The displacement of [$^3$H]SCH23390, [$^{125}$I] iodosulpride or [$^{125}$I] spiperone can be used, for example, for carrying out receptor binding studies on $D_1$, $D_2$ and $D_4$ receptors.

Because of their binding profile, the compounds can be used for treating diseases which respond to dopamine $D_3$ receptor ligands (or which are susceptible to treatment with a dopamine $D_3$ receptor ligand, respectively), i.e. they are effective for treating those medical disorders or diseases in which exerting an influence on (modulating) the dopamine $D_3$ receptors leads to an improvement in the clinical picture or to the disease being cured. Examples of these diseases are disorders or diseases of the central nervous system.

Disorders or diseases of the central nervous system are understood as meaning disorders which affect the spinal chord and, in particular, the brain. Within the meaning of the invention, the term "disorder" denotes disturbances and/or anomalies which are as a rule regarded as being pathological conditions or functions and which can manifest themselves in the form of particular signs, symptoms and/or malfunctions. While the treatment according to the invention can be directed toward individual disorders, i.e. anomalies or pathological conditions, it is also possible for several anomalies, which may be causatively linked to each other, to be combined into patterns, i.e. syndromes, which can be treated in accordance with the invention.

The disorders which can be treated in accordance with the invention are, in particular, psychiatric and neurological disturbances. These disturbances include, in particular, organic disturbances, including symptomatic disturbances, such as psychoses of the acute exogenous reaction type or attendant psychoses of organic or exogenous cause, e.g., in association with metabolic disturbances, infections and endocrinopathogies; endogenous psychoses, such as schizophrenia and schizotype and delusional disturbances; affective disturbances, such as depressions, mania and/or manic-depressive conditions; and also mixed forms of the above-described disturbances; neurotic and somatoform disturbances and also disturbances in association with stress; dissociative disturbances, e.g. loss of consciousness, clouding of consciousness, double consciousness and personality disturbances; disturbances in attention and waking/sleeping behavior, such as behavioral disturbances and emotional disturbances whose onset lies in childhood and youth, e.g. hyperactivity in children, intellectual deficits, in particular attention disturbances (attention deficit disorders), memory disturbances and cognitive disturbances, e.g. impaired learning and memory (impaired cognitive function), dementia, narcolepsy and sleep disturbances, e.g. restless legs syndrome; development disturbances; anxiety states, delirium; sexlife disturbances, e.g. impotence in men; eating disturbances, e.g. anorexia or bulimia; addiction; and other unspecified psychiatric disturbances.

The disorders which can be treated in accordance with the invention also include Parkinson's disease and epilepsy and, in particular, the affective disturbances connected thereto.

The addiction diseases include psychic disorders and behavioral disturbances which are caused by the abuse of psychotropic substances, such as pharmaceuticals or narcotics, and also other addiction diseases, such as addiction to gaming (impulse control disorders not elsewhere classified). Examples of addictive substances are: opioids (e.g. morphine, heroin and codeine), cocaine; nicotine; alcohol; substances which interact with the GABA chloride channel complex, sedatives, hypnotics and tranquilizers, for example benzodiazepines; LSD; cannabinoids; psychomotor stimulants, such as 3,4-methylenedioxy-N-methylamphetamine, (ecstasy); amphetamine and amphetamine-like substances such as methylphenidate and other stimulants including caffeine. Addictive substances which come particularly into consideration are opioids, cocaine, amphetamine or amphetamine-like substances, nicotine and alcohol.

With regard to the treatment of addiction diseases, particular preference is given to those compounds according to the invention of the formula I which themselves do not possess any psychotropic effect. This can also be observed in a test using rats, which, after having been administered compounds which can be used in accordance with the invention, reduce their self administration of psychotropic substances, for example cocaine.

According to another aspect of the present invention, the compounds according to the invention are suitable for treating disorders whose causes can at least partially be attributed to an anomalous activity of dopamine $D_3$ receptors.

According to another aspect of the present invention, the treatment is directed, in particular, toward those disorders which can be influenced, within the sense of an expedient medicinal treatment, by the binding of preferably exogeneously administered binding partners (ligands) to dopamine $D_3$ receptors.

The diseases which can be treated with the compounds according to the invention are frequently characterized by progressive development, i.e. the above-described conditions change over the course of time; as a rule, the severity increases and conditions may possibly merge into each other or other conditions may appear in addition to those which already exist.

The compounds according to the invention can be used to treat a large number of signs, symptoms and/or malfunctions which are connected with the disorders of the central nervous system and, in particular, the abovementioned conditions. These signs, symptoms and/or malfunctions include, for example, a disturbed relationship to reality, lack of insight and ability to meet customary social norms or the demands made by life, changes in temperament, changes in individual drives, such as hunger, sleep, thirst, etc., and in mood, disturbances in the ability to observe and combine, changes in personality, in particular emotional liability, hallucinations, ego-disturbances, distractedness, ambivalence, autism, depersonalization and false perceptions, delusional ideas, chanting speech, lack of synkinesis, short-step gait, flexed posture of trunk and limbs, tremor, poverty of facial expression, monotonous speech, depressions, apathy, impeded spontaneity and decisiveness, impoverished association ability, anxiety, nervous agitation, stammering, social phobia, panic disturbances, withdrawal symptoms in association with dependency, maniform syndromes, states of excitation and confusion, dysphoria, dyskinetic syndromes and tic disorders, e.g. Huntington's chorea and Gilles-de-la-Tourette's syndrome, vertigo syndromes, e.g. peripheral positional, rotational and oscillatory vertigo, melancholia, hysteria, hypochondria and the like.

Within the meaning of the invention, a treatment also includes a preventive treatment (prophylaxis), in particular as relapse prophylaxis or phase prophylaxis, as well as the treatment of acute or chronic signs, symptoms and/or malfunctions. The treatment can be orientated symptomatically, for example as the suppression of symptoms. It can be effected over a short period, be orientated over the medium term or can be a long-term treatment, for example within the context of a maintenance therapy.

Therefore the compounds according to the invention are preferentially suitable for treating diseases of the central nervous system, in particular for treating affective disorders; neurotic disturbances, stress disturbances and somatoform disturbances and psychoses, and, in particular, for treating schizophrenia and depression. Because of their high selectivity with regard to the $D_3$ receptor, the compounds I according to the invention are also suitable for treating disturbances of kidney function, in particular disturbances of kidney function which are caused by diabetes mellitus (see WO 00/67847) and, especially, diabetic nephropathy.

Within the context of the treatment, the use according to the invention of the described compounds involves a method. In this method, an effective quantity of one or more compounds, as a rule formulated in accordance with pharmaceutical and veterinary practice, is administered to the individual to be treated, preferably a mammal, in particular a human being, productive animal or domestic animal. Whether such a treatment is indicated, and in which form it is to take place, depends on the individual case and is subject to medical assessment (diagnosis) which takes into consideration signs, symptoms and/or malfunctions which are present, the risks of developing particular signs, symptoms and/or malfunctions, and other factors.

As a rule, the treatment is effected by means of single or repeated daily administration, where appropriate together, or alternating, with other active compounds or active compound-containing preparations such that a daily dose of preferably from about 0.1 to 1000 mg/kg of bodyweight, in the case of oral administration, or of from about 0.1 to 100 mg/kg of bodyweight, in the case of parenteral administration, is supplied to an individual to be treated.

The invention also relates to the production of pharmaceutical compositions for treating an individual, preferably a mammal, in particular a human being, productive animal or domestic animal. Thus, the ligands are customarily administered in the form of pharmaceutical compositions which comprise a pharmaceutically acceptable excipient together with at least one compound according to the invention and, where appropriate, other active compounds. These compositions can, for example, be administered orally, rectally, transdermally, subcutaneously, intravenously, intramuscularly or intranasally.

Examples of suitable pharmaceutical formulations are solid medicinal forms, such as powders, granules, tablets, in particular film tablets, lozenges, sachets, cachets, sugar-coated tablets, capsules, such as hard gelatin capsules and soft gelatin capsules, suppositories or vaginal medicinal forms, semisolid medicinal forms, such as ointments, creams, hydrogels, pastes or plasters, and also liquid medicinal forms, such as solutions, emulsions, in particular oil-in-water emulsions, suspensions, for example lotions, injection preparations and infusion preparations, and eyedrops and eardrops. Implanted release devices can also be used for administering inhibitors according to the invention. In addition, it is also possible to use liposomes or microspheres.

When producing the compositions, the compounds according to the invention are optionally mixed or diluted with one or more excipients. Excipients can be solid, semisolid or liquid materials which serve as vehicles, carriers or medium for the active compound.

Suitable excipients are listed in the specialist medicinal monographs. In addition, the formulations can comprise pharmaceutically acceptable carriers or customary auxiliary substances, such as glidants; wetting agents; emulsifying and suspending agents; preservatives; antioxidants; antiirritants; chelating agents; coating auxiliaries; emulsion stabilizers; film formers; gel formers; odor masking agents; taste corrigents; resin; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white-mineral oils. A formulation in this regard is based on specialist knowledge as described, for example, in Fiedler, H. P., Lexikon der Hilfsstoffe für Pharmazie, Kosmetik and angrenzende Gebiete [Encyclopedia of auxiliary substances for pharmacy; cosmetics and related fields], $4^{th}$ edition, Aulendorf: ECV-Editio-Kantor-Verlag, 1996.

The following examples serve to explain the invention without limiting it.

The compounds were either characterized via proton-NMR in $d_6$-dimethylsulfoxide or d-chloroform, if not stated otherwise, on a 400 MHz or 500 MHz NMR instrument (Bruker AVANCE), or by mass spectrometry, generally recorded via HPLC-MS in a fast gradient on C18-material (electrospray-ionisation (ESI) mode), or melting point.

The magnetic nuclear resonance spectral properties (NMR) refer to the chemical shifts (δ) expressed in parts per million (ppm). The relative area of the shifts in the $^1$H NMR spectrum corresponds to the number of hydrogen atoms for a particular functional type in the molecule. The nature of the shift, as regards multiplicity, is indicated as singlet (s), broad singlet (s. br.), doublet (d), broad doublet (d br.), triplet (t), broad triplet (t br.), quartet (q), quintet (quint.) and multiplet (m).

PREPARATION EXAMPLES

I. Preparation of Intermediates a. Synthesis of Sulfonyl Chlorides a.1 4-((S)-2-Fluoro-1-methyl-ethyl)-benzenesulfonyl chloride a.1.1 Toluene-4-sulfonic acid (S)-2-phenyl-propyl ester To a solution of 20 g of (S)-(−)-2-phenyl-1-propanol in 240 ml of dichloromethane was added in portions 28 g of p-toluenesulfonyl chloride (146.8 mmol). After stirring for 18 h at room temperature, the organic phase was washed with 100 ml of water, dried over magnesium sulfate, filtered, and the solvent evaporated under reduced pressure to yield 43 g of the title compound.

$^1$H-NMR (CDCl$_3$, 400 MHz): δ [ppm] 7.65 (d, 2H), 7.15-7.3 (m, 5H), 7.1 (d, 2H), 4.0-4.1 (m, 2H), 3.1 (m, 1H), 2.4 (s, 3H), 1.3 (d, 3H).

a.1.2 ((S)-2-Fluoro-1-methyl-ethyl)-benzene 9.62 g of toluene-4-sulfonic acid (S)-2-phenyl-propyl ester (33.13 mmol) were dissolved in 80 ml of polyethylenglycol 400. 9.62 g of potassium fluoride (165.6 mmol) were added and the reaction mixture was stirred at 50° C. for 3 days and another 2 days at 55-70° C. The reaction was treated with 150 ml of saturated aqueous sodium chloride solution, extracted three times with diethyl ether, and the combined organic layers were dried over magnesium sulfate, filtered, and the solvent was evaporated under reduced pressure. The crude product was purified via silica gel chromatography using cyclohexyane/ethyl acetate 15% as eluent. 2.85 g of the desired product were isolated, containing ~25% of the elimination side product.

$^1$H-NMR (CDCl$_3$, 400 MHz): δ [ppm] 7.2-7.4 (m, 5H), 4.3-4.6 (several m, 2H), 3.15 (m, 1H).1.3 (m, 3H).

a.1.3 4-((S)-2-Fluoro-1-methyl-ethyl)-benzenesulfonyl chloride 3.5 g of ((S)-2-fluoro-1-methyl-ethyl)-benzene (25.32 mmol) were dissolved in 80 ml of dichloromethane. At 0-5° C., 11.81 g of chlorosulfonic acid (101.31 mmol), dissolved in 20 ml of dichloromethane, were added dropwise. The reaction mixture was stirred for 30 min at room temperature and 2 h at 30° C. The solvent was evaporated. 150 ml of diethyl ether were added to the residue, washed once with 150 ml of water, and the organic layer was dried over magnesium sulfate, filtered, and the solvent evaporated under reduced pressure. The crude product was purified via silica gel chromatography with n-heptane-dichloromethane (6:4) as eluent to give 1.5 g of the title compound.

$^1$H-NMR (CDCl$_3$, 400 MHz): δ [ppm] 8.0 (d, 2H), 7.5 (d, 2H), 4.5 (dd, 2H), 3.25 (m, 1H), 1.4 (d, 3H).

a.2 4-((R)-2-Fluoro-1-methyl-ethyl)-benzenesulfonyl chloride a.2.1 Toluene-4-sulfonic acid (R)-2-phenyl-propyl ester

Following the procedure analogous to that used for the synthesis of toluene 4-sulfonic acid (S)-2-phenyl-propyl ester, but using (R)-2-phenyl-1-propanol, the title compound was prepared a.2.2 ((R)-2-Fluoro-1-methyl-ethyl)-benzene

The title compound was prepared as described above for the synthesis of ((S)-2-fluoro-1-methyl-ethyl)-benzene, but using toluene-4-sulfonic acid (R)-2-phenyl-propyl ester instead of toluene-4-sulfonic acid (S)-2-phenyl-propyl ester.

$^1$H-NMR (CDCl$_3$, 400 MHz): δ [ppm] 7.2-7.4 (m, 5H), 4.3-4.6 (several m, 2H), 3.15 (m, 1H).1.3 (m, 3H).

a.2.3 4-((R)-2-Fluoro-1-methyl-ethyl)-benzenesulfonyl chloride 1.3 g of ((R)-2-fluoro-1-methyl-ethyl)-benzene (9.4 mmol) were dissolved in 50 ml of dichloromethane. At 0-5° C., 1.1 g of chlorosulfonic acid (9.4 mmol), dissolved in 10 ml of dichloromethane, were added dropwise. The reaction mixture was stirred for 20 min at 0-5° C. and then added to a solution of 2.15 g of phosphorous pentachloride dissolved in 40 ml of dichloromethane. The reaction mixture was stirred for 30 min at 0-5° C. and 1 h at room temperature. The solvent was evaporated, 100 ml of diethyl ether were added, the mixture was washed once with 150 ml of water, and the organic layer dried over magnesium sulfate, filtered, and the solvent evaporated under reduced pressure. The crude product was purified via silica gel chromatography with n-heptane-dichloromethane (1:1) as eluent to give 0.261 g of the title compound.

$^1$H-NMR (CDCl$_3$, 400 MHz): δ [ppm] 8.0 (d, 2H), 7.5 (d, 2H), 4.5 (dd, 2H), 3.25 (m, 1H), 1.4 (d, 3H).

a.3 4-(2-Fluoro-1-methyl-ethyl)-benzenesulfonyl chloride

Following the procedures analogous to that used for the preparation of 4-((S)-2-fluoro-1-methyl-ethyl)-benzenesulfonyl chloride, but starting with 2-phenyl-1-propanol in step a.3.1, the title compound was prepared.

$^1$H-NMR (CDCl$_3$, 400 MHz): δ [ppm] 8.0 (d, 2H), 7.5 (d, 2H), 4.5 (dd, 2H), 3.25 (m, 1H), 1.4 (d, 3H).

a.4 4-(2-Fluoro-1-fluoromethyl-ethyl)-benzenesulfonyl chloride a.4.1 (2-Fluoro-1-fluoromethyl-ethyl)-benzene 4 g of 3-phenylglutaric acid (19.21 mmol) were suspended in 350 ml of dichloromethane. At room temperature, 6.5 g of xenon difluoride (38.42 mmol) were added and the reaction mixture was stirred at room temperature for 18 h. The organic phase was washed once with 975 ml of 6% aqueous sodium hydrogencarbonate, dried over magnesium sulfate, filtered, and the solvent evaporated. The remaining residue was distilled at a bath temperature of 123° C. at 21 mm to yield 0.78 g of the title compound that contained ~50% of 4-(2-Fluoro-1-methyl-ethyl)-benzene.

$^1$H-NMR (CDCl$_3$, 400 MHz): δ [ppm] 7.2-7.4 (m, 5H), 4.6-4.8 (dd, 4H), 3.3 (m, 1H).

a.4.2 4-(2-Fluoro-1-fluoromethyl-ethyl)benzenesulfonyl chloride

Following the procedures analogous to that used for the preparation of 4-((S)-2-fluoro-1-methyl-ethyl)-benzenesulfonyl chloride, but using 5 equivalents. of chlorosulfonic acid, 0.12 g of the title compound were obtained.

$^1$H-NMR (CDCl$_3$, 400 MHz): δ [ppm] 8.05 (d, 2H), 7.55 (d, 2H), 4.75 (dd, 4H), 3.4 (m, 1H).

a.5 4-(3,3,3-Trifluoropropyl)-benzenesulfonyl chloride 2.9 g were obtained from commercially available (3,3,3-trifluoropropyl)-benzene following the procedure used for the synthesis of 4-((S)-2-fluoro-1-methyl-ethyl)-benzenesulfonyl chloride described above.

$^1$H-NMR (CDCl$_3$, 400 MHz): δ [ppm] 8.0 (d, 2H), 7.45 (d, 2H), 3.0 (t, 2H), 2.45 (m, 2H).

a.6 4-(2,2,2-Trifluoroethyl)-benzenesulfonyl chloride

The product was obtained from commercially available (2,2,2-trifluoroethyl)-benzene following the procedure as described in J. Org. Chem., 1960, 25, 1824-26.

$^1$H-NMR (CDCl$_3$, 400 MHz): δ [ppm] 8.05 (d, 2H), 7.55 (d, 2H), 3.5 (q, 2H).

a.7 4-(3-Fluoropropyl)-benzenesulfonyl chloride a.7.1 (3-Fluoropropyl)-benzene 15.6 g of diethylaminosulfurtrifluoride (DAST, 96.91 mmol) were dissolved in 18 ml of dichloromethane. At 0-5°

C., 12 g of 3-phenyl-1-propanol (88.1 mmol) dissolved in 30 ml of dichloromethane, were added dropwise. The reaction mixture was stirred for 18 h, and, after addition of 30 ml of dichloromethane, poured onto 100 ml of ice water. The organic layer was separated, dried over magnesium sulfate, filtered, and the solvent evaporated. The crude product was purified by distillation at a bath temperature of 106° C. at 20 mm to yield 7.4 g of the title compound.

$^1$H-NMR (CDCl$_3$, 400 MHz): δ [ppm] 7.1-7.3 (m, 5H), 4.4 (dt, 2H), 2.7 (m, 2H).2.0 (m, 2H).

a.7.2 4-(3-Fluoropropyl)-benzenesulfonyl chloride 4.1 g of (3-fluoro-propyl)-benzene (29.67 mmol) were dissolved in 40 ml of dichloromethane. At 0-5° C., 6.91 g of chlorosulfonic acid (59.34 mmol), dissolved in 10 ml of dichloromethane, were added dropwise. The reaction mixture was stirred for 45 min at 0-5° C. and then added to a solution of 6.8 g of phosphorous pentachloride (32.63 mmol) dissolved in 50 ml of dichloromethane. The reaction mixture was stirred for 1 h at 5-10° C. The solvent was evaporated, 150 ml of diethyl ether added, washed once with 150 ml of ice water, and the organic layer dried over magnesium sulfate, filtered, and the solvent evaporated under reduced pressure. The crude product was purified via silica gel chromatography with n-heptane-dichloromethane (11:9) as eluent to give 5.5 g of the title compound.

$^1$H-NMR (CDCl$_3$, 400 MHz): δ [ppm] 7.95 (d, 2H), 7.45 (d, 2H), 4.5 (dt, 2H), 2.9 (t, 2H), 2.05 (m, 2H).

a.8 4-(2,2-Difluoro-cyclopropyl)-benzenesulfonyl chloride 2.07 g of were obtained from commercially available (2,2-difluorocyclopropyl)-benzene following the procedure used for the synthesis of (3-fluoropropyl)-benzenesulfonyl chloride with the exception that only 1.1 equivalents of phosphorous pentachloride were used.

$^1$H-NMR (CDCl$_3$, 400 MHz): δ [ppm] 8.0 (d, 2H), 7.45 (d, 2H), 2.85 (m, 1H), 2.0 (m, 1H), 1.75 (m, 1H).

a.9 3-Bromo-4-trifluoromethoxy-benzenesulfonyl chloride 2.0 g of 1-bromo-2-(trifluoro-methoxy)benzene (8.3 mmol) were dissolved in 30 ml of dichloromethane. At 0-5° C., 1.06 g of chlorosulfonic acid (9.13 mmol), dissolved in 3 ml of dichloromethane, were added dropwise. The reaction mixture was stirred for 30 min at room temperature. Additional 5.5 equivalents of chlorosulfonic in dichloromethane were added to drive the reaction to completion. Standard work-up was followed and silica gel chromatography with n-heptane-dichloromethane (6:4) as eluent gave 2.19 g of the title compound.

$^1$H-NMR (CDCl$_3$, 400 MHz): δ [ppm] 8.3 (d, 1H), 8.05 (dd, 1H), 7.5 (dd, 1H).

a.10 4-(2-Fluoroethyl)-benzenesulfonyl chloride a.10.1 (2-Fluoroethyl)-benzene 6.8 g of the title compound were obtained from commercially available 2-phenylethanol following the procedure used for the synthesis of (3-fluoropropyl)-benzene.

$^1$H-NMR (CDCl$_3$, 400 MHz): δ [ppm] 7.1-7.3 (m, 5H), 4.6 (m, 1H), 4.45 (m, 1H), 2.95 (m, 1H), 2.9 (m, 1H).

a.10.2 4-(2-Fluoroethyl)-benzenesulfonyl chloride 3.55 g were obtained following the procedure used for the synthesis of 4-(R)-2-fluoro-1-methyl-ethylybenzenesulfonyl chloride.

$^1$H-NMR (CDCl$_3$, 400 MHz): δ [ppm] 8.0 (d, 2H), 7.5 (d, 2H), 4.7 (dt, 2H), 3.05-3.2 (dt, 2H).

a.11 5-Propylthiophene-2-sulfonyl chloride

Following the procedures analogous to that used for the preparation of (3-fluoro-propyl)-benzenesulfonyl chloride, but using only 1 equivalent of phosphorous pentachloride, the title compound was prepared.

$^1$H-NMR (CDCl$_3$, 400 MHz): δ [ppm] 7.7 (d, 1H), 6.85 (d, 1H), 2.9 (t, 2H), 1.75 (m, 2H), 1.0 (t, 3H).

a.12 4-(1-Methyl-1H-pyrazol-4-yl)-benzenesulfonyl chloride a.12.1 1-Methyl-4-phenyl-1H-pyrazole 1 g of 2-phenylmalonaldehyde (6.75 mmol) were dissolved in 25 ml of ethanol. 0.36 ml of N-methyl-hydrazine (6.75 mmol) were added, the reaction mixture was stirred under reflux for 4 h, the solvent evaporated under reduced pressure to yield 1.09 g of the product.

ESI-MS: 159.1 [M+H]+

$^1$H-NMR (CDCl$_3$, 400 MHz): δ [ppm] 7.75 (s, 1H), 7.6 (s, 1H), 7.45 (d, 2H), 7.35 (t, 2H), 7.2 (t, 1H), 3.9 (s, 3H)

a.12.2 4-(1-Methyl-1H-pyrazol-4-yl)-benzenesulfonyl chloride 0.5 g of 1-methyl-4-phenyl-1H-pyrazole (3.16 mmol) were dissolved in 20 ml of dichloromethane. At 0° C., 0.232 ml of chlorosulfonic acid were added and the reaction mixture was stirred for 1 h under ice cooling. Additional 0.7 ml of chlorosulfonic acid were added, the mixture was stirred at 0° C. for 30 minutes and then 90 minutes at 50° C. The two phases were separated and the lower layer put on ice, extracted twice with diethyl ether, dried over magnesium sulfate, filtered, and the solvent evaporated under reduced pressure to yield 0.496 g of the product.

$^1$H-NMR (CDCl$_3$, 400 MHz): δ [ppm] 8.0 (d, 2H), 7.85 (s, 1H), 7.75 (s, 1H), 7.65 (d, 2H), 4.0 (s, 3H).

a.13 4-(1,1,1-Trifluoropropan-2-yl)benzenesulfonyl chloride and 2-(1,1,1-trifluoropropan-2-yl)benzenesulfonyl chloride Prepared on a 14 g scale following the procedure outlined in Scheme 7. 2-(1,1,1-Trifluoropropan-2-yl)benzenesulfonyl chloride is a by-product of the reaction.

4-(1,1,1-Trifluoropropan-2-yl)benzenesulfonyl chloride:
MS (ESI) m/z: 273.1 [M+H]$^+$
$^1$H-NMR (DMSO-d$_6$): δ [ppm] 7.62 (d, 2H), 7.33 (d, 2H), 3.81 (m, 1H), 1.42 (d, 3H).

2-(1,1,1-Trifluoropropan-2-yl)benzenesulfonyl chloride:
MS (ESI) m/z: 273.1 [M+H]$^+$ a.14 4-(1,1-Difluoropropan-2-yl)benzenesulfonyl chloride and 2-(1,1-Difluoropropan-2-yl)benzene-1-sulfonyl chloride Prepared on an 11 g scale following the procedure outlined in Scheme 6. 2-(1,1-Difluoropropan-2-yl)benzene-1-sulfonyl chloride is a by-product of the reaction.

4-(1,1-Difluoropropan-2-yl)benzenesulfonyl chloride:
MS (ESI) m/z: 255.0 [M+H]+
$^1$H-NMR (DMSO-d$_6$): δ [ppm] 8.03 (d, 2H), 7.55 (d, 2H), 5.88 (dt, 1H), 3.34 (m, 1H), 1.47 (d, 3H).
$^{13}$C-NMR (DMSO-d$_6$): δ [ppm] 146.43, 143.54, 129.77, 127.28, 117.06 (t), 43.76, 13.78.

2-(1,1-difluoropropan-2-yl)benzene-1-sulfonyl chloride:
Isolated by chromatography on 110 mg scale.
MS (ESI) m/z: 255.0 [M+H]+
$^1$H-NMR (DMSO-d$_6$): δ [ppm] 8.15 (d, 1H), 7.77 (t, 1H), 7.70 (d, 1H), 7.54 (t, 1H), 5.99 (dt, 1H), 4.43 (m, 1H), 1.51 (d, 3H).
$^{13}$C-NMR (DMSO-d$_6$): δ [ppm] 143.45, 138.63, 135.53, 130.93, 129.04, 128.17, 116.61 (t), 38.38, 13.68.

II. Preparation of Compounds I

Example 1

4-Isopropyl-N-(2-propylaminomethyl-1H-indol-5-yl)-benzenesulfonamide 1.1 5-Nitro-1H-indole-2-carboxylic acid To a solution of ethyl-5-nitro-1H-indole-2-carboxylate (22.7 g, 96.83 mg) in ethanol (EtOH) (150 ml) sodium hydroxide (11.62 g, 290.5 mmol) was added. The mixture was stirred at room temperature for 16 h. During this time a brown solid formed. After evaporation of the solvent under reduced pressure the residue was suspended in water and HCl was added. The color of the precipitate changed from brown to yellow. After filtration the residue was washed with water and dried in a vacuum oven at 50° C. to give the product as a brown powder (19.53 g, 98%).

1.2 5-Nitro-1H-indole-2-carboxylic acid propylamide

To a solution of 5-nitro-1H-indole-2-carboxylic acid (6.95 g, 33.7 mmol) in N,N-dimethylformamide (DMF)/pyridine (1/1, 150 ml) N,N'-carbonyl-diimidazole (5.47 g, 33.71 mmol) was added. The mixture was stirred at 80° C. for 1 h. At 0° C. propylamine (9.96 g, 168.56 mmol) was added. The mixture was stirred at 0° C. for 1 h and then at room temperature for 16 h. The solution was diluted with water (2 l). After addition of sodium chloride the product precipitated. After filtration the residue was washed with water and pentane, and dried in a vacuum oven at 50° C. to give the product as a yellow powder.
MS (ESI) m/z: 248.05 [M+H]+

1.3 5-Amino-1H-indole-2-carboxylic acid propylamide

To a solution of 5-nitro-1H-indole-2-carboxylic acid propylamide (2.94 g, 11.9 mmol) in EtOH (150 ml) a suspension of palladium on charcoal (10%, 1 g) in EtOH was added. The mixture was hydrogenated at atmospheric pressure. After filtration and removal of the solvents in vacuo the product was obtained as a yellow powder (2.46 mg, 95%).
MS (ESI) m/z: 218.15 [M+H]+

1.4 5-(4-Isopropyl-benzenesulfonylamino)-1H-indole-2-carboxylic acid propylamide To a solution of 5-amino-1H-indole-2-carboxylic acid propylamide (500 mg, 2.3 mmol) in pyridine (20 ml) 4-isopropyl-benzenesulfonyl chloride (500 mg, 2.3 mmol) was added. The mixture was stirred at room temperature for 16 h. After evaporation of the solvent the residue was partitioned between ethyl acetate and saturated aqueous NaHCO$_3$. The organic layer was separated, washed with saturated aqueous NaHCO$_3$ and dried over MgSO$_4$. The filtered solution was evaporated to give the product as a yellow powder (910 mg, 98.8%).
MS (ESI) m/z: 400.01 [M+H]+

1.5 4-Isopropyl-N-(2-propylaminomethyl-1H-indol-5-yl)-benzenesulfonamide

To a suspension of lithium aluminiumhydride (590 mg, 15.54 mmol) in tetrahydrofuran (THF) (40 ml, dried over Al$_2$O$_3$) at −5 to 0° C. a solution of 5-(4-isopropyl-benzenesulfonylamino)-1H-indole-2-carboxylic acid propylamide (1.03 g, 2.59 mmol) in THF (10 ml) was added. After complete addition the mixture was allowed to warm to room temperature and was heated to reflux for 3 h. At 0° C. THF and then water were added. The mixture was dried with Na$_2$SO$_4$. The filtered solution was evaporated and the residue was purified by column chromatography (toluene:THF:methanol, 4:1:1+2.5% triethylamine) to give the product as a yellow powder (240 mg, 24%).
MS (ESI) m/z: 386.1 [M+H]+
$^1$H-NMR (DMSO-d$_6$): δ [ppm] 10.95 (bs, 1H), 7.60 (d, 2H), 7.35 (d, 2H), 7.07-7.20 (m, 2H), 6.75-6.79 (m, 1H), 6.18 (s, 1H), 3.79 (s, 2H), 2.85-2.96 (m, 1H), 2.40-2.55 (m, 2H), 1.39-1.49 (m, 2H), 1.10-1.20 (m, 6H), 0.85 (t, 3H).

Example 2

4-Isopropyl-N-(2-propylaminomethyl-2,3-dihydro-1H-indol-5-yl)-benzenesulfonamide×HCl To 4-isopropyl-N-(2-propylaminomethyl-1H-indol-5-yl)-benzenesulfonamide (110 mg, 0.27 mmol) trifluoroacetic acid (TFA) (5 ml) was added at 0° C. followed by adding sodium borohydride pellets (50 mg, 1.36 mmol). The temperature during addition was kept below 10° C. After complete addition the mixture was stirred for 2 h at 0° C. The mixture carefully was added to an ice cold saturated aqueous solution of NaHCO$_3$. The aqueous layer was extracted three times with dichloromethane. The combined organic layers were dried over MgSO$_4$, filtered and the solvent evaporated under reduced pressure. To a solution of the residue in ethyl acetate/diethyl ether a solution of HCl in diethyl ether (1M) was added. The resulting precipitate was collected and dried in vacuo at 30° C. to give the product as purple crystals (60 mg, 51%).
MS (ESI) m/z: 388.15 [M+H]+
$^1$H-NMR (DMSO-d$_6$): δ [ppm] 9.61 (bs, 1H), 8.85 (bs, 2H), 7.60 (d, 2H), 7.48 (d, 2H), 6.80 (s, 1H), 6.65 (d, 1H), 6.40 (d, 1H), 4.03-4.15 (m, 1H), 2.80-3.10 (m, 6H), 2.65-2.75 (m, 1H), 1.60-1.70 (m, 2H), 1.15-1.20 (m, 6H), 0.90 (t, 3H).

Example 3

N-(2-Propylaminomethyl-1H-indol-5-yl)-4-trifluoromethoxy-benzenesulfonamide×½ fumaric acid 3.1 5-(4-Trifluoromethoxy-benzenesulfonylamino)-1H-indole-2-carboxylic acid propylamide To a solution of 5-amino-1H-indole-2-carboxylic acid propylamide (500 mg, 2.3 mmol) in pyridine (20 ml) 4-trifluoromethoxy-benzenesulfonyl chloride (600 mg, 2.3 mmol) was added. The mixture was stirred at room temperature for 16 h. After evaporation of the solvent the residue was partitioned between ethyl acetate and saturated aqueous. The organic layer was separated, washed with saturated aqueous NaHCO$_3$ and dried over MgSO$_4$. The filtered solution was evaporated to give the product as a yellow powder (1.01 g, 99%).

MS (ESI) m/z: 442.0 [M+H]$^+$

3.2 N-(2-Propylaminomethyl-indol-5-yl)-4-trifluoromethoxy-benzenesulfonamide×½ fumaric acid To a suspension of lithium aluminiumhydride (500 mg, 13.18 mmol) in THF (40 ml, dried over Al$_2$O$_3$) at −5-0° C. a solution of 5-(4-trifluoromethoxy-benzenesulfonylamino)-1H-indol-2-carboxylic acid propylamide (970 mg, 2.20 mmol) in THF (10 ml) was added. After complete addition the mixture was allowed to warm to room temperature and was heated to reflux for 3 h. At 0° C. THF and then water were added. The mixture was dried with Na$_2$SO$_4$. The filtered solution was evaporated in vacuo and the residue was purified by column chromatography (toluene:THF:methanol, 4:1:1, +2.5% triethylamine). To a solution of the obtained oil in isopropanol fumaric acid (254 mg, 2.19 mmol) was added. The precipitate was recrystallized from ethanol to give the product as a yellow powder (220 mg, 18%).

MS (ESI) m/z: 428.0 [M+H]$^+$ $^1$H-NMR (DMSO-d$_6$): δ [ppm] 7.78 (d, 2H), 7.47 (d, 2H), 7.10-7.20 (m, 2H), 6.70-6.80 (m, 1H), 6.55 (s, 1H), 6.23 (s, 1H), 3.89 (s, 2H), 2.53-2.60 (m, 2H), 1.45-1.55 (m, 2H), 0.86 (t, 3H).

Example 4

N-(2-Propylaminomethyl-2,3-dihydro-1H-indol-5-yl)-4-trifluoromethoxy-benzenesulfonamide×HCl A solution of 5-(4-trifluoromethoxy-benzenesulfonylamino)-1H-indol-2-carboxylic acid propylamide (960 mg, 2.18 mmol) in THF (25 ml) was heated to reflux and a solution of borane-dimethylsulfide complex (2M in THF, 19.6 mmol) was added. The mixture was heated to reflux for 10 h. At room temperature the mixture was adjusted to pH=1 by adding a solution of HCl in ethanol and stirred for 15 min. After evaporation of the solvents the residue was partitioned between ethyl acetate and HCl (2M). To the separated aqueous layer aqueous ammonia was added (pH=9). After extraction with dichloromethane the organic layer was dried over MgSO$_4$ and evaporated. To a solution of the residue in diethyl ether HCl in diethyl ether (1M) was added. The resulting precipitate was collected, washed with diethyl ether and dried in vacuo at 30° C. to give the product as a yellow powder (160 mg, 16%).

MS (ESI) m/z: 430.15 [M+H]$^+$ $^1$H-NMR (DMSO-d$_6$): δ [ppm] 9.90 (s, 1H), 9.05 (bs, 2H), 7.62 (d, 2H), 7.55 (d, 2H), 6.81 (s, 1H), 6.68 (d, 1H), 6.49 (d, 1H), 4.10-4.20 (m, 1H), 2.70-3.15 (m, 6H), 1.60-1.70 (m, 2H), 0.91 (t, 3H).

Example 5

4-Isopropyl-N-(5-propylaminomethyl-5,6,7,8-tetrahydro-naphthalen-2-yl)-benzenesulfonamide×HCl

5.1 5-Aminomethyl-5,6,7,8-tetrahydro-naphthalen-2-ylamine×2 HCl

5-Aminomethyl-5,6,7,8-tetrahydro-naphthalen-2-ylamine×2 HCl was synthesized according to a synthetic protocol described in EP325963 starting from commercially available N-(5-oxo-5,6,7,8-tetrahydro-naphthalen-2-yl)-acetamide.

5.2 N-(6-Amino-1,2,3,4-tetrahydro-naphthalen-1-ylmethyl)-propionamide

A solution of 5-aminomethyl-5,6,7,8-tetrahydro-naphthalen-2-ylamine×2 HCl (500 mg, 2.01 mmol) in water (90 ml) was adjusted to pH=11.25 by adding aqueous NaOH (0.5M). Then propionic acid anhydride (290 mg, 2.21 mmol) was added slowly while maintaining the pH in a range from 11.2 to 11.3 by simultaneously adding aqueous NaOH (0.5M). After complete addition the mixture was adjusted to pH=2.5 with aqueous HCl (1N) and evaporated under reduced pressure. The residue was dissolved in water, and washed twice with ethyl acetate. After addition of aqueous ammonia the aqueous layer was extracted three times with dichloromethane. The combined dichloromethane layers were dried over MgSO$_4$, and evaporated under reduced pressure to give the product as a yellow resin (320 mg, 68%).

MS (ESI) m/z: 233.15 [M+H]$^+$

5.3 N-[6-(4-Isopropyl-benzenesulfonylamino)-1,2,3,4-tetrahydro-naphthalen-1-ylmethyl]-propionamide To a solution of N-(6-amino-1,2,3,4-tetrahydro-naphthalen-1-ylmethyl)-propionamide (290 mg, 1.26 mmol) in pyridine (10 ml) at 0° C. 4-isopropyl-benzenesulfonyl chloride (280 mg, 1.26 mmol) was added. The mixture was stirred at 0° C. for 1 h and 16 h at room temperature. After evaporation under reduced pressure the obtained residue was partitioned between ethyl acetate and saturated aqueous NaHCO$_3$. The organic layer was washed twice with saturated aqueous NaHCO$_3$, dried over MgSO$_4$, filtered and the solvent evaporated under reduced pressure to give the product as a brown resin (530 mg, 100%).

MS (ESI) m/z: 415.15 [M+H]$^+$

5.4 4-Isopropyl-N-(5-propylaminomethyl-5,6,7,8-tetrahydro-naphthalen-2-yl)-benzenesulfonamide× HCl To a solution of N-[6-(4-isopropyl-benzenesulfonylamino)-1,2,3,4-tetrahydro-naphthalen-1-ylmethyl]-propionamide (510 mg, 1.23 mmol) in THF (20 ml) borane-dimethylsulfide complex (2M in THF, 3.06 mmol) was added. The mixture was heated to reflux for 2 h. At room temperature HCl in ethanol (2M) was added and the mixture was stirred for 30 min. After evaporation under reduced pressure the residue was triturated with diethyl ether. After filtration the residue was washed with diethyl ether and dried in vacuo to give the product as yellow crystals (490 mg, 92%).

MS (ESI) m/z: 401.15 [M+H]$^+$ $^1$H-NMR (DMSO-d$_6$): δ [ppm] 10.21 (s, 1H), 8.80 (bs, 1H), 8.60 (bs, 1H), 7.71 (d, 2H), 7.45 (d, 2H), 7.15 (d, 1H), 6.93 (d, 1H), 6.82 (s, 1H), 2.80-3.20 (m, 6H), 2.52-2.61 (m, 2H), 1.55-1.90 (m, 6H), 1.15-1.29 (m, 6H), 0.90 (t, 3H).

Example 6

4-Isopropyl-N-(2-propylaminomethyl-1H-benzoimidazol-5-yl)-benzenesulfonamide

6.1 N-(4-Amino-3-nitro-phenyl)-4-isopropyl-benzenesulfonamide

To a mixture of 2-nitro-benzene-1,4-diamine (10 g, 65.30 mmol) and N,N-dimethylaniline (8.7 g, 71.83 mmol) in acetonitrile (310 ml) at 0° C. 4-isopropyl-benzenesulfonyl-chloride (13.85 g, 63.34 mmol) was added over a period of 1 h. The mixture was stirred at 0° C. for 1 h and for 16 h at room temperature. After concentrating the mixture in vacuo the obtained oil was triturated with water. The precipitate was collected, washed with ethanol and dried in vacuo to give the product as a yellow powder (11.76 g, 54%).

6.2 N-(3,4-Diamino-phenyl)-4-isopropyl-benzene-sulfonamide×HCl

A mixture of N-(4-amino-3-nitro-phenyl)-4-isopropyl-benzenesulfonamide (5 g, 14.91 mmol) and palladium on charcoal (10%, 500 mg) in ethanol (100 ml) was hydrogenated at atmospheric pressure. After filtration the mixture was concentrated in vacuo. The brown oil was dissolved in dichloromethane and a solution of HCl in isopropanol was added. The precipitate was collected and dried in vacuo to give the product as a brown powder (4.9 g, 87%).

6.3 N-[5-(4-Isopropyl-benzenesulfonylamino)-1H-benzoimidazol-2-ylmethyl]-propionamide To a solution of N-(3,4-diamino-phenyl)-4-isopropyl-benzenesulfonamide×HCl (500 mg, 1.32 mmol) in DMF (20 ml) at 0° C. was added propionylamino-acetic acid (170 mg, 1.32 mmol) and 1-hydroxy-7-azabenzotriazole (HOAt) (220 mg, 1.59 mmol). After stirring the mixture at 0° C. for 15 min EDC (N-ethyl-N'-(3-dimethylaminopropyl)-carbodiimide) (300 mg, 1.45 mmol) was added. DIPEA (diisopropylethylamine) (0.92 ml, 5.29 mmol) was added after stirring another 15 min at 0° C. The mixture was stirred at room temperature for 16 h, and then concentrated under reduced pressure. The residue was partitioned between ethyl acetate and saturated aqueous NaHCO$_3$ and the organic layer was dried over MgSO$_4$, filtered, and the solvent evaporated under reduced pressure. A solution of the obtained oil in acetic acid was heated to 70° C. for 6 h. After evaporation of the solvent in vacuo the residue was purified by column chromatography to give the product as a yellow oil (320 mg, 61%).

6.4 4-Isopropyl-N-(2-propylaminomethyl-1H-benzoimidazol-5-yl)-benzenesulfonamide To a suspension of lithium-aluminiumhydride (180 mg, 4.79 mmol) in THF (5 ml, dried Al$_2$O$_3$) at −5-0° C. a solution of N-[5-(4-isopropyl-benzenesulfonylamino)-1H-benzoimidazol-2-ylmethyl]-propionamide (320 mg, 0.80 mmol) in THF (5 ml) was added. After complete addition the mixture was allowed to warm to room temperature and was heated to reflux for 2 h. At 0° C. THF and then water were added. The mixture was dried with Na$_2$SO$_4$. The filtered solution was evaporated in vacuo and the residue was purified by preparative HPLC (water/5% acetonitrile/0.1% acetic acid) to give the product as a yellow oil (10 mg, 3%).

MS (ESI) m/z: 387.25 [M+H]$^+$
$^1$H-NMR (CDCl$_3$): δ [ppm] 7.62 (d, 2H), 7.55-7.65 (m, 2H), 7.75 (s, 1H), 7.46 (d, 2H), 7.61 (d, 1H), 4.08 (s, 2H), 2.85-2.91 (m, 1H), 2.62-2.70 (m, 2H), 1.48-1.56 (m, 2H), 1.18-1.22 (m, 6H), 0.91 (t, 3H).

Example 7

4-Isopropyl-N-(2-propylaminomethyl-indan-5-yl)-benzenesulfonamide

7.1 Methanesulfonic acid indan-2-yl ester

2-Indanol (20.00 g, 149.5 mmol) and diisopropylethylamine (21.2 g, 164 mmol) was stirred in dichloromethane (300 mL) at 0° C. Methanesulfonyl chloride (18.78 g, 164 mmol) and dimethylaminopyridine (1.80 g) were added simultaneously and stirring continued at room temperature for 18 h. Solution was evaporated, partitioned between ethyl acetate and water, and the organic phase separated. This was washed with NaHCO$_3$ (sat) and with citric acid solution (5%) and dried over MgSO$_4$. The filtered solution was concentrated and the resultant solid recrystallized from isopropanol-EtOH (3:1) to give off-white crystals (24.6 g, 78%).

MS (ESI) m/z: 230.1 [M+H]$^+$
$^1$H-NMR (DMSO-d$_6$): δ [ppm] 7.28 (m, 2H), 7.18 (m, 2H), 5.46 (m, 1H), 3.34 (m, 2H), 3.15 (m, 2H).
$^{13}$C-NMR (DMSO-d$_6$): δ [ppm] 139.5 (s), 126.8 (d), 124.5 (d), 82.7 (d), 37.6 (t).

7.2 Indan-2-carbonitrile

A mixture of methanesulfonic acid indan-2-yl ester (18.65 g, 87.9 mmol) and tetraethylammonium cyanide (15.10 g) in acetonitrile (180 mL) was heated to 55° C. for 5 hours, cooled and concentrated. The residue was partitioned between ethyl acetate and water, and the organic phase separated. This was dried over MgSO$_4$ and the filtered solution was concentrated and then separated by column chromatography (dichloromethane:ethyl acetate, 6:1-1:1) to give the product as a red solid (6.51 g, 52%).

MS (ESI) m/z: 144.1 [M+H]$^+$
$^1$H-NMR (DMSO-d$_6$): δ [ppm] 7.28 (m, 2H), 7.18 (m, 2H), 3.52 (m, 1H), 3.31 (m, 2H), 3.17 (m, 2H).

7.3 Indan-2-yl-methylamine

The indan-2-carbonitrile (1.60 g, 11.2 mmol) was dissolved in diethyl ether (50 mL) and LiAlH$_4$ (0.43 g, 11.3 mmol) added in portions at 0° C. and the solution stirred for a further 3 h at 5° C. The reaction was quenched by the sequential addition of water, NaOH solution (10%) and water. The organic phase was separated, dried (MgSO$_4$), filtered and concentrated to give the title compound as a light brown oil (1.30 g, 79%).

MS (ESI) m/z: 148.1 [M+H]$^+$
$^1$H-NMR (DMSO-d$_6$): δ [ppm] 7.18 (m, 2H), 7.06 (m, 2H), 3.35 (m, 1H), 2.90 (m, 2H), 2.52 (m, 3H), 2.35 (m, 1H), 1.40 (br s, 1H).

7.4 N-Indan-2-ylmethyl-propionamide

A solution of indan-2-yl-methylamine (5.55 g, 37.7 mmol) and triethylamine (5.67 g, 56.0 mmol) in 100 mL THF was stirred at 5° C. and propionic anhydride (5.15 g, 39.6 mmol) added dropwise. After the mixture was stirred for 18 h at room temperature, the solvent was removed and ethyl acetate/water were added. The organic layer was washed with water and dried over MgSO$_4$. The filtrate was concentrated to give a brown oil (8.79 g, 97%).

MS (ESI) m/z: 204.1 [M+H]$^+$

7.5 N-(5-Nitro-indan-2-ylmethyl)-propionamide

N-Indan-2-ylmethyl-propionamide (4.00 g, 19.7 mmol) was dissolved in nitromethane (60 mL) and added to a mixture of concentrated H$_2$SO$_4$ (19 mL), concentrated nitric acid (1.4 mL) and water (3.2 mL) cooled to 5° C. After stirring for 45 min, the reaction solution was poured into water, extracted with ethyl acetate and the organic phase separated and dried over MgSO$_4$. The filtered solution was concentrated to give a brown oil (4.67 g, 96%).

MS (ESI) m/z: 249.1 [M+H]$^+$

7.6 N-(5-Amino-indan-2-ylmethyl)-propionamide

The mixture of nitro compounds (4.67 g, 18.8 mmol) was dissolved in methanol (MeOH)(250 mL) and tin chloride (12.7 g, 56.3 mmol) added. The solution was heated to reflux for 3 h and then a second portion of tin chloride was added and reflux continued for a further 3 h. The solution was concentrated and the residue was partitioned between ethyl acetate and NaOH (2M), and the organic phase separated and dried over $MgSO_4$. The filtered solution was concentrated and the residue separated by preparative HPLC (20-90% MeOH) to give the 2 amino isomers. The product was obtained as a yellow oil (0.97 g, 24%).

MS (ESI) m/z: 219.1 [M+H]$^+$ $^1$H-NMR (DMSO-d$_6$): δ [ppm] 7.75 (m, 1H), 6.76 (d, 2H), 6.37 (s, 1H), 6.31 (d, 1H), 3.08 (m, 2H), 2.42 (m, 2H), 2.07 (m, 2H), 0.97 (t, 3H).

7.7 N-[5-(4-Isopropyl-benzenesulfonylamino)-indan-2-ylmethyl]-propionamide

N-(5-Amino-indan-2-ylmethyl)-propionamide (0.93 g, 4.26 mmol) was dissolved in pyridine-dichloromethane (1:2, 60 mL) and cooled to 5° C. 4-Isopropylbenzenesulfonyl chloride (0.98 g, 4.48 mmol) was added and the solution stirred at 5° C. for 3 h. Solution was evaporated, partitioned between ethyl acetate and water, and the organic phase separated and dried over $MgSO_4$. The filtered solution was concentrated to give the product as a brown oil (1.69 g, 99%).

MS (ESI) m/z: 401.1 [M+H]$^+$

7.8 4-Isopropyl-N-(2-propylaminomethyl-indan-5-yl)-benzenesulfonamide

N-[5-(4-Isopropyl-benzenesulfonylamino)-indan-2-ylmethyl]propionamide (0.50 g, 1.25 mmol) was dissolved in 10 mL of THF and 4.2 mL (43.9 mmol) of a borane-THF complex was introduced dropwise. The resulting mixture was stirred at reflux for 1 h. The solution was cooled, 5 mL of 2 N HCl was added slowly, and the mixture was stirred at reflux for 2 h. The cooled solution was quenched with water, then NaOH (2N) and extracted with ethyl acetate. The organic phase was dried over $MgSO_4$, filtered, and the filtrate was evaporated in vacuo to give product as a white solid which was further purified by column chromatography using (dichloromethane-MeOH, 7-12%) to give an oil. The oil was dissolved in ethyl acetate and HCl (4M, dioxane) was added to give the product as a white solid (40 mg, 7%).

MS (ESI) m/z: 387.2 [M+H]$^+$ $^1$H-NMR (DMSO-d$_6$): δ [ppm] 7.69 (d, 2H), 7.40 (d, 2H), 7.03 (d, 1H), 6.94 (s, 1H), 6.84 (d, 1H), 2.90 (m, 3H), 2.81 (d, 2H), 2.70-2.55 (m, 5H), 1.55 (m, 2H), 0.85 (t, 3H).

$^{13}$C-NMR (DMSO-d$_6$): δ [ppm] 153.4 (s), 143.2 (s), 137.9 (s), 137.3 (s), 136.1 (s), 127.1 (d), 126.7 (d), 124.7 (d) 118.4 (d), 116.5 (d), 51.9 (t), 49.6 (t), 37.4 (d), 36.0 (t), 33.2 (d), 23.3 (q), 20.0 (t), 11.2 (q).

Example 8

4-Isopropyl-N-(2-propylaminomethyl-indan-4-yl)-benzenesulfonamide

8.1 N-(4-Nitro-indan-2-ylmethyl)-propionamide

The title compound was prepared in an analogous manner as described above.

MS (ESI) m/z: 249.1 [M+H]$^+$

8.2 N-(4-Amino-indan-2-ylmethyl)-propionamide

The title compound was prepared in an analogous manner as described above. (0.55 g, 14%).

MS (ESI) m/z: 219.1 [M+H]$^+$ $^1$H-NMR (DMSO-d$_6$): δ [ppm] 7.82 (s, 1H), 6.85 (t, 1H), 6.37 (m, 2H), 4.72 (br s, 2H), 3.08 (m, 2H), 2.85 (m, 1H), 2.75 (m, 1H), 2.52 (m, 2H), 2.32 (m, 1H), 2.08 (m, 2H), 1.00 (t, 3H).

8.3 N-[4-(4-Isopropyl-benzenesulfonylamino)-indan-2-ylmethyl]-propionamide

N-(4-Amino-indan-2-ylmethyl)-propionamide (0.51 g, 2.34 mmol) was dissolved in pyridine-dichloromethane (1:2, 30 mL) and cooled to 5° C. 4-Isopropylbenzenesulfonyl chloride (0.54 g, 2.47 mmol) was added and the solution stirred at 5° C. for 3 h. Solution was evaporated, partitioned between ethyl acetate and water, and the organic phase separated and dried over $MgSO_4$. The filtered solution was concentrated to give the product as a brown oil (0.95 g, 100%).

MS (ESI) m/z: 401.1 [M+H]$^+$

8.4 4-Isopropyl-N-(2-propylaminomethyl-indan-4-yl)-benzenesulfonamide

N-[4-(4-Isopropyl-benzenesulfonylamino)-indan-2-ylmethyl]propionamide (0.30 g, 0.75 mmol) was dissolved in 10 mL of THF and 2.5 mL (26.1 mmol) of a borane-THF complex was introduced dropwise. The resulting mixture was stirred at reflux for 1 h. The solution was cooled, 3 mL of 2 N HCl was added slowly, and the mixture was stirred at reflux for 2 h. The cooled solution was quenched with water, then NaOH (2N) and extracted with ethyl acetate. The organic phase was dried over $MgSO_4$, filtered, and the filtrate was evaporated in vacuo to give product as a white solid which was further purified by column chromatography using (dichloromethane-MeOH, 7-12%) to give an oil. The oil was dissolved in ethyl acetate and HCl (4M, dioxane) was added to give the product as a white solid (140 mg, 43%).

MS (ESI) m/z: 387.1 [M+H]$^+$ $^1$H-NMR (DMSO-d$_6$): δ [ppm] 7.68 (d, 2H), 7.26 (d, 2H), 6.93 (d, 1H), 6.88 (s, 1H), 6.73 (d, 1H), 2.98 (m, 3H), 2.74 (m, 4H), 2.60 (m, 2H), 1.22 (d, 6H), 0.89 (t, 3H).

Example 9

4-Isopropyl-N-(2-allylaminomethyl-indan-4-yl)-benzenesulfonamide

9.1 4-Isopropyl-N-(2-aminomethyl-indan-4-yl)-benzenesulfonamide

N-[4-(4-Isopropyl-benzenesulfonylamino)-indan-2-ylmethyl]-propionamide (1.00 g, 2.50 mmol, synthesized as described in Example 8) was dissolved in 25 mL of n-butanol and 10 mL of concentrated (6N) hydrochloric acid was added. The resulting mixture was stirred at reflux for 5 h. The solution was cooled, added to water and extracted with ethyl acetate. The aqueous solution was treated with NaOH (2N) and extracted with ethyl acetate. The organic phase was dried over $MgSO_4$, filtered, and the filtrate was evaporated in vacuo to give product as a white solid which was further purified by column chromatography using (dichloromethane-MeOH, 5-50%) to give a yellow oil (160 mg, 18%).

MS (ESI) m/z: 345.5 [M+H]$^+$ 9.2 4-Isopropyl-N-(2-allylaminomethyl-indan-4-yl)-benzenesulfonamide 4-Isopropyl-N-(2-aminomethyl-indan-4-yl)-benzenesulfonamide (80 mg, 0.23 mmol), allyl bromide (30 mg, 0.23 mmol) and triethylamine (20 mg, 0.23 mmol) were dissolved in 2 mL of DMF and stirred at room temperature for 18 h. The solution was concentrated, water added and extracted with ethyl acetate. The organic phase was dried over $MgSO_4$, filtered and the filtrate was evaporated in vacuo to give a residue which was purified by column chromatography using (dichloromethane-MeOH, 0-5%) to give a yellow oil (10 mg, 6%).

MS (ESI) m/z: 385.1 $[M+H]^+$ $^1$H-NMR (DMSO-$d_6$): δ [ppm] 7:69 (d, 2H), 7.25 (d, 2H), 6.93 (d, 1H), 6.88 (s, 1H), 6.73 (d, 1H), 5.92 (m, 1H), 5.20 (m, 2H), 3.36 (d, 2H), 2.96 (m, 3H), 2.74 (m, 2H), 2.60 (m, 2H), 1.55 (m, 2H), 1.25 (d, 6H).

Example 10

4-Isopropyl-N-(1-propylaminomethyl-indan-5-yl)-benzenesulfonamide 10.1 N-(5-Bromo-indan-1-ylmethyl)-propionamide A solution of (5-bromo-indan-1-yl)-methylamine (240 mg, 0.91 mmol) and triethylamine (363 mg, 3.60 mmol) in THF (5 mL) was stirred at 5° C. and propionic anhydride (125 mg, 0.96 mmol) added dropwise. After the mixture was stirred for 18 h at room temperature, the solvent was removed and ethyl acetate/water were added. The organic layer was washed with water and dried over $MgSO_4$. The filtrate was concentrated to give a white solid (250 mg, 97%).

MS (ESI) m/z: 401.1 $[M+H]^+$ 10.2 N-[5-(4-Isopropyl-benzenesulfonylamino)-indan-1-ylmethyl]-propionamide N-(5-Bromo-indan-1-ylmethyl)-propionamide (280 mg, 0.99 mmol) was dissolved in THF (5 mL) and tris(dibenzylideneacetone)dipalladium (45 mg, 0.05 mmol) and tri-t-butylphosphine (10 mg, 0.05 mmol) added under $N_2$ atmosphere. A solution of 4-isopropylbenzenesulfonyl chloride (198 mg, 0.99 mmol) and NaH (52 mg, 50% in oil) was added and the solution stirred at 150° C. for 1.5 h in a microwave.

Solution was evaporated, partitioned between ethyl acetate and water, and the organic phase separated and dried over $MgSO_4$. The filtered solution was concentrated and separated by preparative HPLC (20-95% MeOH) to give the 2 isomeric amino products and a mixed fraction (92 mg, 22%). The product was obtained as a colorless oil (21 mg, 5%).

10.3 4-Isopropyl-N-(1-propylaminomethyl-indan-5-yl)-benzenesulfonamide

The borane reduction was carried out by the aforementioned procedure. The final product was obtained as a white solid.

MS (ESI) m/z: 387.4 $[M+H]^+$ $^1$H-NMR (DMSO-$d_6$): δ [ppm] 7.69 (d, 2H), 7.26 (d, 2H), 7.07 (d, 1H), 6.98 (s, 1H), 6.80 (d, 1H), 3.30 (m, 1H), 2.90 (m, 2H), 2.88-2.65 (m, 2H), 2.65 (m, 4H), 2.28 (m, 1H), 1.81 (m, 1H), 1.55 (m, 2H), 1.25 (d, 6H), 0.88 (t, 3H).

Example 11

4-Isopropyl-N-(2-propyl-2,3,4,9-tetrahydro-1H-beta-carboline-7-yl)-benzenesulfonamide×0.3 Acetate 11.1 2-Propyl-2,3,4,9-tetrahydro-1H-beta-carboline 2,3,4,9-Tetrahydro-1H-beta-carbolin (2.5 g, 14.5 mmol) and propionaldehyde (1.06 ml, 14.5 mmol) were dissolved in THF (100 ml). Acetic acid (1.25 ml, 21.8 mmol) and sodium trisacetoxyborohydride (4.615 g, 21.8 mmol) were sequentially added to the reaction mixture and stirred for 1 h at room temperature. The reaction mixture was concentrated and the residue was dissolved in $H_2O$ (10 ml) and ethyl acetate (50 ml). The pH was adjusted to 9 by adding NaOH (2M). The organic phase was separated, dried over magnesium sulfate, filtered, and evaporated to dryness to yield the title product (2.84 g, 91%).

ESI-MS: 215.1 $[M+H]^+$ 11.2 1-(2-Propyl-1,2,3,4-tetrahydro-beta-carbolin-9-yl)-ethanone To 2-propyl-2,3,4,9-tetrahydro-1H-beta-carboline (1.46 g, 6.81 mmol) in N,N-dimethylformamide (80 ml) was added sodiumhydride (50% in oil) (392 mg, 8.17 mmol). After 15 minutes, acetyl chloride (0.58 ml, 8.17 mmol) was added to the reaction mixture and stirring continued at room temperature overnight. The solvent was removed in vacuo.

The residue was diluted with water (50 ml) and extracted three times with ethyl acetate. The combined organic phases were dried over magnesium sulfate, filtered, and evaporated to dryness to yield 2.4 g of crude product. The crude product was purified with silica gel chromatography with cyclohexane/ethyl acetate (80:20) as eluent to give the title product (1.15 g, 66% yield).

ESI-MS: 257.1 $[M+H]^+$ 11.3 1-(7-Nitro-2-propyl-1,2,3,4-tetrahydro-beta-carbolin-9-yl)-ethanone To 1-(2-propyl-1,2,3,4-tetrahydro-beta-carbolin-9-yl)-ethanone (1.05 g, 4.1 mmol) in conc. $H_2SO_4$ was added $KNO_3$ (435 mg, 4.3 mmol) in small portions at 0° C. The reaction mixture was allowed to warm up to room temperature and stirred for an additional 30 minutes. The reaction mixture was poured onto 250 ml of ice and extracted once with ethyl acetate. The aqueous phase was made alkaline and extracted twice with ethyl acetate. The combined organic phases were dried over magnesium sulfate, filtered, and evaporated to dryness to yield 1.2 g of crude product (70% purity).

ESI-MS: 303.1 $[M+H]^+$ 11.4 2-Propyl-2,3,4,9-tetrahydro-1H-beta-carbolin-7-ylamine To 1-(7-nitro-2-propyl-1,2,3,4-tetrahydro-beta-carbolin-9-yl)-ethanone (1.2 g, 2.79 mmol, 70% purity) in methanol (50 ml) was added tin dichloride (5.03 g, 22.3 mmol) and the reaction mixture was refluxed for 3 h. The solvent was removed, the residue treated with 1 N aqueous sodium hydroxide and ethyl acetate, filtered through celite, the phases separated and the aqueous phase extracted twice with ethyl acetate. The combined organic phases were dried over magnesium sulfate, filtered, and evaporated to dryness to yield 700 mg of crude product. The crude product was purified with silica gel chromatography with ethyl acetate/methanol (95:5) as eluent to give the desired product (300 mg, 45% yield).

ESI-MS: 230.1 [M+H]$^+$ $^1$H-NMR (CDCl$_3$, 400 MHz): δ [ppm] 7.3 (d, 1H), 6.6 (s, 1H), 6.5 (d, 1H), 3.6 (m, 2H), 2.8 (m, 2H), 2.7 (m, 2H), 2.5 (m, 2H), 1.6 (m, 2H), 0.9 (m, 3H).

11.5 4-Isopropyl-N-(2-propyl-2,3,4,9-tetrahydro-1H-beta-carbolin-7-yl)-benzenesulfonamide×0.3 Acetate 2-Propyl-2,3,4,9-tetrahydro-1H-beta-carbolin-7-ylamine (100 mg, 0.41 mmol) and 4-isopropyl-phenyl-sulfonyl chloride (91 mg, 0.41 mmol) were dissolved in tetrahydrofuran (15 ml). Triethylamine (0.17 ml, 1.24 mmol) was added and the reaction mixture stirred over night at room temperature. The solvent was evaporated under reduced pressure, the residue treated with H$_2$O and extracted twice with ethyl acetate (50 ml). The organic layer was dried over magnesium sulfate, filtered, and the solvent evaporated under reduced pressure to give the crude product. The crude product was purified via preparative HPLC (DeltaPak, 40 mm diameter) with acetonitrile/water/0.01% acetic acid as eluent to give the desired product (40 mg, 22% yield)

ESI-MS: 412.1 [M+H]$^+$ $^1$H-NMR (DMSO-d$_6$, 400 MHz): δ [ppm] 10.6 (bs; 1H), 9.8 (bs, 1H), 7.6 (d, 2H), 7.4 (d, 2H), 7.2 (d, 1H), 7.1 (s, 1H), 6.7 (dd, 1H), 3.5 (bs, 2H), 2.9 (sept, 6H), 2.7 (m, 2H), 2.6 (m, 2H), 2.5 (m, 2H), 1.9 (bs, 1H), 1.5 (m, 2H), 1.2 (d, 6H), 0.9 (t, 3H).

$^{13}$C-NMR (DMSO-d$_6$, 100 MHz): δ [ppm] 172.1 (s), 153.1 (s), 137.3 (s), 135.8 (s), 130.8 (s), 126.9 (d), 126.8 (d), 124.0 (s), 117.4 (d), 113.4 (d), 106.4 (s), 104.1 (d), 59.0 (t), 50.7 (t), 49.9 (t), 33.2 (d), 23.4 (q), 21.0 (t), 19.9 (t), 11.7 (q).

Example 12

4-Isopropyl-N-(2-propyl-2,3,4,4a,9,9a-hexahydro-1H-beta-carbolin-7-yl)-benzenesulfonamide To 4-isopropyl-N-(2-propyl-2,3,4,9-tetrahydro-1H-beta-carbolin-7-yl)-benzenesulfonamide (25 mg, 0.05 mmol) in trifluoro-acetic acid (5 ml) was added sodium cyanoborohydride (15 mg, 0.24 mmol). After 15 min of stirring at room temperature the reaction mixture was made alkaline and extracted twice with ethyl acetate. The combined organic phases were dried over magnesium sulfate, filtered, and evaporated to dryness to yield the crude product. Trifluoroacetic acid was added and the product lyophilised (6.4 mg, 24% yield).

ESI-MS: 414.1 [M+H]$^+$

Example 13

N-(6,8-Dichloro-2-propyl-2,3,3a,4,5,9b-hexahydro-1H-benzo[e]isoindol-7-yl)-4-isopropyl-benzene-sulfonamide, hydrochloride 13.1 6,8-Dichloro-2-propyl-2,3,3a,4,5,9b-hexahydro-1H-benzo[e]isoindol-7-yl-amine 6,8-Dichloro-2,3,3a,4,5,9b-hexahydro-1H-benzo[e]isoindol-7-ylamine (275 mg, 1.07 mmol) and propionaldehyde (81 µl, 1.12 mmol) were dissolved in tetrahydrofuran (25 ml). Acetic acid (90 µl, 1.6 mmol) and sodium trisacetoxyborohydride (340 mg, 1.6 mmol) were sequentially added to the reaction mixture and stirred for 1 hour at room temperature. The reaction mixture was concentrated and the residue was dissolved in a 1 M NaOH solution (20 ml) and ethyl acetate (20 ml). The aqueous phase was extracted once more with ethyl acetate. The combined organic phases were dried over magnesium sulfate, filtered, and evaporated to dryness to yield the pure product (295 mg, 92%).

ESI-MS: 299.05 [M+H]$^+$ $^1$H-NMR (DMSO-d$_6$, 400 MHz): δ [ppm] 7.05 (s, 1H), 5.2 (s, 2H), 3.25 (m, 1H), 3.1 (m, 1H), 3.0 (m, 1H), 2.65 (m, 1H), 2.6 (m, 1H), 2.45 (m, 1H), 2.3 (m, 2H), 2.15 (m, 1H), 2.05 (m, 1H), 1.65 (m, 1H), 1.5 (m, 1H), 1.45 (m, 2H), 0.85 (m, 1H).

13.2 N-(6,8-Dichloro-2-propyl-2,3,3a,4,5,9b-hexahydro-1H-benzo[e]isoindol-7-yl)-4-isopropyl-benzenesulfonamide, hydrochloride 6,8-Dichloro-2-propyl-2,3,3a,4,5,9b-hexahydro-1H-benzo[e]isoindol-7-yl-amine (100 mg, 0.33 mmol) and polystyrene-bound DMAP (4-(N,N-dimethylamino)pyridine) (loading 1.06 mmol/g, 32 mg) were treated with tetrahydrofuran (10 ml). Subsequently isopropylphenylsulfonyl chloride (73 mg, 0.33 mmol) was added and stirred for 5 hours at 150° C. in the microwave (CEM). Another portion of isopropylphenylsulfonyl chloride and polystyrene-bound DMAP was added and stirring continued for 7 hours at 160° C. in the microwave. The solvent was evaporated under reduced pressure, the residue treated with water (30 ml) and twice extracted with ethyl acetate (2×30 ml). The organic layer was dried over magnesium sulfate, filtered, and the solvent evaporated under reduced pressure to give an oil (470 mg). The crude product was purified via HPLC chromatography. Fractions containing the product were combined and the solvent evaporated. The residue was converted into the hydrochloride salt (4 mg, 2%).

ESI-MS: 481.15/483.15 [M+H]$^+$ $^1$H-NMR (DMSO-d$_6$, 400 MHz): δ [ppm] 10.4 (bs, 1H), 9.95 (s, 1H), 7.7 (d, 2H), 7.45 (m, 3H), 4.1 (m, 0.5H), 3.85 (m, 0.5H), 3.7 (m, 0.5H), 3.55 (m, 0.5H), 3.45 (m, 1H), 3.1 (m, 2H), 3.0 (sept, 1H), 2.95-2.55 (m, 5H), 1.85 (m, 1H), 1.65 (m, 3H), 1.2 (d, 6H), 0.9 (t, 3H).

Example 14

4-Isopropyl-N-(2-propyl-2,3,3a,4,5,9b-hexahydro-1H-benzo[e]isoindol-7-yl)-benzenesulfonamide, hydrochloride 14.1 2-Propyl-2,3,3a,4,5,9b-hexahydro-1H-benzo[e]isoindol-7-yl-amine A mixture of 6,8-dichloro-2-propyl-2,3,3a,4,5,9b-hexahydro-1H-benzo[e]isoindol-7-yl-amine (800 mg, 2.67 mmol) and 20% palladiumhydroxide on carbon in methanol (50 ml) was hydrogenated over night at room temperature. The catalyst was filtered, and the solvent was removed under vacuum to yield the crude product. The residue was dissolved in ethyl acetate and 1 M NaOH solution. The aqueous phase was once more extracted with ethyl acetate. The combined organic layers were dried over magnesium sulfate, filtered, and the solvent evaporated under reduced pressure to give the pure product (530 mg, 86%).

ESI-MS: 231.15 [M+H]$^+$ 14.2 4-Isopropyl-N-(2-propyl-2,3,3a,4',5,9b-hexahydro-1H-benzo[e]isoindol-7-yl)-benzenesulfonamide, hydrochloride 2-Propyl-2,3,3a,4,5,9b-hexahydro-1H-benzo[e]isoindol-7-yl-amine (40 mg, 0.17 mmol) and 4-isopropylphenylsulfonyl chloride (38 mg, 0.17 mmol) were dissolved in tetrahydrofuran (20 ml). Triethylamine (70 µl, 0.52 mmol) was added and the reaction mixture stirred over night at room temperature. The solvent was evaporated under reduced pressure, the residue treated with water (30 ml) and ethyl acetate (30 ml). The aqueous phase was once more extracted with ethyl acetate and the combined organic phases were dried over magnesium sulfate, filtered, and the solvent evaporated under reduced pressure to give the crude product (120 mg). The crude product was purified via silica gel chromatography with cyclohexane/ethyl acetate (gradient 0-100%). Fractions containing the product were combined and the solvent evaporated to yield the pure product which was converted into its hydrochloride salt (15 mg, 18%).

ESI-MS: 413.2 [M+H]$^+$ $^1$H-NMR (DMSO-d$_6$, 400 MHz): δ [ppm] 10.4 (bs, 1H), 10.2 (s, 1H), 7.7 (d, 2H), 7.45 (d, 2H), 7.05 (d, 1H), 6.95 (d, 1H), 6.9 (m, 2H), 3.9 (m, 1H), 3.4 (m, 2H), 3.05 (m, 2H), 2.95 (sept, 1H), 2.8 (m, 1H), 2.6 (m, 4H), 1.65 (m, 4H), 1.2 (d, 6H), 0.9 (t, 3H).

Example 15

N-(2-Propyl-2,3,3a,4,5,9b-hexahydro-1H-benzo[e] isoindol-7-yl)-4-(2,2,2-trifluoro-1-methylethyl)-benzenesulfonamide, hydrochloride Following a procedure analogous to that described in example 14 the title compound was obtained.

ESI-MS: 467.25 [M+H]$^+$ $^1$H-NMR (DMSO-d$_6$, 400 MHz): δ [ppm] 10.7 (bs, 1H), 10.3 (m, 1H), 7.8 (d, 2H), 7.6 (d, 2H), 7.05 (m, 1H), 6.95 (d, 1H), 6.9 (m, 1H), 3.9 (m, 2H), 3.4 (m, 2H), 3.05 (m, 2H), 2.8 (m, 1H), 2.6 (m, 4H), 1.7 (m, 4H), 1.45 (m, 3H), 0.9 (m, 3H).

Example 16

N-(2-Propyl-2,3,3a,4,5,9b-hexahydro-1H-benzo[e] isoindol-7-yl)-4-trifluoromethoxy-benzenesulfonamide hydrochloride Following a procedure analogous to that described in example 14 the title compound was obtained.

ESI-MS: 455.15 [M+H]$^+$ $^1$H-NMR (DMSO-d$_6$, 400 MHz): δ [ppm] 10.4 (s, 1H), 10.3 (bs, 1H), 7.9 (d, 2H), 7.6 (d, 2H), 7.05 (d, 1H), 6.9 (m, 3H), 3.9 (m, 1H), 3.45 (m, 2H), 3.05 (m, 2H), 2.85 (m, 1H), 2.6 (m, 4H), 1.65 (m, 4H), 0.9 (m, 3H).

Example 17

4-Difluoromethoxy-N-(2-propyl-2,3,3a,4,5,9b-hexahydro-1H-benzo[e]isoindol-7-yl)-benzenesulfonamide, hydrochloride Following a procedure analogous to that described in example 14 the title compound was obtained.

ESI-MS: 437.15 [M+H]$^+$ $^1$H-NMR (DMSO-d$_6$, 400 MHz): δ [ppm] 10.65 (bs, 1H), 10.3 (s, 1H), 7.85 (d, 2H), 7.4 (t, J=70 Hz, 1H), 7.35 (d, 2H), 7.05 (d, 1H), 6.95 (m, 3H), 3.85 (m, 1H), 3.45 (m, 2H), 3.05 (m, 2H), 2.8 (m, 1H), 2.6 (m, 4H), 1.7 (m, 4H), 0.9 (m, 3H).

III. Examples of Galenic Administration Forms

A) Tablets

Tablets of the following composition are pressed on a tablet press in the customary manner:

| | |
|---|---|
| 40 mg | of substance from Example 8 |
| 120 mg | of corn starch |
| 13.5 mg | of gelatin |
| 45 mg | of lactose |
| 2.25 mg | of Aerosil ® (chemically pure silicic acid in submicroscopically fine dispersion) |
| 6.75 mg | of potato starch (as a 6% paste) |

B) Sugar-Coated Tablets

| | |
|---|---|
| 20 mg | of substance from Example 8 |
| 60 mg | of core composition |
| 70 mg | of saccharification composition |

The core composition consists of 9 parts of corn starch, 3 parts of lactose and 1 part of 60:40 vinylpyrrolidone/vinyl acetate copolymer. The saccharification composition consists of 5 parts of cane sugar, 2 parts of corn starch, 2 parts of calcium carbonate and 1 part of talc. The sugar-coated tablets which had been prepared in this way are subsequently provided with a gastric juice-resistant coating.

IV. Biological Investigations

Receptor Binding Studies:

The substance to be tested was either dissolved in methanol/Chremophor® (BASF-AG) or in dimethyl sulfoxide and then diluted with water to the desired concentration.

Dopamine D$_3$ Receptor:

The assay mixture (0.250 ml) was composed of membranes derived from ~10$^6$ HEK-293 cells possessing stably expressed human dopamine D$_3$ receptors, 0.1 nM [$^{125}$I]-iodosulpride and incubation buffer (total binding) or, in addition, test substance (inhibition curve) or 1 µM spiperone (nonspecific binding). Each assay mixture was run in triplicate.

The incubation buffer contained 50 mM tris, 120 mM NaCl, 5 mM KCl, 2 mM CaCl$_2$, 2 mM MgCl$_2$ and 0.1% bovine serum albumin, 10 µM quinolone and 0.1% ascorbic acid (prepared fresh daily). The buffer was adjusted to pH 7.4 with HCl.

Dopamine D$_{2L}$ Receptor:

The assay mixture (1 ml) was composed of membranes from ~10$^6$ HEK-293 cells possessing stably expressed human dopamine D$_{2L}$ receptors (long isoform) and 0.01 nM [$^{125}$I] iodospiperone and incubation buffer (total binding) or, in addition, test substance (inhibition curve) or 1 µM haloperidol (nonspecific binding). Each assay mixture was run in triplicate.

The incubation buffer contained 50 mM tris, 120 mM NaCl, 5 mM KCl, 2 mM CaCl$_2$, 2 mM MgCl$_2$ and 0.1% bovine serum albumin. The buffer was adjusted to pH 7.4 with HCl.

Measurement and Analysis:

After having been incubated at 25° C. for 60 minutes, the assay mixtures were filtered through a Whatman GF/B glass fiber filter under vacuum using a cell collecting device. The filters were transferred to scintillation viols using a filter transfer system. After 4 ml of Ultima Gold® (Packard) have been added, the samples were shaken for one hour and the radioactivity was then counted in a Beta-Counter (Packard, Tricarb 2000 or 2200CA). The cpm values were converted into dpm using a standard quench series and the program belonging to the instrument.

The inhibition curves were analyzed by means of iterative nonlinear regression analysis using the Statistical Analysis System (SAS) which is similar to the "LIGAND" program described by Munson and Rodbard.

The results of the receptor binding studies are expressed as receptor binding constants $K_i(D_2)$ and $K_i(D_3)$, respectively, as herein before described, and given in table 1.

In these tests, the compounds according to the invention exhibit very good affinities for the $D_3$ receptor (<10 nM, frequently <5 nM) and bind selectively to the $D_3$ receptor.

The results of the binding tests are given in table 1.

TABLE 1

| Example | $K_i(D3)$* [nM] | $K_i(D2)$* [nM] | $K_i(D2)$*/$K_i(D3)$* |
|---|---|---|---|
| 1 | 5.8 | 225 | 39 |
| 2 | 9.4 | 517 | 55 |
| 3 | 55 | 55 | 23 |
| 4 | 63.4 | 7,640 | 120 |
| 5 | 1.72 | 119 | 69 |
| 7 | 7.4 | 398 | 54 |
| 9 | 4.3 | 232 | 54 |
| 10 | 1.32 | 58.6 | 45 |
| 12 | 5.3 | 137 | 26 |
| 13 | 10.1 | | 5 |
| 14 | 0.5 | | 28 |
| 15 | 1.8 | | 36 |
| 16 | 3.6 | | 66 |
| 17 | 3.3 | | 19 |

*Receptor binding constants obtained according to the assays described herein before

We claim

1. An aminomethyl substituted bicyclic aromatic compound of the formula I

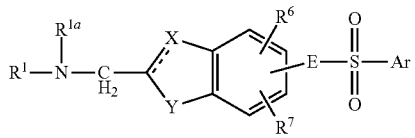

(I)

wherein

Ar is a cyclic radical selected from the group consisting of phenyl and a 5- or 6-membered C-bound heteroaromatic radical comprising as ring members 1, 2 or 3 heteroatoms which are, independently of each other, selected from O, S and N, where the cyclic radical Ar may carry 1, 2 or 3 substituents $R^a$;

$R^a$ is halogen, $C_1$-$C_6$-alkyl, fluorinated $C_1$-$C_6$-alkyl, $C_1$-$C_6$-hydroxyalkyl, $C_1$-$C_6$-alkoxy-$C_1$-$C_6$-alkyl, $C_1$-$C_6$-alkenyl, fluorinated $C_1$-$C_6$-alkenyl, $C_3$-$C_6$-cycloalkyl, fluorinated $C_3$-$C_6$-cycloalkyl, $C_1$-$C_6$-alkoxy, $C_1$-$C_6$-hydroxyalkoxy, $C_1$-$C_6$-alkoxy-$C_1$-$C_6$-alkoxy, fluorinated $C_1$-$C_6$-alkoxy, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_1$-alkylsulfonyl, fluorinated $C_1$-$C_6$-alkylsulfonyl, CN, nitro, $C_1$-$C_6$-alkylcarbonyl, fluorinated $C_1$-$C_6$-alkylcarbonyl, $C_1$-$C_6$-alkylcarbonylamino, fluorinated $C_1$-$C_6$-alkylcarbonylamino, $C_1$-$C_6$-alkylcarbonyloxy, fluorinated $C_1$-$C_6$-alkylcarbonyloxy, $C_1$-$C_6$-alkoxycarbonyl, carboxy, NH—C(O)—$NR^4R^5$, $NR^4R^5$, $NR^4R^5$-$C_1$-$C_6$-alkylene, O—$NR^4R^5$, C(O) $NR^4R^5$, $SO_2NR^4R^5$, phenylsulfonyl, benzyloxy, phenoxy, or a saturated or unsaturated 3- to 7-membered heterocyclic ring comprising as ring members 1, 2, 3 or 4 heteroatoms selected from N, O and S and/or 1, 2 or 3 heteroatom-containing groups selected from $NR^9$, where $R^9$ has one of the meanings given for $R^8$, SO, $SO_2$ and CO, and where the 5 last-mentioned radicals $R^a$ may carry 1, 2, 3 or 4 substituents selected from hydroxy and the radicals $R^a$;

X is a covalent bond or N—$R^2$, $CHR^2$, $CHR^2CH_2$, N or C—$R^2$;

Y is N—$R^{2a}$, $CHR^{2a}$, $CHR^{2a}CH$, or $CHR^{2a}CH_2CH_2$;

=== is a single bond or a double bond;

E is $CH_2$ or $NR^3$;

$R^1$ is H, $C_1$-$C_4$-alkyl, $C_3$-$C_4$-cycloalkyl, $C_3$-$C_4$-cycloalkylmethyl, $C_3$-$C_4$-alkenyl, fluorinated $C_1$-$C_4$-alkyl, fluorinated $C_3$-$C_4$-cycloalkyl, fluorinated $C_3$-$C_4$-cycloalkylmethyl, fluorinated $C_3$-$C_4$-alkenyl, formyl or $C_1$-$C_3$-alkylcarbonyl;

$R^{1a}$ is H, $C_1$-$C_4$-alkyl, $C_3$-$C_4$-cycloalkyl, $C_3$-$C_4$-alkenyl, fluorinated $C_1$-$C_4$-alkyl, fluorinated $C_3$-$C_4$-cycloalkyl, or fluorinated $C_3$-$C_4$-alkenyl, $R^2$ and $R^{2a}$ each independently are H, $CH_3$, $CH_2F$, $CHF_2$ or $CF_3$ or $R^{1a}$ and $R^2$ or $R^{1a}$ and $R^{2a}$ together are $(CH_2)_n$ with n being 1, 2 or 3;

$R^3$ is H or $C_1$-$C_4$-alkyl;

$R^4$ and $R^5$ independently of each other are H, $C_1$-$C_4$-alkyl, fluorinated $C_1$-$C_4$-alkyl or $C_1$-$C_4$-alkoxy or may form, together with N, a 4-, 5- or 6-membered saturated or unsaturated ring;

$R^6$ and $R^7$ independently of each other are H or halogen;

or physiologically tolerated acid addition salts thereof.

2. The compound as claimed in claim 1, of the formula I.1

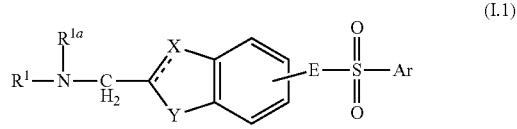

(I.1)

wherein

Ar is phenyl or an aromatic 5- or 6-membered C-bound heteroaromatic radical, comprising 1 nitrogen atom as ring member and 0, 1, 2 or 3 further heteroatoms, independently of each other, selected from O, S and N, as ring members, wherein Ar may carry 1, 2 or 3 radicals $R^a$ which are, independently of each other, selected from the group consisting of halogen, $C_1$-$C_6$-alkyl, $C_3$-$C_6$-cycloalkyl, $C_1$-$C_6$-alkoxy, fluorinated $C_1$-$C_6$-alkyl, fluorinated $C_3$-$C_6$-cycloalkyl, fluorinated $C_1$-$C_6$-alkoxy, $NR^4R^5$, 1-aziridinyl, azetidin-1-yl, pyrrolidin-1-yl or piperidin-1-yl, wherein the last four mentioned radicals may be fluorinated, and an aromatic 5- or 6-membered C-bound heteroaromatic radical, comprising 1 nitrogen atom as ring member and 0, 1, 2 or 3 further heteroatoms, independently of each other, selected from O, S and N, wherein the last mentioned radical may carry 1, 2, 3 or 4 radicals selected from halogen and the radicals $R^a$;

$R^4$ and $R^5$, independently of each other, are selected from H, $C_1$-$C_2$-alkyl and fluorinated $C_1$-$C_2$-alkyl; and X, Y, ===, E, $R^1$, $R^{1a}$, $R^2$, $R^{2a}$ and $R^3$ are as defined in claim 1.

3. The compound as claimed in claim 1, wherein Ar carries one radical $R^a$ of the formula $R^{a'}$

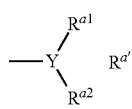

wherein

Y is N, CH or CF, $R^{a1}$ and $R^{a2}$ are independently of each other selected from $C_1$-$C_2$-alkyl, fluorinated $C_1$-$C_2$-alkyl, or provided for Y being CH or CF one of the radicals $R^{a1}$ or $R^{a2}$ may also be hydrogen or fluorine, or $R^{a1}$ and $R^{a2}$ together form a radical $(CH_2)_m$ wherein 1 or 2 of the hydrogen atoms may be replaced by fluorine, hydroxy, oxo, $C_1$-$C_2$-alkyl or $C_1$-$C_2$-alkoxy, wherein one $CH_2$ moiety may be replaced by O, S, S=O, $SO_2$ or N—$R^c$, $R^c$ being hydrogen or $C_1$-$C_2$-alkyl and wherein m is 2, 3, 4, 5 or 6.

4. The compound as claimed in claim 3, wherein the radical $R^{a'}$ is selected from isopropyl, (R)-1-fluoroethyl, (S)-1-fluoroethyl, 2-fluoroethyl, 1,1-difluoroethyl, 2,2-difluoroethyl, 2,2,2-trifluoroethyl, (R)-1-fluoropropyl, (S)-1-fluoropropyl, (R)-2-fluoropropyl, (S)-2-fluoropropyl, 3-fluoropropyl, 1,1-difluoropropyl, 2,2-difluoropropyl, 3,3-difluoropropyl, 3,3,3-trifluoropropyl, (R)-2-fluoro-1-methylethyl, (S)-2-fluoro-1-methylethyl, (R)-2,2-difluoro-1-methylethyl, (S)-2,2-difluoro-1-methylethyl, (R)-1,2-difluoro-1-methylethyl, (S)-1,2-difluoro-1-methylethyl, (R)-2,2,2-trifluoro-1-methylethyl, (S)-2,2,2-trifluoro-1-methylethyl, 2-fluoro-1-(fluoromethyl)ethyl, 1-(difluoromethyl)-2,2-difluoroethyl, cyclopropyl, cyclobutyl, 1-fluorocyclopropyl, (R)- and (S)-2,2-difluorocyclopropyl, (R)- and (S)-2-fluorocyclopropyl.

5. The compound as claimed in claim 3, wherein the radical $R^{a'}$ is selected from 4-morpholinyl, 4-thiomorpholinyl, 4-(1,1-dioxo)thiomorpholinyl, piperazin-1-yl, 4-methylpiperazin-1-yl, azetidin-1-yl, 2-methylazetidin-1-yl, (S)-2-methylazetidin-1-yl, (R)-2-methylazetidin-1-yl, 3-fluoroazetidin-1-yl, 3-methoxyazetidin-1-yl, 3-hydroxyazetidin-1-yl, pyrrolidin-1-yl, pyrrolidin-2-yl, (S)-pyrrolidin-2-yl, (R)-pyrrolidin-2-yl, pyrrolidin-3-yl, (S)-pyrrolidin-3-yl, (R)-pyrrolidin-3-yl, 2-fluoropyrrolidin-1-yl, (S)-2-fluoropyrrolidin-1-yl, (R)-2-fluoropyrrolidin-1-yl, 3-fluoropyrrolidin-1-yl, (S)-3-fluoropyrrolidin-1-yl, (R)-3-fluoropyrrolidin-1-yl, 2,2-difluoropyrrolidin-1-yl, 3,3-difluoropyrrolidin-1-yl, 2-methylpyrrolidin-1-yl, (S)-2-methylpyrrolidin-1-yl, (R)-2-methylpyrrolidin-1-yl, 3-methylpyrrolidin-1-yl, (S)-3-methylpyrrolidin-1-yl, (R)-3-methylpyrrolidin-1-yl, 1-methylpyrrolidin-2-yl, (S)-1-methylpyrrolidin-2-yl, (R)-1-methylpyrrolidin-2-yl, 1-methylpyrrolidin-3-yl, (S)-1-methylpyrrolidin-3-yl, (R)-1-methylpyrrolidin-3-yl, 2,2-dimethylpyrrolidin-1-yl, 3,3-dimethylpyrrolidin-1-yl, 2-trifluoromethylpyrrolidin-1-yl, (S)-2-trifluoromethylpyrrolidin-1-yl, (R)-2-trifluoromethylpyrrolidin-1-yl, 3-trifluoromethylpyrrolidin-1-yl, (S)-3-trifluoromethylpyrrolidin-1-yl, (R)-3-trifluoromethylpyrrolidin-1-yl, 2-oxopyrrolidin-1-yl, 2-oxo-oxazolidin-3-yl, piperidin-1-yl, 2-methylpiperidin-1-yl, (S)-2-methylpiperidin-1-yl and (R)-2-methylpiperidin-1-yl.

6. The compound as claimed in claim 3, wherein the radical $R^{a'}$ carries 1, 2, 3 or 4 fluorine atoms.

7. The compound as claimed in claim 1, where $R^{a'}$ is selected from $OCH_2F$, $OCHF_2$ and $OCF_3$.

8. The compound as claimed in claim 1, wherein Ar carries one radical $R^a$, which is selected from 5- or 6-membered heteroaromatic radicals having as ring members 1 heteroatom selected from O, S and N and which may further have 1, 2 or 3 nitrogen atoms as ring members, and wherein the 5- or 6-membered heteroaromatic radical may carry 1, 2 or 3 substituents selected from halogen, $NO_2$, $NH_2$, OH, CN, $C_1$-$C_6$-alkyl, $C_3$-$C_6$-cycloalkyl, $C_1$-$C_{11}$-alkoxy, fluorinated $C_1$-$C_6$-alkyl, fluorinated $C_3$-$C_6$-cycloalkyl, fluorinated $C_1$-$C_6$-alkoxy, $C_1$-$C_6$-hydroxyalkyl, $C_1$-$C_4$-alkoxy-$C_2$-$C_4$-alkyl, $C_1$-$C_6$-hydroxyalkoxy, $C_1$-$C_4$-alkoxy-$C_2$-$C_4$-alkoxy, $C_1$-$C_6$-alkylcarbonyl, $C_1$-$C_6$-alkylamino, di-$C_1$-$C_6$-alkylamino, $C_1$-$C_6$-alkylaminocarbonyl, di-$C_1$-$C_6$-alkylaminocarbonyl, fluorinated $C_1$-$C_6$-alkylcarbonyl, $C_1$-$C_6$-alkylcarbonylamino, fluorinated $C_1$-$C_6$-alkylcarbonylamino, $C_1$-$C_6$-alkylcarbonyloxy, fluorinated $C_1$-$C_6$-alkylcarbonyloxy, $C_1$-$C_6$-alkoxycarbonyl, $C_1$-$C_6$-alkylthio, fluorinated $C_1$-$C_6$-alkylthio, $C_1$-$C_6$-alkylsulfinyl, $C_1$-$C_6$-alkylsulfonyl, fluorinated $C_1$-$C_6$-alkylsulfinyl and fluorinated $C_1$-$C_6$-alkylsulfonyl.

9. The compound as claimed in claim 8, wherein Ar carries one heteroaromatic radical $R^a$, which is selected from furanyl, thienyl, pyrrolyl, pyrazolyl, imidazolyl, oxazolyl, isoxazolyl, 1,3,4-thiadiazolyl, 1,2,4-triazolyl, 1,2,3-triazolyl and tetrazolyl, where the heteroaromatic radical may be unsubstituted or may carry 1 to 3 substituents selected from halogen, $C_1$-$C_4$-alkyl, $C_1$-$C_4$-alkoxy, fluorinated $C_1$-$C_4$-alkyl and fluorinated $C_1$-$C_4$-alkoxy.

10. The compound as claimed in claim 1, wherein Ar is phenyl.

11. The compound as claimed in claim 1, wherein Ar is phenyl that carries a radical $R^a$ in the 4-position of the phenyl ring.

12. The compounds as claimed in claim 1, wherein E is $NR^3$.

13. The compounds as claimed in claim 1, wherein E is $CH_2$.

14. The compound as claimed in claim 1, wherein X is CH, and Y is CH, or $CH_2CH_2$.

15. The compound as claimed in claim 1, wherein Y is NH and X is CH or N.

16. The compound as claimed in claim 1, wherein Y is $CH_2CH_2$ or $CH_2CH_2CH$, and X is a covalent bond.

17. The compound as claimed in claim 1, wherein X is NH and Y is $CH_2$.

18. The compound as claimed in claim 1, wherein $R^1$ is $C_2$-$C_4$-alkyl, $C_3$-$C_4$-cycloalkyl, $C_3$-$C_4$-cycloalkylmethyl, $C_3$-$C_4$-alkenyl, fluorinated $C_1$-$C_4$-alkyl, fluorinated $C_3$-$C_4$-cycloalkyl or fluorinated $C_3$-$C_4$-alkenyl.

19. The compound as claimed in claim 1, wherein $R^{1a}$ is hydrogen.

20. The compound as claimed in claim 1, wherein $R^{1a}$ is $C_3$-$C_4$-cycloalkyl, $C_3$-$C_4$-alkenyl, fluorinated $C_2$-$C_4$-alkyl, fluorinated $C_3$-$C_4$-cycloalkyl or fluorinated $C_3$-$C_4$alkenyl.

21. The compound as claimed in claim 1, wherein X is $CHR^2$ or $CHR^2CH_2$ and $R^{1a}$ and $R^2$ together are $(CH_2)_n$ with n being 1, 2 or 3.

22. The compound as claimed in claim 1, wherein Y is $CHR^{2a}$, $CHR^{2a}CH$, or $CHR^{2a}CH_2CH_2$ and $R^{1a}$ and $R^{2a}$ together are $(CH_2)_n$ with n being 1, 2 or 3.

23. The compound as claimed in claim 1, wherein X is a covalent bond, Y is $CHR^{2a}CH_2CH_2$ and $R^{1a}$ and $R^{2a}$ together are $(CH_2)$.

24. A pharmaceutical composition comprising at least one compound as claimed in claim 1, optionally together with at least one physiologically acceptable carrier or auxiliary substance.

25. A method for treating one or more of the acute signs, chronic signs, symptoms or malfunctions of a medical disorder selected from Parkinson's disease, schizophrenia, impaired learning and memory, depression, anxiety, psychic disorders and behavioral disturbances caused by the abuse of psychotropic substances, and diabetic nephropathy, said method comprising administering an effective amount of at least one compound as claimed in claim 1 to a subject in need thereof.

26. The method as claimed in claim 25, wherein the medical disorder is schizophrenia.

\* \* \* \* \*

UNITED STATES PATENT AND TRADEMARK OFFICE
CERTIFICATE OF CORRECTION

| | | |
|---|---|---|
| PATENT NO. | : 8,486,984 B2 | Page 1 of 1 |
| APPLICATION NO. | : 11/665287 | |
| DATED | : July 16, 2013 | |
| INVENTOR(S) | : Karla Drescher et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1584 days.

Signed and Sealed this

Thirteenth Day of January, 2015

Michelle K. Lee
*Deputy Director of the United States Patent and Trademark Office*